US008575376B2

(12) United States Patent
Chodounska et al.

(10) Patent No.: US 8,575,376 B2
(45) Date of Patent: Nov. 5, 2013

(54) STEROIDE ANIONIC COMPOUNDS, METHOD OF THEIR PRODUCTION, USAGE AND PHARMACEUTICAL PREPARATION INVOLVING THEM

(75) Inventors: Hana Chodounska, Praha (CZ); Eva Stastna, Praha Chodov (CZ); Vojtech Kapras, Praha (CZ); Ladislav Kohout, Praha (CZ); Jirina Borovska, Tuklaty (CZ); Ladislav Vyklicky, Kamenice (CZ); Karel Vales, Praha (CZ); Ondrej Cais, Praha (CZ); Lukas Rambousek, Koprivnice (CZ); Ales Stuchlik, Celakovice (CZ); Vera Valesova, Lysa nad Labem (CZ)

(73) Assignees: Ustav Organicke Chemie A Biochemie Akademie Ved Ceske Republiky, V.V.I., Praha (CZ); Fyziologicky Ustav Akadamie Ved Ceske Republiky, V.V.I., Praha (CZ); Psychiatricke Centrum Praha, Praha (CZ)

( * ) Notice: Subject to any disclaimer, the term of this patent is extended or adjusted under 35 U.S.C. 154(b) by 0 days.

(21) Appl. No.: 13/321,871

(22) PCT Filed: May 28, 2010

(86) PCT No.: PCT/CZ2010/000065

§ 371 (c)(1),
(2), (4) Date: Dec. 6, 2011

(87) PCT Pub. No.: WO2010/136000

PCT Pub. Date: Dec. 2, 2010

(65) Prior Publication Data

US 2012/0071453 A1 Mar. 22, 2012

(30) Foreign Application Priority Data

May 28, 2009 (CZ) ............................... PV 2009-348

(51) Int. Cl.

| | |
|---|---|
| ***C07J 5/00*** | (2006.01) |
| ***C07J 7/00*** | (2006.01) |
| ***A01N 45/00*** | (2006.01) |
| ***A61K 31/56*** | (2006.01) |
| ***C07J 1/00*** | (2006.01) |

(52) U.S. Cl.
USPC ............................ 552/557; 514/169; 552/502

(58) Field of Classification Search
None
See application file for complete search history.

(56) References Cited

U.S. PATENT DOCUMENTS

| | | | | |
|---|---|---|---|---|
| 2,883,323 | A | 4/1959 | Figdor et al. | |
| 4,060,607 | A * | 11/1977 | Jarreau et al. | 514/175 |
| 2011/0306579 | A1* | 12/2011 | Stein | 514/167 |

FOREIGN PATENT DOCUMENTS

| | | |
|---|---|---|
| WO | WO 0236128 | 5/2002 |

OTHER PUBLICATIONS

Matsumoto et al. Bulletin of the Chemical Society of Japan 1967 (40) 1650-1655.*

Weaver, Charles E., et al., "Geometry and Charge Determine Pharmacological Effects of Steroids..", Jrnl of Pharm. & Exp. Therap., vol. 293, No. 3, Jun. 1, 2000, pp. 747-754.

Stastna, Eva, et al., "Synthesis of C3, C5 and C7 . . . ", Steroids 74, Elsevier Science Publishers, New York, New York, vol. 74, No. 2, Feb. 1, 2009, pp. 256-263.

Park-Chung, Mijeong, et al., "Distinct Sites for Inverse Modulation . . . " Molecular Pharm., Amer. Soc. for Pharm. & Exp. Therap., vol. 52, No. 6, Jan. 1, 1997, pp. 1113-1123.

Cocker, J.D., et al., "Action of Some Steroids on the Central Nervous System", Jrnl of Med. Chemistry, vol. 8, No. 4, Jul. 1965, pp. 417-425.

Atkinson, R. M. et al., "Action of Some Steriods on the Central Nervous System of the mouse. II. Pharmacology", Jrnl. of Med. Chemistry, vol. 8, No. 4, Jul. 1965, pp. 426-432.

* cited by examiner

*Primary Examiner* — Jeffrey S. Lundgren
*Assistant Examiner* — Michael Schmitt
(74) *Attorney, Agent, or Firm* — Notaro, Michalos & Zaccaria P.C.

(57) ABSTRACT

A compound with general formula I (I)

R[1] O H for treatment of various diseases of the central nervous system, in treatment of neuropsychiatric disorders related to imbalance of glutamatergic neurotransmitter system, ischemic damage of CNS, neurodegenerative changes and disorders of CNS, affective disorders, depression, PTSD and other diseases related to stress, anxiety, schizophrenia and psychotic disorders, pain, addictions, multiple sclerosis, epilepsy and gliomas.

1 Claim, 18 Drawing Sheets

Control 3+1 DIV

Control 3+3 DIV

Compound from ex. 9 0.1 ug/ml
3+1DIV

Compound from ex. 9 0.1 ug/ml
3+3DIV

STEROIDE ANIONIC COMPOUNDS, METHOD OF THEIR PRODUCTION, USAGE AND PHARMACEUTICAL PREPARATION INVOLVING THEM

FIELD OF THE INVENTION

This invention is represented by, anionic steroid compounds, ways of their production, their applications and pharmaceutical substances containing them. The invention particularly deals with pregnanolone derivatives substituted in 3alpha-position with the anionic group bound in this position. These derivatives may be beneficial in treatment of several central nervous system (CNS) diseases, especially ischemic CNS injury, neurodegenerative alterations and diseases, depression, post-traumatic stress disorder and other stress-related disorders, schizophrenia and various psychotic diseases, pain, addiction, multiple sclerosis and autoimmune disorders, epilepsy, and gliomas as well as other CNS tumors.

BACKGROUND ART

Glutamate is the principal excitatory neurotransmitter in the central nervous system of mammals. During synaptic transmission, the post-synaptic responses occur via ionotropic and metabotropic glutamate receptors. Metabotropic receptors operate via G-proteins and mobilize calcium ions from intracellular compartments. Activation of ionotropic receptors results in increase in permeability of postsynaptic membrane for sodium, potassium and calcium cations by opening a ion channel, which is an integral parts of the receptors.

Typical examples of ionotropic receptors are N-methyl D-aspartate (NMDA) receptors, AMPA and kainate receptors. Although current knowledge suggests specific role of various types of superfamily of glutamate receptors in the glutamate-induced excitotoxicity, ionotropic receptors are generally considered to be a key player in these processes. Activation of ionotropic receptors leads to alterations in intracellular concentrations, of various ions, mainly of $Na^+$ and $Ca^{2+}$. Current research demonstrates that beside calcium, elevated intracellular levels of sodium ions can also lead to neuronal death. In neuronal cultures and in retina the activation of glutamate receptors may lead to damage even by sodium cations in absence of extracellular calcium ions. Nonetheless, toxicity of elevated glutamate levels is usually associated with elevations in intracellular concentrations of $Ca^{2+}$. Currently it is well established that there is a direct relationship between excessive influx of calcium into cells and glutamate-induced damage to neurons. Glutamate-induced pathological calcium elevation is usually ascribed to prolonged activation of ionotropic receptors. Elevation in intracellular calcium then may trigger the down-stream neurotoxicity cascade, which involves uncoupling of mitochondrial electron transport from ATP production, supranormal activation of enzymes such as calpain and other proteases, induction of specific protein kinases, NO-synthase, calcineurins and endonucleases. These changes may also promote the production of toxic reactive molecules such as reactive oxygen species (ROS) and induce changes in cytoskeleton architecture and activation of signals leading to apoptosis and mitochondrial damage (Villmann and Becker, 2007).

A number of preclinical studies show a remarkable ability of NMDA receptor antagonists to prevent from the excessive exocytose of glutamate and damage to the CNS. From the clinical point of view; however, their therapeutic potential is rather limited. Regarding the fact that glutamate receptors are ones of the most abundant in the CNS, application of their antagonists leads to wide variety of side effects, ranging from motor impairment to induction of psychotic symptoms. On the contrary, a large divergence of NMDA receptors and differences in their distribution at synapses and at extrasynaptic sites offer a possibility to search for drugs which selectively influence only a limited subset of NMDA receptors and thus to avoid the induction of unexpected side effects, while retaining their therapeutic neuroprotective activity.

Previous results demonstrated that naturally occurring 3α5β-pregnanolone sulfate affects the activity of NMDA receptor by a use-dependent manner. As a consequence this molecule has a more pronounced inhibitory action on the tonically active NMDA receptors than on those phasically activated by glutamate during synaptic transmission. It was also demonstrated that activation of extrasynaptic tonically activated NMDA receptors is very important for excitotoxic action of glutamate (Petrovic et al., 2005).

Therefore, we have started the development and testing of novel NMDA receptor antagonists derived from neurosteroids. These newly synthesized drugs exhibit affinity for extrasynaptic NMDA receptors. What is more important, previous electrophysiological studies showed that these compounds bound preferentially to open NMDA receptor channels. Our compounds lack affinity for other types of receptor; it is thus presumed that they will not affect signal transmission between neurons. The suggested mechanisms of their action are the blockade of extrasynaptic tonically activated NMDA receptors and prevention of excessive action of glutamate on neurons.

In the last decade, the biomedical research focused on the study of the role of neurosteroids in the pathogenesis of number of neuropsychiatric diseases and evaluation of their therapeutic potential. Mechanisms of action of neurosteroids are conventionally associated with their activity on NMDA and GABA-A receptors. A number of experimental studies with animal models show their potential in therapy of several diseases of CNS, including neurodegenerative disorders, multiple sclerosis, affective disorders, alcoholism, pain, insomnia or schizophrenia (Morrow, 2007; Weaver, 2000).

Neurosteroids also play a crucial role in the regulation of reactivity to stress and stress-related CNS disorders. Corticosteroid levels are known to acutely increase after exposition to a stressor; this represents an adaptive mechanism. On the other hand, experimental models of chronic stress and depression in laboratory rodents show decreased levels of neurosteroids both in brain and plasma. Similar findings are often reported in patients suffering from depressions and pre-menstruation syndrome suggesting impairments in the CNS homeostatic mechanisms in stress-related neuropsychiatric disorders.

Steroid compounds affect activity and plasticity of neural and glial cells during early in life, and later in development they play an essential trophic and neuroprotective role in the adult CNS. Steroids are released by sexual and adrenal glands as well as in the CNS. Steroids secreted by peripheral glands reach brain, medulla and spinal cord via blood circulation. Nonetheless, some neural steroids (i.e., neurosteroids) are synthesized directly in the CNS. The most studied neurosteroids are represented by pregnenolone, progesterone, dehydroepiandrosterone (DHEA) and their reduced metabolites and sulphate esters. Not much is known about regulation of neurosteroid synthesis in the CNS, but it is generally assumed that they may underlie interaction of multiple cell types in the CNS. For example, synthesis of progesterone by Schwann cells surrounding peripheral nerves is regulated by signals diffusing from neurons.

Neurotrophic and neuroprotective properties of some neurosteroids were convincingly demonstrated both in cultures and in vivo. Progesterone plays a pivotal role in neurological recovery from traumatic brain and spinal cod injury by mechanisms including protection against excitotoxic damage to the brain, lipid peroxidation and by induction expression of specific enzymes. For example, after cutting the spinal cord, this steroid increases the number of NO-synthase-expressing astrocytes in place adjacent to cut both in the distal and proximal segment of the cord.

This steroid was also shown to regulate formation of new myelin sheaths. This fact was shown in regenerating rat sciatic nerve in the culture with sensory neurons and Schwann cells. Progesterone also supports myelination by activation of genes coding for proteins participating in this process.

As mentioned before, neurosteroids importantly modulate the function of membrane receptors for various neurotransmitters, namely $GABA_A$ receptors, NMDA receptors and sigmal-opioid receptors. These mechanisms are most likely responsible for psychopharmacological effects of steroids and may at least partly account for their anticonvulsant, anxiolytic, neuroprotective and sedation effects as well as for their influence upon learning and memory functions. For instance, pregnanolone sulphate was shown to be capable of reversing cognitive deficit in aged animals and exerting a protective effect on memory in several amnesia models. Recent studies have demonstrated direct effect of neurosteroids on intracellular receptors. Despite absence of direct evidence for binding of neurosteroids to corticoid receptors, they may obviously modulate their function indirectly, by interaction with protein kinases C and A, MAP-kinase (MAPK) or CaMKII. Moreover, pregnanolone and pregnanolone sulphate were shown to affect microtubule-associated proteins and increase the rate of microtubule polymeration, which may in turn affect neuronal plasticity. We are far from fully understanding these newly-described effects of neurosteroids, however, their potential role in neuroprotective mechanisms deserves scientific attention.

Sulfated esters of neurosteroids also play a physiological role in the regulation of receptors for excitatory and inhibitory neurotransmitters and participate in the natural protective properties of CNS tissue. Sulphated esters of neurosteroids and their analogues are promising molecules, potentially beneficial for treatment of CNS disorders. Nonetheless, a ratio between neurosteroids and their sulfated esters is maintained enzymatically in the CNS tissue in vivo. Exogenous administration of sulfated esters may not lead to improvement in the protective functions due to increased enzyme activity in the CNS converting them to inactive forms. The invented molecules are metabolically stable analogues of sulfated esters of neurosteroids; moreover, they pass the blood-brain barrier more readily due to their chemical structure. Sulfated and thus polar steroids compounds generally penetrate the blood-brain barrier with difficulty, but it was demonstrated that intravenously administered pregnanolone sulphate can reach the brain. This transport of sulphated analogs is probably mediated by active exchange mechanisms associated with so-called organic anion transport protein (OATP), which is expressed in the cells throughout the CNS.

Advantage of our molecules is that they retain similar pharmacological and physiological properties as pregnanolone sulphate, but they are not degraded by sulfatases into non-conjugated metabolites.

DESCRIPTION OF THE INVENTION

The present invention relates to compounds of general formula I (I)

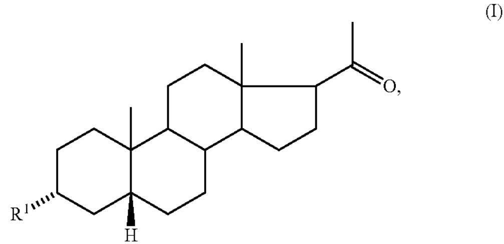

in which $R^1$ represents the group of general formula $R^3OOC—R^2—C(R^4)—R^5$, where $R^2$ means alkyl or alkenyl group with 1 to 18 carbon atoms in a straight or a branching carbon chain, which may be substituted by one or more halogen atoms and amino group, which may be either free or protected by a removable protecting group, alkoxycarbonyl group, aromatic group, and/or heterocyclic group, in which the heteroatom means oxygen atom, sulfur, or nitrogen atom. $R^3$ represents either a hydrogen atom or a protecting group of carboxyl groups, preferably benzyl group; $R^4$ represents oxygen atom, nitrogen atom, or a sulfur atom bound by a double bond, or $R^4$ represents two hydrogen atoms. $R^5$ represents any minimally bivalent atom, preferably an oxygen atom, the nitrogen, or carbon atom, except when $R^2$ represents the group $(CH_2)_n$, where n=0-3, and simultaneously $R^3$ represents a hydrogen atom and $R^4$ and $R^5$ represents an oxygen atom.

The invention is based on results of our experiments, in which effects of pregnanolone sulphate on native and recombinant NMDA receptors. These studies have demonstrated that this naturally occurring neurosteroid inhibits the responses to exogenous application of NMDA receptor agonists. We have demonstrated that pregnanolone sulphate bound exclusively to activated NMDA receptors (i.e., use-dependent action), but it did not bind to the ionic pore of the receptors, as did other substances as $Mg^{2+}$, ketamine, dizocilpine or memantine. Binding kinetics and mechanism of action of pregnanolone sulphate may result to preferential increase in inhibitory action on tonically-active glutamate receptors rather than phasically-activated receptors involved in fast synaptic transmission. The newly synthesizes analogues, which are subject to this invention, have the same mechanism of action on the NMDA receptors as pregnanolone sulphate.

Moreover, since exogenous administration of pregnanolone sulphate does not often lead to beneficial effects due to increase enzymatic activity of sulphatases, our molecules are their non-hydrolysable analogues.

Endogenous 3α-C sulphated neurosteroids have therapeutic potential, but their clinical use is complicated due to their metabolic and pharmacokinetic properties. First, these neurosteroids are metabolically converted through the action of steroid sulfatase to drugs with opposite biological effect. Second, they do not easily cross the blood-brain barrier (BBB). Third, they have side effects originating in their NMDA receptor antagonism.

Presented compounds are not converted by enzymes, they cross the BBB, and they do not show the side effects of NMDA antagonism. Furthermore, they show potentially therapeutic effect in animal models of CNS disorders.

This invention relates also to the method of production of above mentioned compounds of general formula I where $R^1$ is as indicated above. The method of production of compound of general formula I, where $R^1$ means the same as above and $R^5$ represents oxygen atom, starts from 3alfa-hydroxy-5beta-pregnan-20-one of formula II (II)

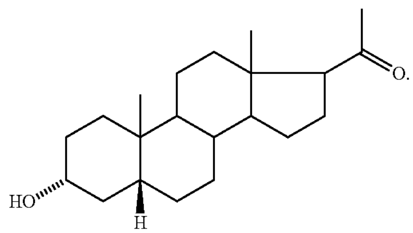

This compound of formula II can be transferred to the compound of general formula I, where $R^1$ means the same as above and $R^5$ represents oxygen atom as follows: the particular dicarboxylic acid, dicarboxylic acid with protected amino group or, where applicable, dicarboxylic acid protected on a one carboxylic group, is dissolved in a suitable solvent that allows to remove the remaining water, preferably in benzene or toluene, most preferably in benzene. Whereupon after the removal of water by a partial distillation of the solvent, the reaction mixture which is prevented against the water supply in an appropriate manner known in the scope of technique, cooled down to room temperature and under the inert atmosphere is slowly added condensing agent, preferably DCC, and a solution of compound formula II in a suitable solvent, preferably in an aromatic hydrocarbon, advantageously in benzene or toluene, most preferably in benzene, in the presence of a catalytic agent, preferably DMAP. This reaction mixture is stirred 10-48 hours, preferably overnight, at temperatures from 0 to 50° C., preferably at room temperature. The next day the mixture is poured into saturated sodium bicarbonate, preferably aqueous $NaHCO_3$ or $KHCO_3$, and the product is extracted with an organic solvent, in which is well soluble, for example, with advantage, ethyl acetate. Collected organic phases are washed with water to remove sodium bicarbonate. Precipitated N,N'-dicyclohexylurea is filtered off and the filtrate is dried over drying agent, preferably magnesium sulfate or sodium sulfate, most preferably sodium sulfate and the solvent evaporated, preferably under vacuum. The obtained product is purified, where appropriate, with the advantage by a chromatography on a column of silica gel to afford the compound of general formula I, where $R^1$ represents the group of the general formula $R^3OOC—R^2—CO—$ and $R^2$ represents alkyl or alkenyl group with 1 to 18 carbon atoms in a straight or a branching carbon chain, which may be substituted by one or several halogen atoms and by amino group, which is protected by a group that allows deprotection. $R^3$ represents a protecting group for carboxyl groups, preferably benzyl group.

In case that $R^3$ means benzyl protecting group in compound of formula I required removing of this protecting group is realized so that the obtained compound is dissolved in a suitable solvent, preferably alcohol, most preferably in methanol, and to this solution a hydrogenation catalyst is added, preferably $Pd/CaCO_3$. After the hydrogenation, the catalyst is filtered off and the solvent is evaporated to afford the product of general formula I in which $R^1$ represents the group of general formula $R^3OOC—R^2—CO—$, where $R^2$ means alkyl or alkenyl group with 1 to 18 carbon atoms in a straight or a branching carbon chain, which may be substituted by one or several halogen atom and amino group, which is protected by a group that allows deprotection. $R^3$ represents a hydrogen atom.

When the compound of general formula I was obtained in which $R^1$ represents the group of general formula $R^3OOC—R^2—CO—$, $R^2$ represents alkyl or alkenyl group with 1 to 18 carbon atoms in a straight or a branching carbon chain which may be substituted by one or more halogen atoms and amino group, which is protected by a removable group, and $R^3$ represents a hydrogen atom and has an amino group, which is protected by a removable group, the deprotection of amino groups is accomplished in the next step so that the compound is dissolved in an organic solvent, preferably in methylene chloride and trifluoroacetic acid is added. Then, the reaction mixture is allowed to react from 0.1 to 48 hours, preferably 16 hours at temperatures from 0° to 50° C., preferably at room temperature. When the solvent is removed, the residue is dissolved in an organic solvent, preferably in methanol, then pyridine is added and the mixture is evaporated to dryness to obtain the product of general formula I, where $R^1$ represents the group of general formula $R^3OOC—R^2—CO—$, where $R^2$ means alkyl or alkenyl group with 1 to 18 carbon atoms in a straight or a branching carbon chain, which may be substituted by one or more halogen atoms and amino group; and $R^3$ represents a hydrogen atom.

When $R^2$ of compound of the general formula I contains a heterocyclic group, as for example in the compound of formula HET;

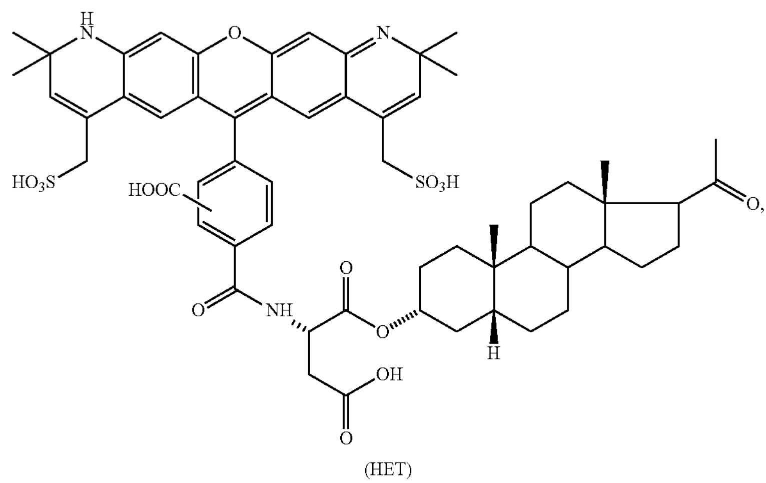

such heterocyclic group can be introduced into a molecule of general formula I, for example, by the reaction of activated carboxyl group with amino substituent on the alkyl chain $R^2$. Carboxyl group may be functionalized with an activating group (for example with hydroxybenzotriazole, substituted hydroxybenzotriazole, HATU group, TATU group and advantageously TSTU group in the form of succinimidylester). This ester reacts with the compound of general formula I in which $R^2$ means alkyl group substituted with amino group so the compound of general formula I is obtained, in which $R^2$ represents alkyl group substituted with amino group that is substituted with the heterocyclic group of HET.

The person skilled in the art can analogously prepare similar compounds of general formula I, in which $R^2$ means as given above.

Thiocompounds and amides can be prepared by analogous procedures from the compounds of general formula I, where R means atom of sulfur (as describe for instance Swan, Turnbull, Tetrahedron 22, 1966, p. 231), or if appropriate nitrogen atom (as describe for instance Schmitt J., Panouse J. J., Hallot A., Pluchet H., Comoy P.: Bull Soc. Chim. France 1962, p. 1846).

Another subject of this invention is application of compounds of general formula I, where $R^1$ means as described before for production of therapeutics for treatment of neuropsychiatric disorders related to dysbalance of glutamatergic neurotransmitter system, especially ischemic CNS injury, neurodegenerative changes and disorders, mood disorders, depression, post-traumatic stress disorder and other stress-related disorders, anxiety, schizophrenia and other psychotic illnesses, pain, addiction, multiple sclerosis, epilepsy and gliomas.

Various structural modifications of our invented compounds of general formula I have shown only minimal differences in their biological activity; these findings are congruent with previous electrophysiological results using patch-clamp technique and assessing binding kinetics of these compounds on the NMDA receptors. Therefore, we have chosen a representative molecule of pregnanolone glutamate from example 9 [next: compound from Example 9, compound of a general formula I, in which $R^1$ is —$CH(NH_2)$—$(CH_2)_2$—COOH group], which was subjected to detailed examination in relation to its neuroprotective action on the hippocampal lesions (by means of NMDA; compound from Example 9). We have also studied its effects on behavior after separate application and its comparison with the model molecule (dizocilpine), which is known to exert neuroprotective properties in certain preclinical configurations, but wealth of evidence from animal models and occasional observations in humans suggest that it posses pronounced psychotomimetic side-effects.

The compound from example 9 penetrates blood brain barrier and rapidly enter the brain ($T_{max}$=60 min, $c_{max}$=508 ng/whole brain) after i.p injection (dose 1 mg/kg) and exponentially decreases to a mean of 222 ng/whole brain after 2 hours, 128 ng/whole brain after 3 hours, 14 ng/whole brain after 24 hours and 0.6 ng/whole brain after 48 hours. It seems that the compound from example 9 is eliminated by a first-order process and it is not cumulated in brain tissue. Next its $c_{max}$=675 ng/ml in plasma at the time of $T_{max}$=15 min was detected. The following pharmacokinetics parameters have been estimated for plasma: $K_e$=0.002593; $T_{1/2}$=267 min; $AUC0\_inf_{i.p.}$=75348.

Subsequent toxicological study showed absense of any signs of acute toxicity in laboratory rat of the compound from example 9.

Moreover next studies demonstrated absence of hyperlocomotion, deficit in sensorimotor gating and cognitive deficit, the side effects typical for noncompetitive NMDA antagonist.

Examples of biological activities indicate possibilities to block excessive effect of glutamate in broad spectrum of in animal models of CNS disorders. The compound from example 9 showed neuroprotective effect in animal models of brain damage induced by hypoxic/ischemic state and by neurotoxic lesion by bilateral injection of NMDA into the dorsal hippocampus. Further the examples documents slight anxiolytic effect and improving of cognition deficit in models schizophrenia-like behavior. The compound from example 9 exhibits antidepressant properties in extensive tests of depression and stress too. The examples have proven analgetic and anticonvulsive properties of compound from example 9 in addition.

The data confirm capability of NMDA receptor antagonists to prevent the excessive release of glutamate and subsequent damage of the CNS leading to deterioration of behavior. From the clinical point of view; however, their therapeutic potential is rather limited. Regarding the fact that their application leads to wide variety of side effects, ranging from motor impairment to induction of psychotic symptoms.

Main advantage of 3αC substituted analogues of pregnanolone, use-dependent NMDA antagonists, constitutes absence of serious side effect typical for competitive NMDA antagonists, while retaining their therapeutic activities.

Biological Activity of the Invented Compounds on Cell Cultures 5-10-day old hippocampal culture cells of HEK293 cultured cells were used for electrophysiological investigations with a latency of 16-40 h after transfection. Whole-cell currents were measured by patch-clamp amplifier after capacitance and serial resistance. Steroid-containing solutions were prepared from fresh solution (20 mM) of steroid dissolved in dimethyl-sulfoxide (DMSO). Same concentrations of DMSO were used in all extracellular solutions. Control and experimental solutions were applied via microprocessor-controlled perfusion system with approx. rate of solution exchange in areas adjacent to cells reaching ~10 ms.

The results show that synthetic analogues of pregnanolone sulphate have the same mechanism of action on NMDA receptors as pregnanolone sulphate; however, they differ in their affinity for these receptors.

BRIEF DESCRIPTION OF THE FIGURES

FIG. 2 Bottom panel: Prepulse inhibition of the acoustic startle reflex (according to example 29) was not significantly altered by application of the compound from Example 9.

FIGS. 16A-D show the growth effect of the compound from example 9 on glioma cells in culture according to Example 43. FIGS. 16A and 1613 represent control groups of C6 glioma cell lines administered by cholesterol at doses of 0.1 and 1 μg dissolved in 50 ml of β-cyclodextrine solution after 3+1 and 3+3 days of cultivation in vitro (DIV) respectively.

At x-axis first column represents group of control animals and second column group of animals injected i. p. with drug from example 9 at dose 10 mg/kg.

Figure 19:
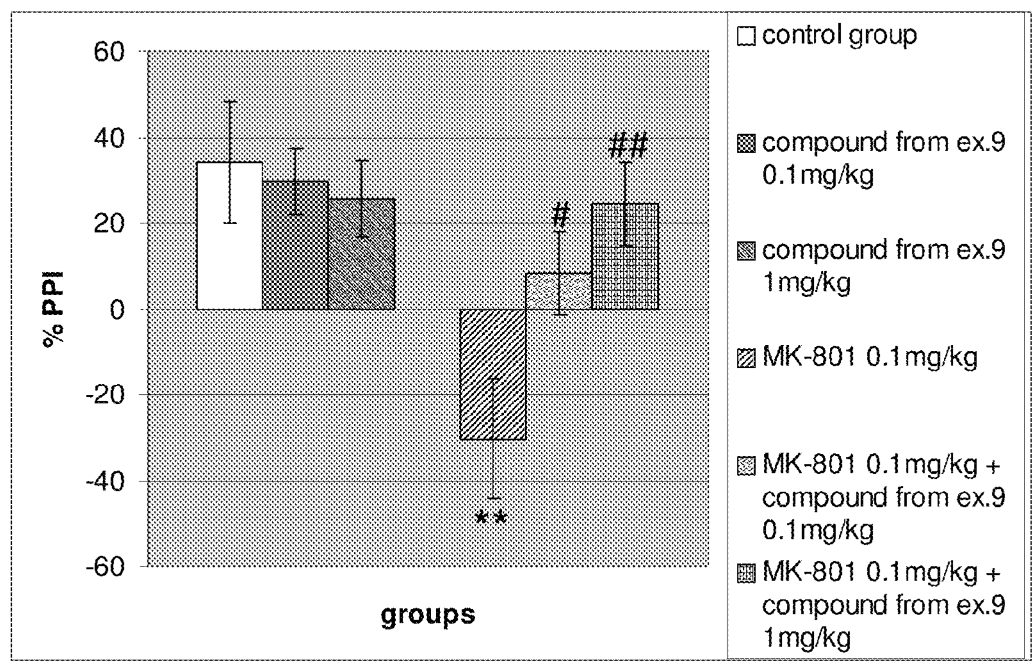

FIG. 19 visualizes effect of compound from example 9 on prepulse inhibition (PPI) of the startle response in an animal model of schizophrenia according to Example 46. At the y-axis % of PPI are outlined. At the x-axis columns represents group of animals: first column: control group, second and third column: group of animals treated by compound from ex. 9 in doses of 0.1 mg/kg of b.w. and 1 mg/kg of b.w. respectively; fourth column: group of animals receiving MK-801 (0.1 mg/kg of b.w.), fifth and sixth column: group of animals receiving compound from ex. 9 (0.1 mg/kg or 1 mg/kg of b.w.) in combination with MK-801 (0.1 mg/kg of b.w.).

Figure 20:
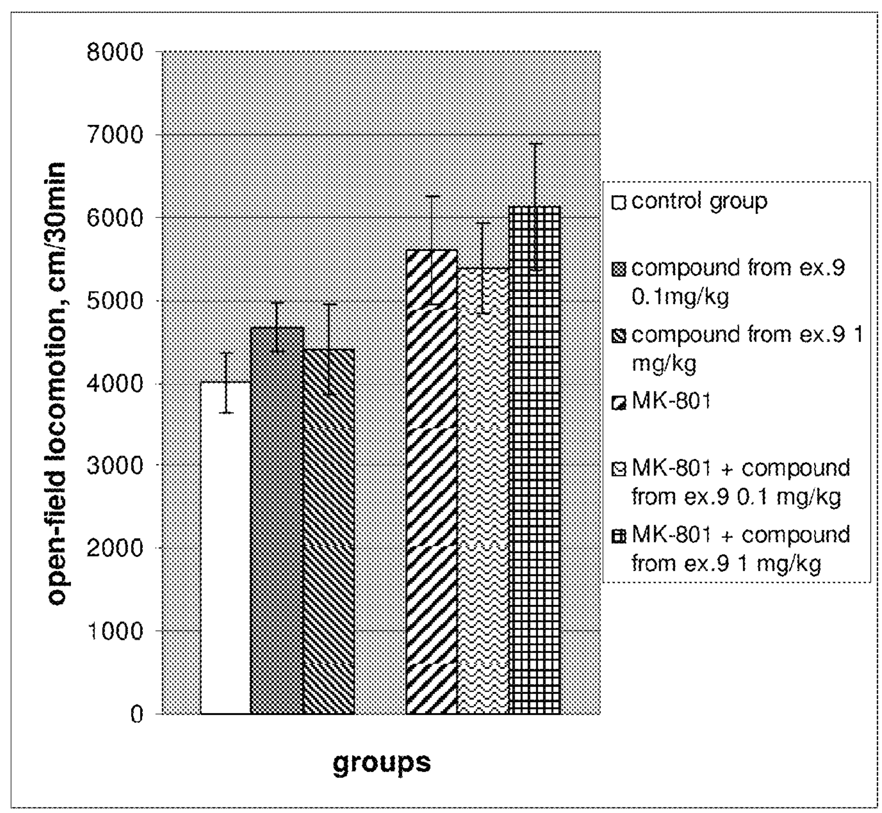

FIG. 20 shows the effect of compound from example 9 alone or in combination with MK-801 on the locomotion in the open-field behavior according to Example 47. At the y-axis total distance in cm traveled during 30 min in a box is outlined. At the x-axis columns represents group of animals: first column: control group, second and third column: group of animals treated by compound from ex. 9 in doses of 0.1 mg/kg of b.w. and 1 mg/kg of b.w. respectively; fourth column: group of animals receiving MK-801 (0.1 mg/kg of b.w.), fifth and sixth column: group of animals receiving compound from ex. 9 (0.1 mg/kg or 1 mg/kg of b.w. resp.) in combination with MK-801 (0.1 mg/kg of b.w.).

Figure 21:
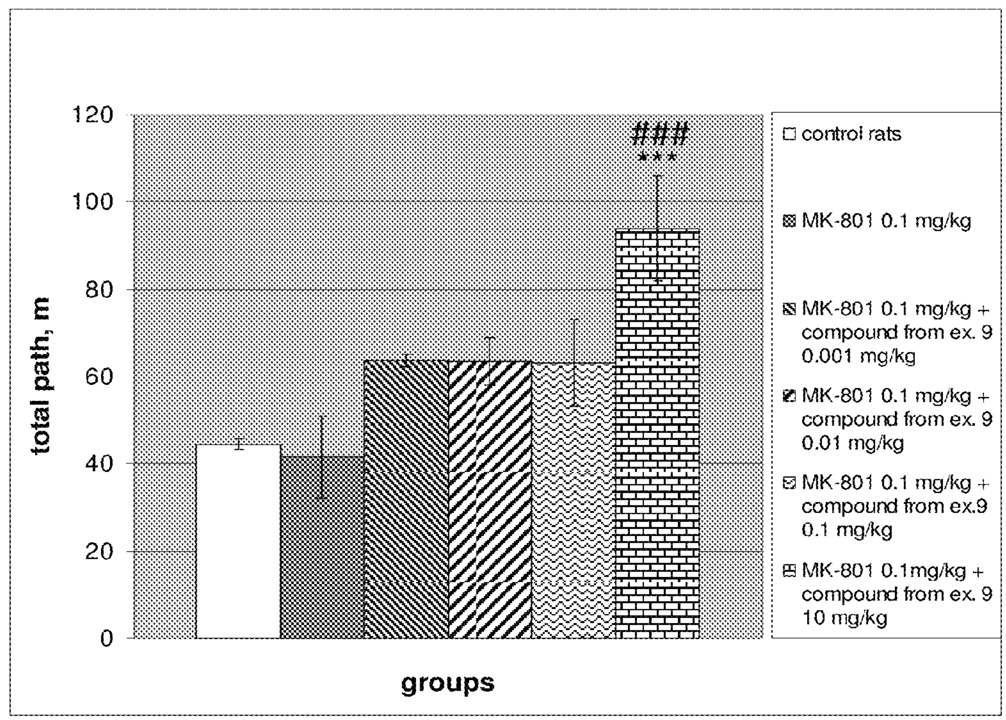

FIG. 21 shows the effect of the compound from example 9 on the locomotor activity in the final session of the 4-day AAPA training according to Example 48. At the y-axis total distance (in meters) travelled in the arena is outlined. At the x-axis columns represents group of animals, from left to right are outlined groups receiving saline, MK 801 (0.1 mg/kg of b.w.), MK 801 (0.1 mg/kg)+compound from ex. 9 (0.001 mg/kg), MK 801 (0.1 mg/kg)+compound from ex. 9 (0.01 mg/kg), MK 801 (0.1 mg/kg)+compound from ex. 9 (0.1 mg/kg), MK 801 (0.1 mg/kg)+compound from ex. 9 (10 mg/kg). ### indicates $p<0.001$ compared to controls. Statistic differences were evaluated in last session where asymptotic level of performance is reached by controls.

Figure 22:
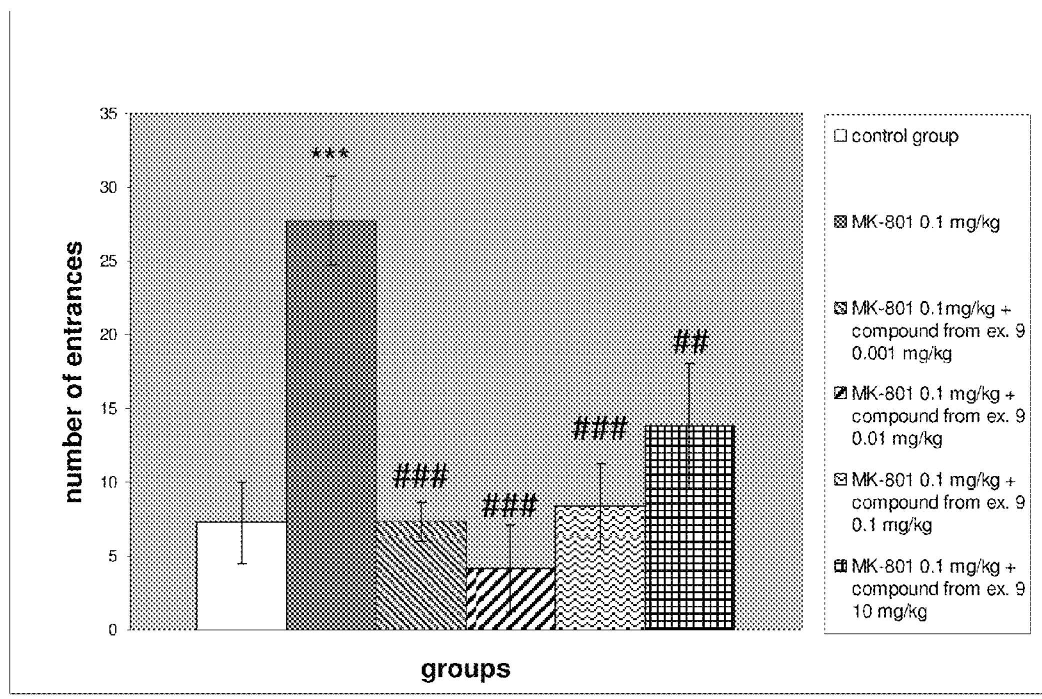

FIG. 22 shows the effect of the compound from example 9 on the dizocilpine-induced avoidance deficit according to example 49. At the y-axis number of entrances to shock sector is outlined. At the x-axis columns represents group of animals, from left to right are outlined groups receiving saline, MK 801 (0.1 mg/kg of b.w.), MK 801 (0.1 mg/kg)+compound from ex. 9 (0.001 mg/kg), MK 801 (0.1 mg/kg)+compound from ex. 9 (0.01 mg/kg), MK 801 (0.1 mg/kg)+compound from ex. 9 (0.1 mg/kg), MK 801 (0.1 mg/kg)+compound from ex. 9 (10 mg/kg). * indicates significant difference compared to controls ($p<0.05$), ## $p<0.01$ and ### $p<0.001$. Statistic differences were evaluated in last session where asymptotic level of performance is reached by controls.

Figure 23:
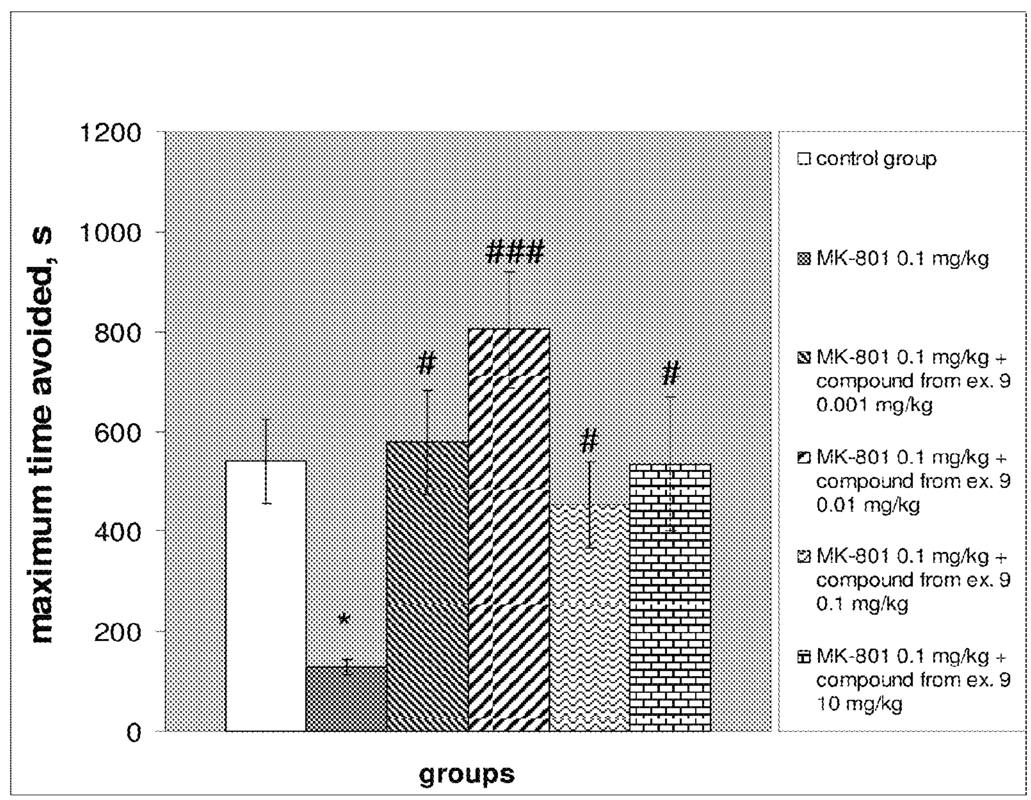

FIG. 23 shows the maximum time of avoidance as a measure of cognitive functions in the final session of the 4-day AAPA task training according to Example 50. At the y-axis maximum time avoided in seconds is outlined. At the x-axis columns represents group of animals, from left to right are outlined groups receiving saline, MK 801 (0.1 mg/kg of b.w.), MK 801 (0.1 mg/kg)+compound from ex. 9 (0.001 mg/kg), MK 801 (0.1 mg/kg)+compound from ex. 9 (0.01 mg/kg), MK 801 (0.1 mg/kg)+compound from ex. 9 (0.1 mg/kg), MK 801 (0.1 mg/kg)+compound from ex. 9 (10 mg/kg). * indicates significant difference compared to controls $p<0.05$; # $p<0.05$ and ### $p<0.001$ compared to MK-801 group. Statistic differences were evaluated in last session where asymptotic level of performance is reached by controls.

Figure 24:
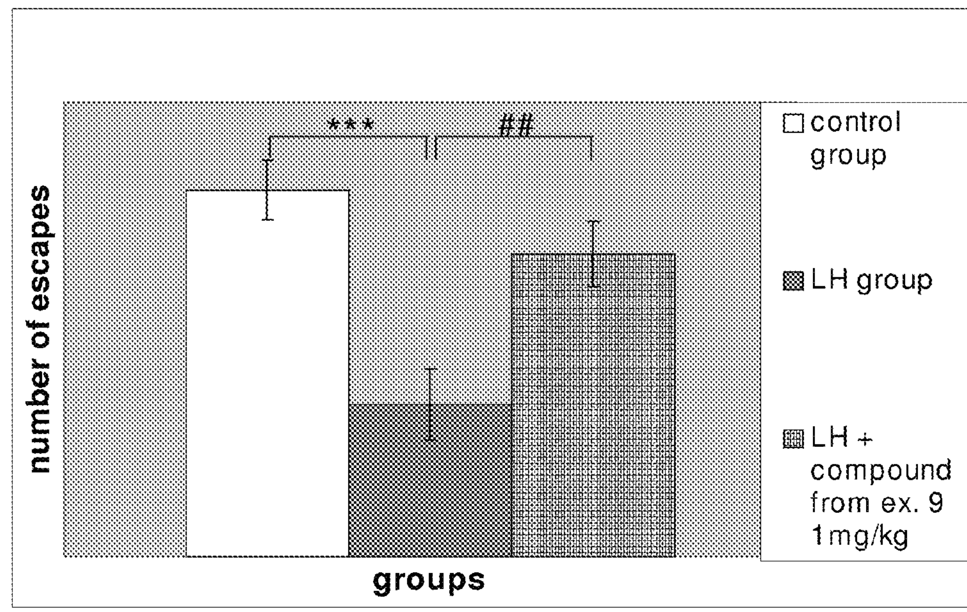

FIG. 24 shows the effect of compound from Example 9 on the learned helplessness model of affective disorders according to Example 51. At the y-axis number of escapes is outlined. At the x-axis first column represents group of control animals, second column group of animals from learned helplessness group received no drug and third column group of animals from learned helplessness group received compound from ex. 9 (1 mg/kg of b.w.). ***indicates $p<0.001$ compared to control group and ## $p<0.01$, compared to LH group.

Figure 25:
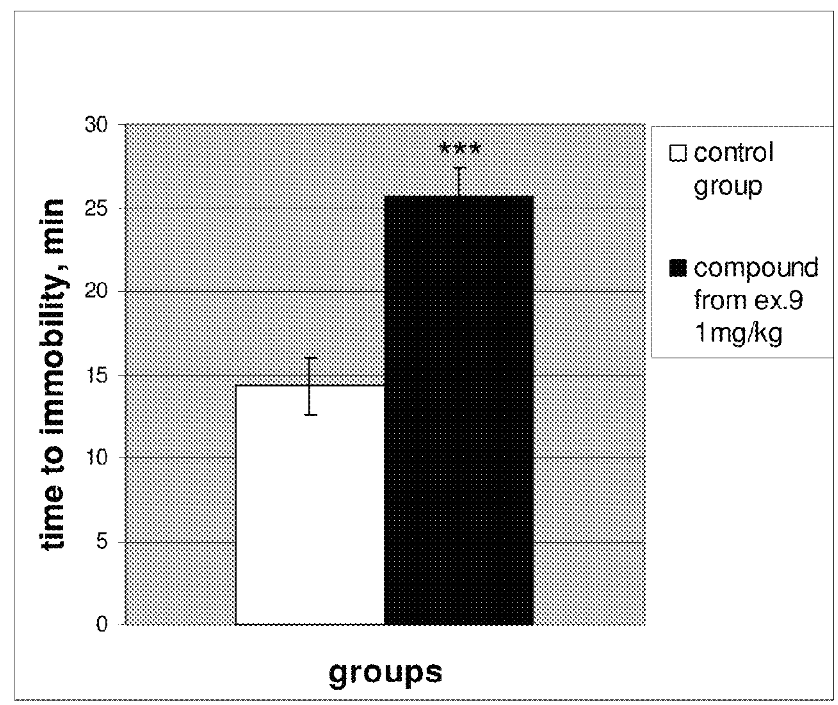

FIG. 25 shows the effect of compound from Example 9 on time to immobility in Forced swimming test according to Example 52. At the y-axis the time to immobility in minutes is outlined. At the x-axis first column represents group of control animals, second column group of animals receiving compound from ex. 9 (1 mg/kg of b.w.). *** indicates $p<0.001$, compared to control group.

Figure 26:
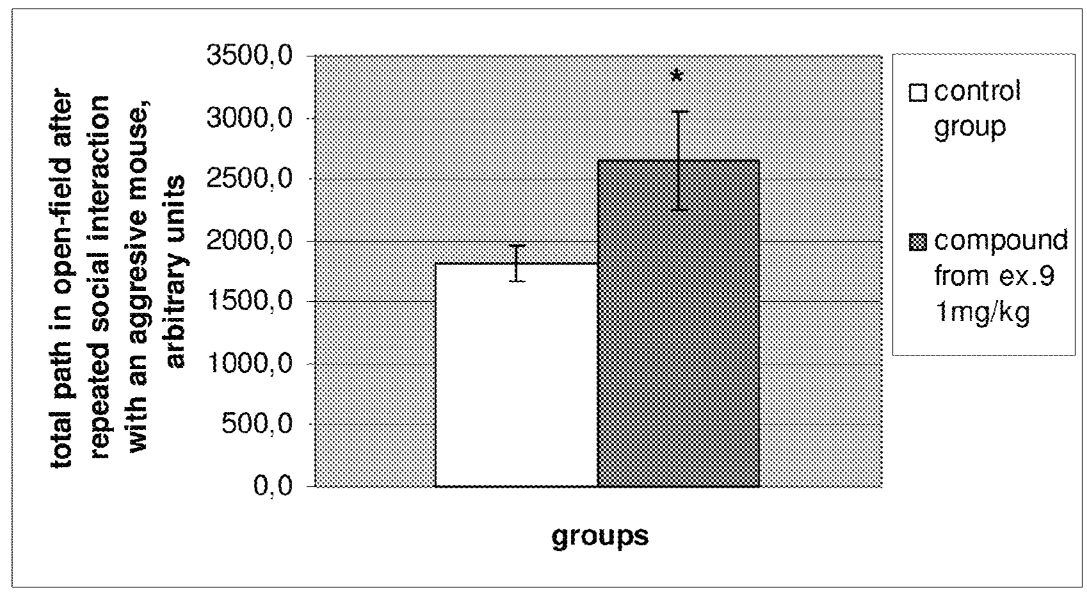

FIG. 26 shows the effect of compound from example 9 on depression-like behavior induced by social defeat in mice according to Example 53. At the y-axis the total path in open-field after repeated social interaction with an aggressive mouse in arbitrary units is given. At the x-axis first column represents group of control animals, second column group of animals receiving compound from ex. 9 (1 mg/kg of b.w.). * indicates $p<0.05$ compared to controls.

Figure 27:
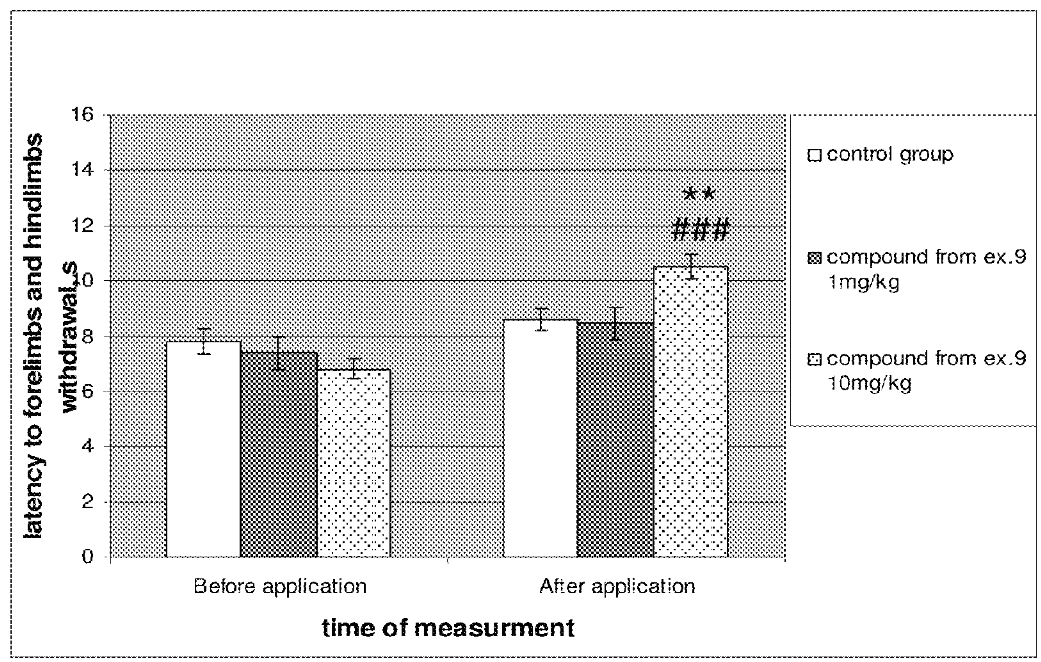

FIG. 27 shows the effect of compound from Example 9 on the pain-induced limb reaction according to Example 54. At the y-axis the limbs withdrawal latency in seconds is given. At the x-axis first column represents group of control animals, second and third columns groups of animals receiving compound from ex. 9 (1 mg/kg and 10 mg/kg of b.w. resp.) before application of thermal stimulation and after that. ** indicates $p<0.05$ compared to controls, ### $p<0.001$ compared to compound from ex. 9 in dose 10 mg/kg "before".

Figure 28:
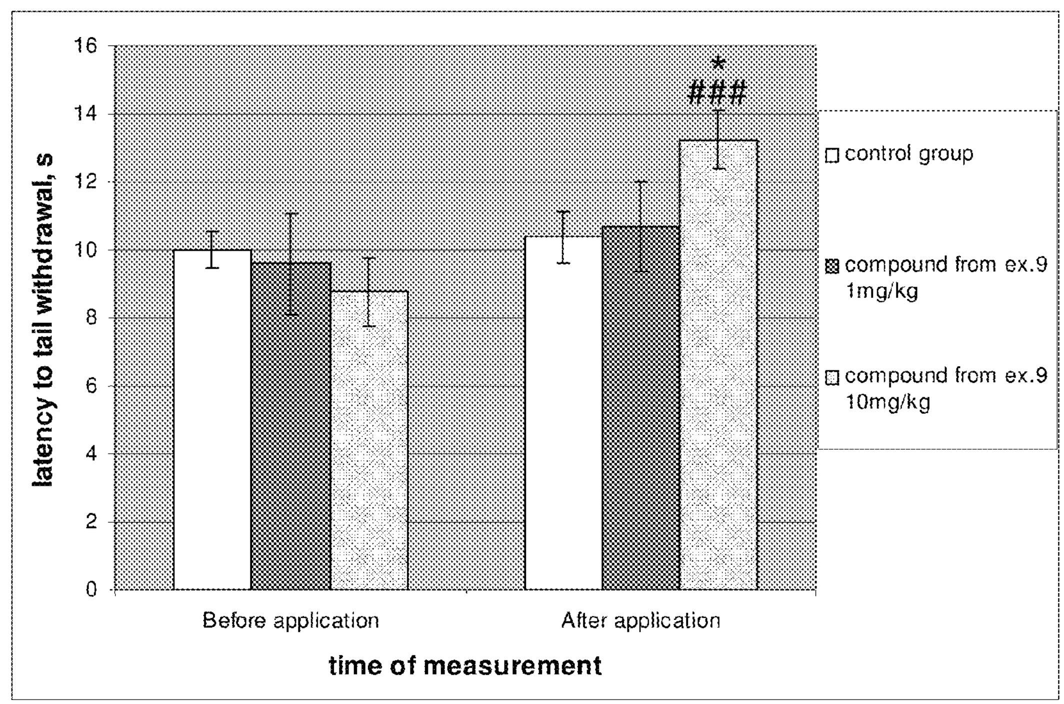

FIG. 28 shows the effect of compound from Example 9 on the pain-induced tail reaction according to Example 54. At the y-axis the tail withdrawal latency in seconds is given. At the x-axis first column represents group of control animals, second and third columns groups of animals receiving compound from ex. 9 (1 mg/kg and 10 mg/kg of b.w. resp.) before application of thermal stimulation and after that. * indicates $p<0.05$ compared to controls, ### $p<0.001$ compared to compound from ex. 9 in dose 10 mg/kg "before".

Figure 29:
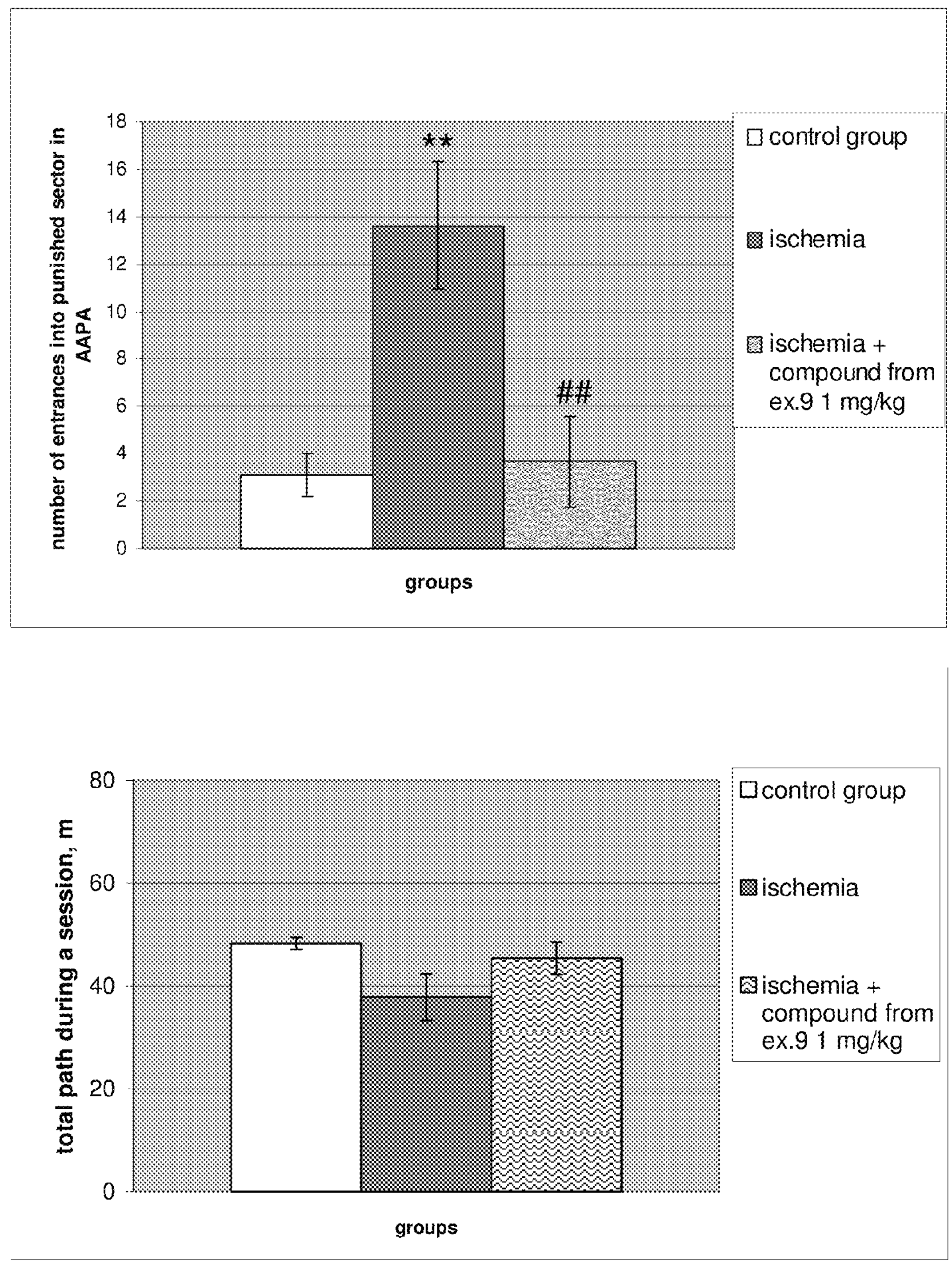

FIG. 29 shows the effect of compound from example 9 on cognitive coordination and motor activity according to Example 55.

FIG. 29, upper graph demonstrates at the y-axis number of entrances into punished sector in AAPA. At the x-axis first column represents group of control animals, second and third columns groups of ischemic animals without medication and receiving compound from ex. 9 (1 mg/kg of b.w.) respectively. **indicates $p<0.01$ compared to control rats, ## indicates $p<0.01$ compared to ischemic rats.

FIG. 29, lower graph demonstrates at the y-axis total path elapsed during a session in AAPA (metres). At the x-axis first column represents group of control animals, second and third columns groups of ischemic animals without medication and receiving compound from ex. 9 (1 mg/kg of b.w.) respectively.

Figure 30:
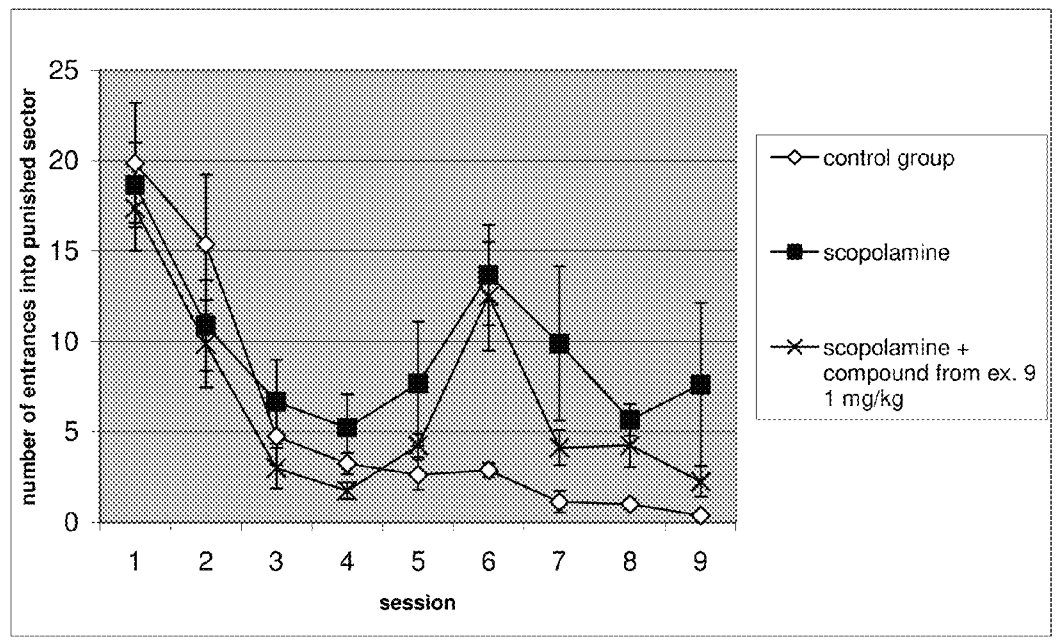

FIG. 30 represents chart showing the effect of compound from example 9 on the scopolamine-induced cognitive deficit according to Example 56. At the y-axis the number of entrances into punished sector is given. At the y-axis the time course in days is outlined (symbol -♦- for control group, symbol -■- for group receiving scopolamine and symbol -▲- for group receiving compound from exp. 9 (1 mg/kg of b.w.)+ scopolamine.

Figure 31:
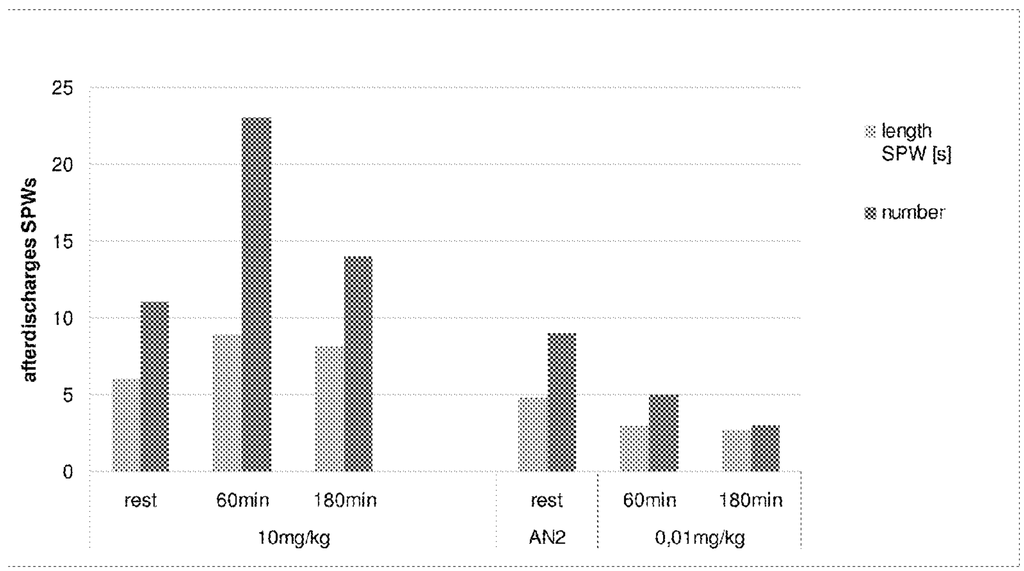

FIG. 31 shows the effect of compound from example 9 on the epileptic afterdischarges elicited by stimulation of the rat somatosensory areas according to Example 57 at intervals 60 min and 180 min after application of above mentioned compound. At the y-axis length (in seconds) and number of spike and wave afterdischarges is depicted. At the x-axis three pairs of columns (one column for length and second for a number of SWP) on the left side of chart stands for a dose of 10 mg/kg, three pairs of columns in the right stands for a dose 0.01 mg/kg of b.w. respectively).

Figure 32:
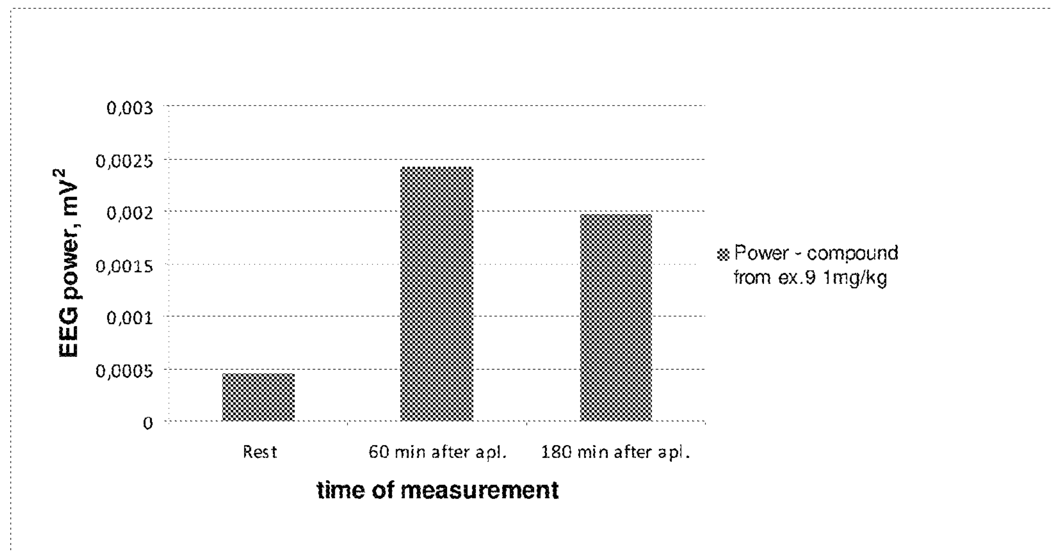

FIG. 32 shows the effect of compound from example 9 on the spontaneous EEG power according to Example 57 measured at intervals 60 min and 180 min after application. At the y-axis the EEG power in $mV^2$ is depicted, columns at x-axis represent measurements executed before the medication of compound from example 9 and 60 or 180 minutes after injection of compound from ex. 9 (1 mg/kg of b.w.).

EXAMPLES

Example 1

Synthesis of 20-Oxo-5β-pregnan-3α-yl (2S)-4-(benzyloxy)-2-[(tert-butoxycarbonyl)amino]-4-oxobutanoate The compound II (320 mg, 1 mmol) and Boc-Asp(OBzl)-OH (345 mg, 1.1 mmol) were dissolved in freshly dried benzene (35 mL). Then, about 6 mL of benzene was evaporated.

4-Dimethylaminopyridine (4 mg) and dicyclohexylcarbodiimide (550 mg, 2.18 eq.) were added in dry benzene (3 mL) at room temperature under inert atmosphere and the reaction mixture was stirred overnight. The reaction mixture was poured into saturated aqueous $NaHCO_3$ (40 mL), the product was extracted with EtOAc (3×30 mL) and the collected organic phases were washed 2× with water (10 mL). Precipitated N,N'-dicyklohexylurea was filtered off, the filtrate was dried over $Na_2SO_4$ and the solvent was evaporated under vacuum. Another portion of N,N'-dicyklohexylurea was crystallised from ether, filtered off and the filtrate containing desired product was evaporated. The residue was purified on a column of silica gel (20 g) in a mixture of PeAe-$Et_2O$ (9:1) to afford white foam (582 mg; 93%), $[\alpha]_D$=+82 (c 0.36, $CHCl_3$). $^1$H NMR (400 MHz, $CDCl_3$): δ 0.60 (s, 3H, H-18); 0.92 (s, 3H, H-19); 1.45 (s, 9H, t-Bu); 2.12 (s, 3H, H-21); 2.52 (t, 1H, $J_1$=8.9, H-17); 2.88 (dd, 1H, $J_1$=16.8, $J_2$=4.5, H-3b'); 3.03 (bdd, 1H, $J_1$=16.8, $J_2$=4.5, H-3a'); 4.50-4.55 (bm, 1H, CH-2'); 4.71-4.79 (m, 1H, H-3); 5.10-5.17 (m, 2H, H-benzyl); 5.48 (bd, 1H, $J_1$=8.6, HN); 7.32-7.37 (m, 5H, phenyl). $^{13}$C NMR (100 MHz, $CDCl_3$): δ 13.40 (C-18); 20.82; 22.87; 23.23; 24.38; 26.25; 26.32; 26.82; 28.30 ($CH_3$-Boc); 31.53; 31.98; 34.57; 34.89; 35.74; 36.94; 39.14; 40.38; 41.77; 44.29; 52.88; 56.62; 63.84; 66.71; 75.89; 80.02 (C-Boc); 128.31 (Ar); 128.38 (Ar); 128.55 (Ar); 135.42 (Ar); 155.36 (CO-Boc); 170.35, 170.70 (C-1', C-4'); 209.60 (C-20). IR ($CHCl_3$): 3438 (N—H, amide), 1732 (C═O, aspartate), 1702 (C═O, $COCH_3$, NHBoc), 1499 (N—H, amide), 1232 (C—O, aspartate), 1166 (NHBoc), 1455 (ring), 1368 (t-Bu). For $C_{37}H_{53}NO_7$ (623.8) calculated: 71.24% C, 8.56% H, 2.25% N; found: 71.40% C, 8.70% H, 2.18 N %.

Example 2

20-Oxo-5β-pregnan-3α-yl N-(tert-butoxycarbonyl)-L-aspartyl 1-ester

The compound obtained in the previous Example 1 (565 mg, 0.906 mmol) was dissolved in absolute MeOH (7 ml) and 5% Pd/$CaCO_3$ (56 mg) was added. The reaction was completed after an eight-hour hydrogenation under vigorous stirring and moderate hydrogen overpressure (10 mbar). The catalyst was filtered off and the solvent was evaporated. Then, the product was dissolved in ether and again evaporated to afford white foam (484 mg, 100%), $[\alpha]_D$ +87.0 (c 0.49, $CHCl_3$). $^1$H NMR (400 MHz, $CD_3OD$): δ 0.60 (s, 3H, H-18); 0.92 (s, 3H, H-19); 1.45 (s, 9H, t-Bu-O); 2.12 (s, 3H, H-21); 2.52 (t, 1H, $J_1$=8.9, H-17); 2.63-2.67 (m, 2H, H-3a',3b'); 4.45 (t, 1H, H-2'); 4.65-4.73 (m, 1H, H-3). $^{13}$C NMR (100 MHz, $CDCl_3$): δ 13.40 (C-18); 20.83; 22.88; 23.25; 24.40; 26.26; 26.39; 26.86; 28.30 ($CH_3$-Boc); 31.51; 32.00; 34.60; 34.91; 35.76; 36.61; 39.13; 40.39; 41.80; 44.33; 49.99; 56.63; 63.86; 76.05; 80.24 (C-Boc); 155.45 (OCONH); 170.31 (C-1'); 175.22 (COOH); 209.83 (C-20). IR ($CHCl_3$): 3439 (N—H), 1742 (C═O, aspartate, COOH, monomer), 1715 (C═O, COOH, dimer), 1703 (C═O, $COCH_3$, NHBoc), 1500 (C—N, amide), 1369 (t-Bu-O), 1235 (C—O, aspartate), 1194 (C—O, aspartate), 1161 (NHBoc). For $C_{30}H_{47}NO_7$ (533.7) calculated: 67.51% C, 8.88% H, 2.62% N; found: 67.90% C, 9.01% H, 2.55% N.

Example 3

20-Oxo-5β-pregnan-3α-yl L-aspartyl 1-ester

Trifluoroacetic acid (1 mL, 13.4 mmol, 15.5 eq.) was added dropwise to a stirred solution of the compound obtained in the previous Example 2 (465 mg, 0.871 mmol) in dichloromethane (10 mL). The reaction mixture was stirred for 2 h at room temperature and then it was allowed to stand overnight at 5° C. Then, it was evaporated 3 times with benzene; residue was dissolved in a mixture of pyridine (1 mL) and MeOH (1 mL), solvents were again evaporated, the residue dissolved in chloroform and washed with water. Organic phase was dried over $Na_2SO_4$ and the solvent was evaporated under vacuum. Oily residue was dissolved in ether and the solvent was evaporated to afford white foam (370 mg, 98%), $[\alpha]_D$ +132 (c 0.11, MeOH—$CHCl_3$ 1:1). $^1$H NMR (400 MHz, $CDCl_3$): δ 0.60 (s, 3H, H-18); 0.94 (s, 3H, H-19); 2.12 (s, 3H, H-21); 2.56 (t, 1H, $J_1$=8.8, H-17); 2.77 (dd, 1H, $J_1$=17.0, $J_2$=8.1, H-3b'); 2.88 (bd, 1H, $J_1$=17.0, H-3a'); 4.00-4.07 (bm, 1H, H-2'); 4.78-4.86 (bm, 1H, H-3). $^{13}$C NMR (100 MHz, $CDCl_3$-$CD_3OD$ 1:1): δ 13.02 (C-18); 20.55; 22.53; 22.86; 24.08; 25.96; 26.01; 26.58; 31.14; 31.65; 34.31; 34.55; 35.50; 35.68; 38.75; 40.12; 41.58; 44.17; 50.44; 56.34; 63.57; 76.60; 169.21 (C-1'); 174.04 (COOH); 210.97 (C-20). IR (KBr): 2121 ($NH_3^+$), 1746 (C═O, aspartate), 1707 (C═O, $COCH_3$), 1616 ($COO^-$), 1215 (C—O, aspartate). For $C_{25}H_{39}NO_5$ (433.5) calculated: 69.25% C, 9.07% H, 3.23% N; found: 69.01% C, 9.23% H, 3.05% N.

The title compounds of the following Examples 4 to 12 were prepared according to the above-mentioned procedures of compounds that are listed at the beginning of each example.

Example 4

20-Oxo-5β-pregnan-3α-yl(3S)-4-(benzyloxy)-3-[(tert-butoxycarbonyl)amino]-4-oxobutanoate Treatment of compound II (1 mmol) and Boc-Asp(OBzl) (1.1 mmol) afforded the title compound according to the procedure described in Example 1, $[\alpha]_D$ +92.5 (c 0.24). $^1$H NMR (400 MHz, $CD_3OD$): 0.59 (s, 3H, H-18); 0.92 (s, 3H, H-19); 1.44 (s, 9H, t-Bu); 2.11 (s, 3H, H-21); 2.53 (t, 1H, $J_1$=8.8, H-17); 2.79 (dd, 1H, $J_1$=16.8; $J_2$=4.6, H-3b'); 2.98

(bdd, 1H, $J_1$=16.8; $J_2$=4.6, H-3a'); 4.60-4.65 (bm, 1H, CH-2'); 4.64-4.73 (m, 1H, H-3); 5.13-5.23 (m, 2H, $CH_2$-benzyl); 5.50 (bd, 1H, $J_1$=8.8 HN); 7.30-7.36 (m, 5H, phenyl). IR ($CHCl_3$): 3439 (N—H, amide), 1717 (C═O, aspartate), 1703 (C═O, $COCH_3$, NHBoc), 1499 (N—H, amide), 1455 (ring), 1380 (t-Bu), 1163 (C—O, NHBoc). For $C_{37}H_{53}NO_7$ (623.8) calculated: 71.24% C, 8.56% H, 2.25 N; found: 70.91% C, 8.74% H, 2.52% N.

Example 5

20-Oxo-5β-pregnan-3α-yl-N-(terc-butoxycarbonyl)-L-aspartyl 4-ester

The compound from previous Example 4 afforded the title compound following the similar work-up as described in Example 2: $[\alpha]_D$ +96.3 (c 0.20). $^1$H NMR (400 MHz, $CD_3OD$): δ 0.60 (s, 3H, H-18); 0.93 (s, 3H, H-19); 1.46 (s, 9H, t-Bu); 2.11 (s, 3H, H-21); 2.52 (t, 1H, $J_1$=8.9, H-17); 2.81 (dd, 1H, $J_1$=17.0; $J_2$=5.2H-3b'); 3.00 (dd, 1H, $J_1$=16.9; $J_2$=4.7H-3a'); 4.56-4.64 (m, 1H, H-2'); 4.70-4.82 (m, 1H, H-3), 5.55 (d, 1H, J=7.9, FIN). IR ($CHCl_3$): 3439 (amide), 1716 (C═O), 1703 (C═O, $COCH_3$, NHBoc), 1501 (amide), 1386 (t-Bu), 1232 (N—H, aspartate), 1193 (N—H, aspartate), 1160 (NHBoc). For $C_{30}H_{47}NO_7$ (533.7) calc.: 67.51% C, 8.88% H, 2.62% N; found: 67.25% C, 9.15% H, 2.90% N.

Example 6

20-Oxo-5β-pregnan-3α-yl L-aspartyl 4-ester

The compound from the previous Example 5 afforded the title compound following the work-up as described in Example 3, $[\alpha]_D$ +91.5 (c 0.24, MeOH—$CHCl_3$ 1:1). $^1$H NMR (400 MHz, $CDCl_3$): 0.60 (s, 3H, H-18); 0.95 (s, 3H, H-19); 2.12 (s, 3H, H-21); 2.54 (m, 3H, H-17); 2.86-3.08 (bm, 2H, H-3b', H-3a'); 3.86-3.98 (bm, 1H, H-2'); 4.72-4.80 (bm, 1H, H-3); 8.00 (s, 1H, HN). IR ($CHCl_3$): 1721 (C═O, aspartate), 1702 (C═O, $COCH_3$). ESI neg MS: 432.3 (100%, M−1), 415.4 (10%, M−18). For $C_{25}H_{39}NO_5$ (433.5) calculated: 69.25% C, 9.07% H, 3.23% N; found: 69.25% C, 9.15% H, 3.54% N.

Example 7

20-Oxo-5β-pregnan-3α-yl (2S)-5-(benzyloxy)-2-[(terc-butoxycarbonyl)amino]-5-oxopentanoate Treatment of the compound II (1 mmol) and Boc-Glu (OBzl)-OH (1.1 mmol) afforded the title compound following the procedure descrided in Example 1, $[\alpha]_D$ +70.9 (c 0.35). $^1$H NMR ($CDCl_3$): δ 0.60 (s, 3H, $CH_3$-18); 0.93 (s, 3H, H-19); 1.44 (s 9H, t-Bu); 2.12 (s 3H, H-21); 2.52 (t.1H, $J_1$=8.9, H-17); 2.88 (dd, 1H, $J_1$=16.8; $J_2$=4.5, H-3b'); 3.03 (bdd, 1H, J=16.8; $J_2$=4.5, H-3a'); 4.50-4.55 (bm, 1H, CH-2'); 4.71-4.79 (m, 1H, H-3); 5.10-5.17 (m, 2H, H-benzyl); 5.48 (bd, 1H, $J_1$=8.6 HN); 7.31-7.40 (m, 5H, phenyl). $^{13}$C NMR (100 MHz, $CDCl_3$): δ 13.40 (C-18); 20.82; 22.85; 23.21; 24.38; 26.23; 26.50; 26.83; 27.96; 28.29 (3×$CH_3$-Boc); 30.28; 31.54; 32.05; 34.58; 34.89; 35.74; 39.10; 40.35; 41.78; 52.97; 56.61; 63.82; 66.46; 75.67; 79.92 (C-Boc); 128.17, 128.26, 128.55 (Ph); 135.75; 155.35 (OCONH); 171.65 (C-5'); 172.65 (C-1'); 209.63 (C-20). IR ($CHCl_3$): 3438 (N—H), 1732 (C═O, glutamate), 1702 (C═O, $COCH_3$, NHBoc), 1499 (N—H), 1232 (C—O, glutamate), 1166 (C—O, NHBoc). ESI MS: 660.5 (100%, M+Na), 638.6 (14%, M), 603.5 (47%), 566.4 (39%). HR-MS (+ESI) calcd. for $C_{38}H_{55}NNaO$ [M+Na] 660.3871, found 660.3871. For $C_{38}H_{55}NO_7$ (637.8) calculated: 71.55% C, 8.69% H, 2.20% N; found: 71.87% C, 8.42% H, 2.06% N.

Example 8

20-Oxo-5β-pregnan-3α-yl N-(terc-butoxycarbonyl)-L-glutamyl 1-ester

The compound from the previous Example 7 afforded the title compound following the work-up as described in Example 2, $[\alpha]_D$ +87.0 (c 0.49). $^1$H NMR (400 MHz, $CD_3OD$): δ 0.60 (s, 3H, H-18); 0.92 (s, 3H, H-19); 1.45 (s, 9H, t-Bu); 2.12 (s, 3H, H-21); 2.52 (t, 1H, $J_1$=8.9, H-17); 2.63-2.67 (m, 2H, H-3a', 3b'); 4.45 (t, 1H, H-2'); 4.65-4.73 (m, 1H, H-3). $^{13}$C NMR (100 MHz, $CDCl_3$): δ 13.40 (C-18); 20.83; 22.87; 23.22; 24.39; 26.23; 26.50; 26.84; 28.09; 28.27 (3×$CH_3$-Boc); 30.05; 31.52; 32.05; 34.59; 34.89; 35.75; 39.10; 40.37; 41.79; 52.88; 56.61; 63.83; 80.20; 75.67; 80.20 (C-Boc); 155.58 (OCONH); 171.65 (C-1'); 176.59 (C-5'); 209.79 (C-20). IR ($CHCl_3$): 3439 (N—H), 1742 (C═O, glutamate, COOH, monomer), 1715 (C═O, COOH, dimer), 1703 (C═O, $COCH_3$, NHBoc), 1500 (C—N, amide), 1369 (t-Bu), 1235 (C—O glutamate), 1194 (C—O, glutamate), 1161 (C—O, NHBoc). ESI MS: 570.5 (100%, M+Na), 648.5 (13%, M+1), 492.4 (19%), 448.4 (18%). HR-MS (+ESI) calcd. for $C_{31}H_{49}NNaO_7$ [M+Na] 570.3401, found 570.3401. For $C_{31}H_{49}NO_7$ (547.7) calculated: 67.98% C, 9.02% H, 2.56% N; found: 67.75% C, 9.39% H, 2.73% N.

Example 9

20-Oxo-5β-pregnan-3α-yl L-glutamyl 1-ester

The compound from previous Example 8 afforded the title compound following the similar work-up as described in Example 3: $[\alpha]_D$ +132 (c 0.11, MeOH—$CHCl_3$ 1:1). $^1$H NMR (400 MHz, $CDCl_3$): 0.60 (s, 3H, H-18); 0.94 (s, 3H, H-19); 2.12 (s, 3H, H-21); 2.56 (t, 1H, $J_1$=8.8, H-17); 2.77 (dd, 1H, J=17.0; $J_2$=8.1, H-3b'); 2.88 (bd, 1H, $J_1$=17.0, H-3a'); 4.00-4.07 (bm, 1H, H-2'); 4.78-4.86 (bm, 2H, H-3). $^{13}$C NMR (100 MHz, $CDCl_3$-MeOD): δ 13.03 (C-18); 20.56; 22.54; 22.85; 24.08; 25.96; 26.19; 26.56; 26.97; 31.14; 31.72; 33.25; 34,31; 34.54; 35.50; 38.78; 40.15; 41.56; 44.18; 53.08; 56.35; 63.59; 76.43; 170.59 (C-1'); 177.67 (C-5'); 210.95 (C-20). IR (KBr): 1746 (C═O, glutamate), 1707 (C═O, $COCH_3$), 1215 (C—O, glutamate), 2121 ($NH_3^+$), 1616 ($CO_2^-$). ESI MS: 470.5 (32%, M+Na), 448.5 (100%, M+1), 283.2 (49%). HR-MS (+ESI) calcd. for $C_{26}H_{41}NNaO_5$ [M+Na] 470.2876, found 470.2877. For $C_{26}H_{41}NO_5$ (447.6) calculated: 69.77% C, 9.23% H, 3.11% N; found: 69.46% C, 9.49% H, 3.51% N.

Example 10

20-oxo-5β-pregnan-3α-yl-(4S)-5-(benzyloxy)-4-[(terc-butoxycarbonyl)amino]-5-oxopentanoate Treatment of the compound II (1 mmol) and Boc-Glu (OBzl) (1.1 mmol) afforded the title compound following the procedure described in Example 1, $[\alpha]_D$ +64 (c 0.28). $^1$H NMR ($CDCl_3$): δ 0.60 (s, 3H, H-18); 0.93 (s, 3H, H-19); 1.44

(s 9H, t-Bu); 2.12 (s, 3H, H-21); 2.38-2.5 (m, 2H, $CH_2$-4); 2.56 (t, 1H, $J_1$=8.9, H-17); 4.25-4.35 (bm, 1H, H-2'); 4.68-4.74 (m, 2H, H-4); 5.10-5.17 (d, 1H, J=7.9, NH); 5.18-5.22 (m, 2H, H-benzyl); 7.28-7.40 (bm, 5H, phenyl). $^{13}$C NMR (100 MHz, $CDCl_3$): δ 13.40 (C-18); 20.86; 22.94; 23.26; 24.42; 26.30; 26.62; 26.90; 27.73; 28.31 (3×$CH_3$-Boc); 30.77; 31.46; 32.18; 34.63; 34.02; 35.81; 39.21; 40.45; 41.85; 52.97; 56.72; 63.88; 67.15; 74.59; 79.92 (C-Boc); 128.59, (5H Ph); 135.32; 155.35 (OCONH); 172.07 (COO); 172.12 (COO); 209.43 (C-20). IR ($CHCl_3$): 3432 (N—H), 1730 (C═O, ester), 1702 (C═O, $COCH_3$, NHBoc), 1496 (N—H, amide), 1451 m (ring), 1368 (t-Bu), 1164 (C—O, NHBoc). ESI MS: 660.4 (100%, M+Na). HR-MS (+ESI) calcd. for $C_{38}H_{55}NNaO$ [M+Na] 660.3871, found 660.3870. For $C_{38}H_{55}NO_7$ (637.8) calculated: 71.55% C, 8.69% H, 2.20% N; found: 71.27% C, 8.75% H, 2.32% N.

Example 11

20-Oxo-5β-pregnan-3α-yl N-(terc-butoxycarbonyl)-L-glutamyl 5-ester

Compound from Example 10 afforded the title compound following the procedure of Example 2, $[\alpha]_D$ +80.0 (c 0.31). $^1$H NMR (400 MHz, $CD_3OD$): δ 0.63 (s, 3H, H-18); 0.99 (s, 3H, H-19); 1.45 (s, 9H, t-Bu); 2.13 (s, 3H, H-21); 2.52 (t, 1H, $J_1$=8.9, H-17); 2.87 (dd, 1H, J=10.2, J'=3, 1H-3b'); 3.04 (dd, 1H, J=10.2, J'=3, 1H-3a'); 4.47 (t, 1H, H-2'); 5.22-5.28 (m, 1H, NH); $^{13}$C NMR (100 MHz, $CDCl_3$): δ 13.32 (C-18); 20.80; 22.86; 23.18; 24.34; 26.22; 26.54; 26.84; 27.65; 28.23 (3×$CH_3$-Boc); 30.84; 31.40; 32.10; 34.60; 34.96; 35.75; 39.12; 40.38; 41.80; 44.32; 52.84; 56.65; 63.86; 74.66; 80.81; 80.20 (C-Boc); 155.67 (OCONH); 171.58 (C-1'); 174.14 (C-5'); 210.13 (C-20). IR ($CHCl_3$): 3436 (N—H, amide), 1730 (C═O, ester), 1710 (C═O, NEBoc), 1700 (C═O, $COCH_3$), 1501 (N—H), 1163 (C—O, NHBoc). ESI neg. MS: 546.5 (100%, M−1), 472.4 (10%). HR-MS (+ESI) calcd. for $C_{31}H_{48}NO_7$ [M−H] 546.3436, found 546.3436. For $C_{31}H_{49}NO_7$ (547.7) calculated: 67.98% C, 9.02% H, 2.56% N; found: 67.59% C, 9.23% H, 2.93% N.

Example 12

20-Oxo-5β-pregnan-3α-yl-L-glutamyl 5-ester

The compound from previous Example 11 afforded the title compound following the procedure described in Example 3, $[\alpha]_D$ +93.7 (c 0.26, MeOH—$CH_3OH$ 1:1). $^1$H NMR (400 MHz, $CDCl_3$): 0.60 (s, 3H, H-18); 0.94 (s, 3H, H-19); 2.12 (s, 3H, H-21); 2.56 (t, 1H, $J_1$=8.8, H-17); 2.50-2.60 (m, 1H, H-3a'); 3.85-3.87 (m, 1H, H-2'); 4.78-4.86 (bm, 1H, H-3); 7.35-7.40 (m, 1H, NH). $^{13}$C NMR (100 MHz, MeOD): δ 13.08 (C-18); 22.02; 23.79; 23.94; 25.48; 27.49; 27.57; 27.67; 28.14; 31.56; 31.66; 33.40; 35.81; 36.16; 37.26; 40.28; 41.83; 43.37; 45.48; 55.50; 57.93; 64.90; 76.20; 174.06 (C-11; 176.13 (C-5'); 212.47 (C-20). IR ($CHCl_3$): 1732 (C═O, glutamate), 1703 (C═O, $COCH_3$), 1215 (C—O, glutamate), 1616 ($COO^-$). ESI MS: 446.4 (100%, M−1). HR-MS (+ESI) calcd. for $C_{26}H_{40}NO_5$ [M−1] calcd. 446.2912, found 446.2912. For $C_{26}H_{41}NO_5$ (447.6) calculated: 69.77% C, 9.23% H, 3.13% N; found: 69.39% C, 9.53% H, 3.40% N.

Example 13

20-Oxo-5β-pregnan-3α-yl-adipyl 1-ester

Dicyclohexylcarbodiimide (410 mg, 2 mmol) in dry benzene (10 mL) was added into a solution of adipic acid (300 mg, 2 mmol) in dry THF (10 mL) under inert atmosphere and the mixture was stirred for 1 hour. Then a solution of compound H (3α-hydroxy-5β-pregnan-20-one) (320 mg, 1 mmol) and dimethylaminopyridine (10 mg, 0.08 mmol) in dry benzene (10 mL) was added dropwise over 15 min. This reaction mixture was stirred at room temperature for 16 hours and then, the solvents were evaporated. The residue was purified on a column of silica gel (PeAe/$Et_2O$, 9:1) to afford non-crystallizable hemiester (350 mg, 78%), $[\alpha]_D$ +89 (c 0.49). $^1$H-NMR: δ 0.60 (s, 3H, (H-18); 0.92 (s, 3H, H-19); 2.11 (s, 3H, H-21); 2.30 (m, 2H, W~20, H-adipate); 2.37 (m, 2H, W~20, H-adipate); 2.53 (t, 1H, J=9, H-17); 4.73 (m, 1H, W=35, H-3). IR ($CHCl_3$): 1727, 1706 (C═O); 1358 ($CH_3C$═O); 1233, 1193, 1183 (C—O). For $C_{27}H_{42}O_5$ (446.6) calculated: 72.61% C, 9.48% H; found: 72.13% C, 9.53% H.

Compounds described in Examples 14-16 were prepared according the same procedure as in Example 13 with the fact that instead of adipic acid a pimelic acid (heptanedioic acid) was used in Example 14; suberic acid (cork, octandioic acid) was used in Example 15 and fumaric acid (2 (E)-butene-dioic acid) was used in Example 16.

Example 14

20-Oxo-5β-pregnan-3α-yl 6-carboxyhexanoate

Oily, $[\alpha]_D$ +72.3 (c 0.33). $^1$H-NMR: δ 0.60 (s, 3H, (H-18); 0.93 (s, 3H, H-19); 2.11 (s, 3H, H-21); 2.30 (m, 2H, W~20, H-pimelate); 2.37 (m, 2H, W~20, H-pimelate); 2.53 (t, 1H, J=8.8); 4.74 (m, 1H, W=35, H-3). $^{13}$C NMR (100 MHz, MeOD): δ 13.40 (C-18); 20.86; 22.92; 23.28; 24.42; 24.70; 24.74; 26.33; 26.69; 26.92; 28.66; 31.48; 32.28; 34. 55; 34.64; 35.07; 35.82; 39.22; 40.44; 41.86; 44.33; 44.84; 56.72; 63.90; 74.06; 173.19 (COO—); 178.59 (COO); 209.59 (C-20). IR ($CHCl_3$): 3516 (COOH, monomer), 1725 (C═O, ester), 1705 (C═O, $COCH_3$), 1261 (C—O, ester). MS: (ESI): 460 (4%, M). HR-MS (+ESI) calcd. for $C_{28}H_{44}O_5Na$ [M+Na] 483.3081, found 483.3080.

Example 15

20-Oxo-5β-pregnan-3α-yl 7-carboxyheptanoate

Oily, $^1$H-NMR: δ 0.60 (s, 3H, (H-18); 0.92 (s, 3H, H-19); 2.11 (s, 3H, H-21); 2.30 (m, 2H, W~20, H-suberate); 2.37 (m, 2H, W~20, H-suberate); 2.54 (t, 1H, J=8.7); 4.73 (m, 1H, W=35, H-3). $^{13}$C NMR (100 MHz, MeOD): δ 13.40 (C-18); 20.86; 22.93; 23.28; 24.42; 24.50; 24.83; 26.33; 26.70; 26.92; 28.67; 28.70; 31.48; 32.30; 33.77; 34. 63; 34.65; 35.06; 35.82; 39.22; 40.45; 41.86; 44.33; 56.74; 63.90; 74.06; 173.19 (COO—); 178.59 (COO); 209.60 (C-20). IR spectrum ($CHCl_3$): 3517 (COOH, monomer), 1725 (C═O, ester), 1708 (C═O, $COCH_3$), 1194 (C—O, ester), 1616 ($COO^-$). ESI MS: 497.4 (100%, M+Na). HR-MS (+ESI) calcd. for $C_{29}H_{46}NaO_5$ [M+Na] 497.3237, found 497.3239.

Example 16

20-Oxo-5β-pregnan-3α-yl (E)-3-carboxyprop-2-enoate $^1$H-NMR: δ 0.62 (s, 3H, H-18); 0.99 (s, 3H, H-19); 2.11 (s, 3H, H-21); 2.53 (t, 1H, J=8, H-17); 4.77 (m, 1H, W=35, H-3); 6.69 (d, 2H, J=14, H-fumarate). IR ($CHCl_3$): 1723, 1702 (C═O); 1358 ($CH_3C$═O); 1181, 982 (C—O); 1645 (C═C). For $C_{25}H_{36}O_5$ (416.6) calculated: 72.08% C, 8.71% H; found: 72.05% C, 8.86% H.

Example 17

20-Oxo-5β-pregnan-3α-yl (Z)-3-carboxyprop-2-enoate

4-Dimethylaminopyridine (1 mg) a maleic anhydride (180 mg, 1.55 mmol) were added into a solution of the compound II (100 mg, 0.31 mmol) in pyridine (0.5 mL) at 0° C. The reaction mixture was allowed to stand at 40° C. for 16 h and then poured into ice. The product was extracted with EtOAc (3×30 mL), collected organic phases were washed with aqueous solution of citric acid (1%, 30 mL), aqueous solution of sodium bicarbonate (5%, 20 mL), and water (30 mL). Organic phase was dried over sodium sulfate and solvents were evaporated. The residue was purified on prep-TLC (200×200×0.3 mm) to afford 116 mg (90%) of hemiester, $^1$H-NMR: δ 0.62 (s, 3H, H-18); 0.99 (s, 3H, H-19); 2.11 (s, 3H, H-21); 2.67 (t, 1H, J=9, H-17); 4.77 (m, 1H, W=35, H-3); 6.77 (d, 2H, J=6, H-maleinate). $^{13}$C NMR (100 MHz, $CD_3OD$): δ 13.80 (C-18); 22.03; 23.80; 23.93; 25.48; 27.47; 27.54; 28.14; 33.14; 35.83; 36.15; 37.26; 40.25; 41.80; 43.39; 45.47; 57.86; 64.89; 76.81; 130.66; 131.66; 166.96; 212.45. IR ($CHCl_3$): 1725, 1705 (C═O); 1358 ($CH_3C$═O); 1172, 982 (C—O); 1645 (C═C). HR-MS (ESI) calculated for $C_{25}H_{36}O_5$ (M+Na) 439.2455 found 439.2455. For $C_{25}H_{36}O_5$ (416.6) calculated: 72.08% C, 8.71% H; found: 72.05% C, 8.86% H.

Compounds in Example 18 and 19 were preparded according to the procedure of Example 17.

Example 18

20-Oxo-5β-pregnan-3α-yl 3-carboxyperfluoropropanoate

Oily material was obtained by a treatment of compound II (240 mg, 0.75 mmol) in pyridine (5 mL) and perfluorosuccinanhydride (645 mg, 3.75 mmol). $^1$H-NMR: δ 0.60 (s, 3H, H-18); 0.92 (s, 3H, H-19); 2.11 (s, 3H, H-21); 2.53 (t, 1H, J=8.7); 4.75 (m, 1H, W=35, H-3). This compound was characterized as methylester: $[\alpha]_D$=+82.8 (c 0.21, MeOH). $^1$H-NMR: δ 0.61 (s, 3H, H-18); 0.95 (s, 3H, H-19); 2.12 (s, 3H, H-21); 2.55 (t, 1H, J=8.9, H-17); 3.10 (s, 3H, methylester); 4.98 (m, 1H, W=35, H-3); 1775, 1699 (C═O); 1357 ($CH_3C$═O); 1180, 1154, 1140, 1103 (C—O, C—$F_2$). ESI MS: 527.0 (100%, M+Na). HR-MS (ESI) calculated for $C_{26}H_{36}F_4O_5Na$ (M+Na) 527.2391 found 527.2388.

Example 19

20-Oxo-5β-pregnan-3α-yl 3-carboxy-ξ-methyl-propanoate

A title compound (a mixture of isomers) was obtained by a treatment of compound II (100 mg, 0.31 mmol), 4-dimethylaminopyridine (3 mg, 0.03 mmol), and methyl-succinyl-anhydride (170 mg, 1.5 mmol). $^1$H-NMR: δ 0.60 (s, 3H, H-18); 0.93 (s, 3H, H-19); 2.11 (s, 3H, H-21); 2.30 (m, 2H, w~20, H-methylpropanoate); 2.55 (t, 1H, J=8, H-17); 4.75 (m, 1H, w=35, H-3). IR ($CHCl_3$): 1712, 1702 (C═O); 1358 ($CH_3C$═O); 1181, 987 (C—O). For $C_{26}H_{40}O_5$ (432.6) calculated: 72.19% C, 9.32% H; found: 71.88% C, 9.70% H.

Example 20

Compound HET a) 4-[1,11-Bis(methylensulfo)-3,3,9,9-tetramethyl-4,8-diaza-6-oxa-3,6,8,9-tetrahydropentacen-13-yl]-benzene-1,3-dicarboxylic acid 1-succinimidyl ester

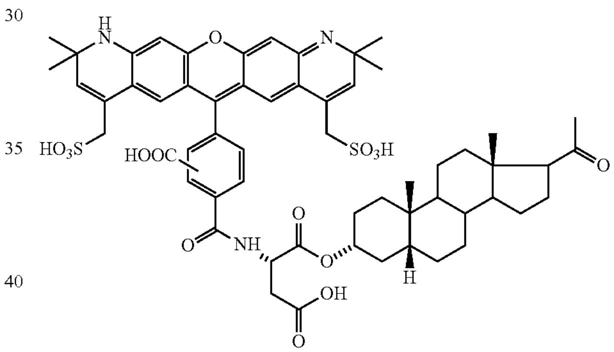

Active ester Alexa fluor 567 (Molecular Probes) (57.3 mg, 64.1 μmol) and aspartate from Example 3 (33 mg, 1.2 eq., 76.8 μmol) were dissolved in DMSO (3 mL) and pyridine (1 mL) and the reaction mixture was treated at 40° C. for 72 h. The completion of the reaction was checked by HPLC and solvents were evaporated under vacuum at 60° C. The residue was purified on preparative TLC in a mixture of butanol-methanol-water (3:1:1) and 1% (v/v) of triethylamine. The eluate was dried under reduced pressure (1 mm) to afford 40.3 mg of the title compound IR: 1648 s (CONH), 3360, 3300 (NH), 1246 (C—O, ester), 1731 (C═O, ester), 1695 (C═O, ketone), 1718, 1685 (C═O, acid), 1229 ($SO_3H$), 1612, 1497, 1405 (ring). MS-ESI neg: 368.8 (63%, $M-3H)^{-3}$, 553.7 (63%, $M-2H)^{-2}$, 1130.1 (2%, M+Na), 1146.1 (6%, M+K); (HR) for $(C_{58}H_{67}N_3O_{15}N_2\text{-}2H)^{-2}$ calculated: 553.69286. found: 553.69231. $^1$H NMR (400 MHz, $D_2O$, $K_2CO_3$): 0.54 (s, 3H, H-18); 0.90 (s, 3H, H-19); 0.88-0.92 (m, $4CH_3$, rhodamine) 1.27 (t, 9H, J=7.0, $NCH_2CH_3$); 2.12 (s, 3H, H-21); 3.60 (t, 8H, J=7.0, $NCH_2CH_3$); 5.69 (s, 2H, H-11+21, rhodamine); 6.53 (m, 4H, 4H-rhodamine); 7.33 (d, 2 H, J=8.0 H-6' and H-2', rhodamine); 8.19 (d, 2H, J=8.0, H-3' a H-5', rhodamine).

b) 20-Oxo-5β-pregnane-3α-yl N-(7-nitrobenz-2-oxa-1,3-diazole-4-yl)-L-aspartyl 1-ester

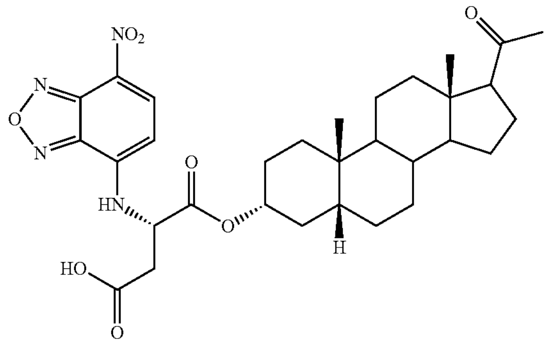 [SMILES: CC(=O)C1CCC2C3CC[C@@H]4C[C@H](OC(=O)[C@H](CC(=O)O)Nc5ccc([N+](=O)[O-])c6nonc56)CC[C@]4(C)C3CC[C@]12C]

Steroid conjugate from example 3 (103 mg; 0.24 mmol) was dissolved in dry dichloromethane (7 mL) and triethylamine (0.10 mL, 0.72 mmol) and solution of NBD-Cl (57 mg, 0.29 mmol) in dichloromethane (1 mL) was added at room temperature. The mixture was stirred overnight in darkness and then poured into water (20 mL), acidified by aq. HCl to pH 3-4 and organic phase was separated. Aqueous phase was then extracted with EtOAc (3×10 mL), washed with brine and dried with anhydrous $MgSO_4$. Solvents were evaporated in vacuo and the residue was purified by preparative TLC in MeCN:MeOH:AcOH (90:10:1) to afford title compound as orange-brown foam (121 mg, 85%). $[\alpha]_D$=+39 (c 0.05, $CHCl_3$). NMR (400 MHz, $CDCl_3$): δ 0.60 (s, 3H, H-18); 0.94 (s, 3H, H-19); 2.12 (s, 3H, H-21); 2.54 (t.1H, $J_1$=8.7, H-17); 3.14 (dd, 2H, $J_1$=17.1, $J_2$=5.0, H-3'); 4.79-4.83 (m, 1H, 2'); 4.83-4.91 (m, 1H, H-3); 6.29 (d, 1H, J=8.5; H—N); 7.01 (d, 1H, $J_1$=8.4, Ar); 8.50 (d, 1H, J=8.5 Ar). IR ($CHCl_3$): 1736 (C═O, ester), 1699 (C═O, $COCH_3$), 1499 (N—H, amide), 1572, 1318 ($NO_2$). ESI MS: 641.3 (22%, M+2Na+H), 619.3 (100%, M+Na), 597.1 (9%, M+H).

Example 21

20,20-(Ethylendioxy)-5β-pregnan-3β-yl-tosylate

A solution of 20-oxo-5β-pregnan-3β-yl-tosylate (Swann D. A., Turnbull J. H.: Tetrahedron 1966, 22, 231; 200 mg, 0.42 mmol), orthoethyl formate (0.38 ml, 2.3 mmol), ethylene glykol (0.3 ml, 5.8 mmol), and p-toluensulfonic acid monohydrate (2 mg, 0.01 mmol) in dry benzene (2 mL) were stirred at room temperature for 2 days. The reaction mixture was poured into saturated solution of sodium bicarbonate (30 mL), steroid was extracted with EtOAc (2×60 mL), the organic phase was washed with water and dried over magnesium sulfated. Solvents were evaporated and the residue was purified on prep-TLC (6 plates, 200×200×0.3 mm) in a mixture of PeAe/$Et_2O$ (1:1) and 2 drops of pyridine to afford 194 mg (89%) of title compound, m.p. 146-148° C. (PeAe-$Et_2O$), $[\alpha]_D$ +11.7 (c 0.37, $CHCl_3$). $^1$H-NMR (200 MHz): 0.73 (s, 3H, H-18); 0.94 (s, 3H, H-19); 1.27 (s, 3H, H-21); 2.44 (s, 3H, $CH_3$, tosylate); 3.81-4.01 (m, 4H, $OCH_2CH_2O$); 4.83 (m, 1H, H-3); 7.32 (d, 2H, J=7.8, H-3 and H-5, tosylate); 7.78 (d, 2H, J=8.3, H-2 and H-6, tosylate). IR ($CHCl_3$): 1358 ($SO_2$, tosylate), 1189 ($SO_2$, tosylate), 1053 ($OCH_2CH_2O$—), 901 (C—O, tosylate). FAB MS: 517 (6%, M+H), 345 (2.5%, M−tosylate). For $C_{30}H_{44}O_5S$ (516.7) calculated: 69.73% C, 8.58% H, 6.21% S; found: 69.92% C, 8.79% H, 6.41% S.

Example 22

Dimethyl-(2-[20,20-(ethylendioxy)-5β-pregnan-3α-yl]propandioate)

To a stirred solution of sodium salt of dimethyl malonate, prepared by refluxing toluene (30 mL), sodium (80 mg, 3.5 mmol), and dimethyl malonate (0.707 mL, 6.2 mmol) until all the sodium had been dissolved, was added a solution of compound from Example 21 (600 mg, 1.16 mmol) in toluene (20 mL) dropwise during vigorous stirring. After refluxing for additional 12 hours, the solution was cooled to room temperature, the precipitated sodium p-toluenesulfonate was filtered off, washed with small amount of toluene, and the combined toluene extracts were evaporated. The obtained oily residue was dissolved in ether (200 mL) and washed with water, and the solution was dried, and evaporated. The residue was purified by chromatography on a column of silica gel (20 g) in a mixture of PeAe/$Et_2O$ (9:1) to afforded title compound (430 mg, 77%): m.p. 98-102° C. (ethyl acetate), $[\alpha]_D$ +55.4 (c 0.25, $CHCl_3$). $^1$H NMR (400 MHz, $CDCl_3$): 0.73 (s, 3H, H-18); 0.93 (s, 3H, H-19); 1.29 (s, 3H, H-21); 3.19 (d, 1H, J=9.2, $CH(COOMe)_2$); 3.72 (s, 6H, COOMe); 3.80-4.02 (m, 4H, —$OCH_2CH_2O$—). IR ($CHCl_3$): 1753 (C═O, COOMe), 1731 (C═O, COOMe); 1436 ($CH_3$, COOMe); 1472, 1295 ($CH_2$, acetal); 1149 (C—O). ESI MS: 976 (47%, 2M+H+Na), 975 (100%, 2M+Na), 499 (15%, M+Na). For $C_{28}H_{44}O_6$ (476.6) calculated: 70.56% C, 9.30% H; found: 70.61% C, 9.53% H.

Example 23

Methyl-(2-[20,20-(ethylendioxy)-5β-pregnan-3α-yl]-acetate)

A solution of compound from Example 22 (187 mg, 0.39 mmol) and sodium cyanide (37.5 mg, 0.76 mmol) in dimethylsulfoxide (11 mL) were heated under inert atmosphere at 210° C. for 3 hours. After cooling, the mixture was poured into water (100 mL) and extracted with ether (3×100 mL). The collected organic phases were washed with water and taken down. The residue was purified by prep-PLC (6 plates) in a mixture of PeAe/$Et_2O$ (4:1), affording 90 mg (57%) of title compound, m.p. 75-76° C. (ethyl-acetate). $[\alpha]_D$ +68.0 (c 0.25, $CHCl_3$). $^1$H-NMR (400 MHz, $CDCl_3$): 0.73 (s, 3H, H-18); 0.93 (s, 3H, H-19); 1.29 (s, 3H, H-21); 2.01 (m, 1H, H-3β); 2.22 (d, 2H, J=7.3, $CH_2COOCH_3$); 3.66 (s, 3H, $COOCH_3$); 3.85-4.00 (m, 4H, —$OCH_2CH_2O$—). IR ($CHCl_3$): 1729 (C═O), 1295, 1073, 1054 ($CH_2$, acetal), 1142 (C—O). ESI MS: 419 (61%, M+1); 357 (26%, M−$CH_2COOCH_3$); 230 (100%). For $C_{26}H_{42}O_4$ (418.6) calculated: 74.60% C, 10.11% H; found: 74.42% C, 10.30% H.

Example 24

2-[20,20-(Ethylendioxy)-5β-pregnan-3α-yl]acetic acid

A solution of potassium hydroxide (55 mg, 0.98 mmol) in ethanol (0.125 mL) and water (0.125 mL) was added to a stirred solution of compound from Example 23 (75 mg, 0.18 mmol) in methanol (2 mL). The mixture was heated at 120° C. for 1.5 hour. After cooling, it was poured into water (50 mL), an aqueous solution of hydrochloric acid (12%) was added to the aqueous phase to reach pH 1, and the product was extracted with ether (30 mL) and chloroform (2×30 mL). Collected organic phases were washed with water, dried, and evaporated to give title compound (45 mg, 63%), m.p. 164-167° C., $[\alpha]_D$ +41.0 (c 0.19, $CHCl_3$). $^1H$ NMR (400 MHz, $CDCl_3$): 0.74 (s, 3H, H-18); 0.93 (s, 3H, H-19); 1.29 (s, 3H, H-21); 2.02 (m, 1H, H-3β); 2.26 (d, 2H, J=6.6, $CH_2COOH$); 3.86-3.98 (m, 4H, —$OCH_2CH_2O$—). IR ($CHCl_3$): 3516 (O—H, COOH, monomer), 3088 (O—H, COOH, dimer), 1739 (C═O, COOH, monomer), 1705 (C═O, COOH, dimer), 1496, 1375, 1054 ($CH_2$, acetal). FAB MS: 405 (4%, M+H); 261 (1%, M−$CH_2COOH$, $C_4H_7O_2$); 231 (2%, M−$CH_2COOH$, $C_4H_7O_2$, 2×$CH_3$). For $C_{25}H_{40}O_4$ (404.2) calculated: 74.22% C, 9.97% H; found: 73.99% C, 10.16% H.

Example 25 a) 2-(Oxo-5β-pregnan-3α-yl)-acetic acid

A solution of p-toluensulfonic acid monohydrate (20 mg, 0.12 mmol) in water (0.6 mL) was added into a solution of compound from Example 24 (55 mg, 0.13 mmol) in acetone (5 mL) and the reaction mixture was stirred for 24 hours. Then, it was poured into water, acidified by an aqueous solution of hydrochloric acid (12%), and extracted with ether (30 mL) and chloroform (2×30 mL). Collected organic phases were washed with water, dried, and evaporated to give title compound (42 mg), m.p. 189-192° C. (acetone), $[\alpha]_D$ +127.6 (c 0.2, $CHCl_3$). IR ($CHCl_3$): 3516 (O—H, COOH, monomer), 3090 (O—H, COOH, dimer), 1739 (C═O, COOH, monomer); 1702 (C═O, COOH, dimer a C═O, ketone), 1702 (C═O, $COCH_3$). $^1H$ NMR (400 MHz, $CDCl_3$): 0.59 (s, 3H, H-18); 0.93 (s, 3H, H-19); 2.11 (s, 3H, H-21); 2.16 (m, 1H, H-3β); 2.27 (d, 2H, J=6.8, $CH_2COOH$); 2.54 (t, 1H, J=8.8, H-17). ESI MS: 720 (42%, 2M), 719 (100%, 2M−1), 359 (21%, M−1). For $C_{23}H_{36}O_3$ (360.3) calculated: 76.62% C, 10.06% H; found: 76.54% C, 10.25% H.

b) 2-(20-Oxo-5β-pregnan-3α-yl)propandioic acid

A solution of potassium hydroxide (140 mg, 2.5 mmol) in ethanol (0.35 mL) and water (0.35 mL) was added to a stirred solution of dimethylester from Example 22 (55 mg, 0.11 mmol) in methanol (4 mL). The mixture was heated at 120° C. for 6 hours. After cooling, it was poured into water and extracted with ether (50 mL). A mixture of HCl/$H_2O$ (1:2) was added to the aqueous phase up to pH 1 and it was allowed to stay at room temperature for 3 hours. Subsequently, it was extracted with chloroform (2×30 mL), collected organic phases were washed with water, dried and evaporated. The residue was crystallized from PeAe/Et to give title compound (27 mg, 58%): m.p. 214-215° C., $[\alpha]_D$ +82.7 (c 0.25, $CHCl_3$). $^1H$ NMR (400 MHz, $CDCl_3$): 0.58 (s, 3H, H-18); 0.93 (s, 3H, H-19); 2.12 (s, 3H, H-21); 2.15 (m, 1H, H-3β); 2.54 (t, 1H, J=8.6, H-17); 3.17 (d, 1H, J=8.5, $CH(COOH)_2$). IR ($CHCl_3$): 3500 (O—H, COOH, monomer), 3200 (O—H, COOH, dimer), 1741 (C═O, COOH, monomer), 1702 (C═O, ketone). ESI MS: 808 (4%, 2M), 404 (22%, M), 403 (100%, M−H). For $C_{24}H_{36}O_5$ (404.5) calculated: 71.26% C, 8.97% H,. found: 71.08% C, 8.80% H.

Example 26

N-(20-Oxo-5β-pregnan-3α-yl) glycine methylester hydrochloride

Glycine methyl ester hydrochloride (89 mg, 0708 mmol) with triethylamine (0.072 mL) and 5β-pregnane-3,20-dione (200 mg, 0.632 mmol) were mixed in neat titanium (IV) isopropoxide (302 mg, 1.06 mmol) and dry toluene (0.4 mL). The mixture was stirred under nitrogen for 3 h. Methanol (2.8 mL) was added. Then $NaBH_4$ (38 mg, 1.01 mmol) was carefully added. After 5 min the reaction was finished by adding 0.1 N NaOH. The resulting mixture was filtered through Celite, and the residue was washed with ether (2×30 mL) and ethyl acetate (2×30 mL). The organic layer was separated, dried ($MgSO_4$) and the solvents were removed under reduced pressure. The residue was purified on preparative TLC (5 plates, 200×200×0.3 mm) in a mixture of toluene-ethyl acetate (1:1) to afford 43 mg (17%). $^1H$ NMR (400 MHz, $CDCl_3$): δ 0.59 (s, 3H, H-18); 0.92 (s, 3H, H-19); 2.11 (s, 3H, H-21); 2.45-2.53 (m, 1H, H-3); 2.52 (t, 1H, J=8.8, H-17); 3.46 (s, 2H, H-2'); 3.74 (s, 3H, OMe). $^{13}C$ NMR (100 MHz, $CDCl_3$): δ 13.34 (C-18); 20.77; 22.86; 23.45; 24.40; 26.37; 27.15; 27.87; 31.45; 34.00; 35.08; 35.69; 35.83; 39.22; 40.29; 42.09; 44.27; 48.09; 51.74; 56.70; 57.24; 63.86; 173.13 (C-1'); 209.51 (C-20). The product was subsequently characterised as hydrochloride. $[\alpha]_D$=+61.9 (c 0.24, $CHCl_3$).IR ($CHCl_3$): 2708 ($N^+H_2$), 1758 (C═O, ester), 1698 (C═O, $COCH_3$). 1235 (C—O, ester). MS-ESI: 390.2 [100%, $M+H]^+$; (HR) for $[C_{24}H_{40}NO_3+H]^+$ m/z calculated: 390.3003. found: 390.3002.

Example 27

N-(20-Oxo-5β-pregnan-3α-yl) glycine

Compound from the example 26 (73 mg; 187 μmol) was dissolved in dry ethylacetate (1.9 mL) along with lithium iodide (150 mg; 1.12 mmol) and the mixture was refluxed 2 days under argon atmosphere. The reaction mixture was then finished by addition of water (2 mL), product was extracted with chloroform (3×2 mL). Organic layer was washed with brine (2 mL), dried over $MgSO_4$ and evaporated to give crude title acid, which was purified on preparative TLC (2 plates) in a mixture of chloroform-methanol-triethylamine (180:20:1) to afford the off-white solid (20 mg; 29%). $^1H$ NMR (400 MHz, $CDCl_3$-MeOD 4-1): δ 0.61 (s, 3H, H-18); 0.99 (s, 3H, H-19); 2.14 (s, 3H, H-21); 2.60 (t.1H, J=8.8, H-17); 3.08-3.16 (m, 1H, H-3); 3.49 (s, 2H, H-2'). IR ($CHCl_3$): 3452 (NH) 2650, 2470 ($N^+H_2$), 1698 ($CH_3C$═O, —COOH), 1637 ($N^+H_2$), 1472 ($N^+H_2$), 1390 ($CH_3$), 1358 ($CH_3CO$). MS-ESI: 376.2 [100%, $M+H]^+$; 398.2 [7%, $M+Na]^+$ (HR) for $[C_{23}H_{37}O_3N+H]^+$ m/z calculated: 376.2846. found: 376.2846.

Example 28

Effects of Pregnanolone Sulphate and its Analogues on Native and Recombinant NMDA Receptors Primarily dissociated hippocampal cultures were prepared from 1-2-day-old rat pups. Animals were decapitated and subsequently hippocampus was isolated. Cell suspension was prepared by trypsine treatments and mechanical dissociation. The cells were inoculated on 12- and 25-mm polylysine-coated glasses at a density of approx. 500 000 cells/$cm^2$. Neuronal cultures were maintained in Neurobasal™-A medium (Invitrogen, Carlsbad, USA) with glutamine (0.5 mM) a B-27 Serum-Free Supplement (Invitrogen) at 37° C. and 5% $CO_2$.

HEK293 cells (American Type Culture Collection, ATTC No. CRL1573, Rockville, Md.) were cultivated in Opti-MEM® I media (Invitrogen) with addition of 5% fetal bovine serum at 37° C. and transfected with NR1-1a/NR2B/GFP plasmids, as described in the scientific literature (Cais et al., 2008). Same amounts (0.3 μg) of cDNA coding NR1, NR2 and GFP (green fluorescent protein) (pQBI 25, Takara, Japan) were mixed with 0.9 μl of Matra-A Reagent (IBA, Gottingen, Germany) and added to confluent HEK293 cells cultivated in v 24-pit cultivating plate. P After trypsination, the cells were re-suspended in Opti-MEM® I containing 1% fetal bovine serum. Subsequently, 20 mM $MgCl_2$, 1 mM D,L-2-amino-5-phosphonopentanoic acid, 3 mM kynurenic acid and ketamine was added to the mixture and cells were inoculated on the polylysine-coated glass plates having 25 mm in diameter. The following genes coding NMDA receptor subunits were used for transfection: NR1-1a (GenBank accession no. U08261) and NR2B (GenBank accession no. M91562).

5-10-day old hippocampal culture cells or HEK293 cultured cells were used for electrophysiological investigations with a latency of 16-40 h after transfection. Whole-cell currents were measured by patch-clamp amplifier (Axopatch 1D; Axon Instruments, Inc. Foster City, USA) after capacitance and serial resistance (<10 MΩ) compensation to 80-90%. Agonist-induced responses were filtered to 1 kHz (8-pole Bessel filter; Frequency Devices, Haverhill, USA), digitized with sampling frequency of 5 kHz and analyzed by pClamp v.9 software (Axon Instruments, USA). Micropipettes made of borosilicate glass were filled with intracellular solution, containing 125 mM D-glukonic acid, 15 mM cesium chloride, 5 mM EGTA, 10 mM HEPES buffer, 3 mM magnesium chloride, 0.5 mM calcium chloride and 2 mM magnesium-salt of ATP (pH adjusted to 7.2 by cesium hydroxide solution). Extracellular solution (ECS) contained 160 mM sodium chloride, 2.5 mM potassium chloride, 10 mM HEPES, 10 mM glucose, 0.2 mM EDTA a 0.7 mM calcium chloride (pH adjusted 7.3 by sodium hydroxide solution). Glycine was added to both testing and control solution. Moreover, bicuculline (10 μM) and tetrodotoxin (0.5 μM) was added to hippocampal cultures. Steroid-containing solutions were prepared from fresh solution (20 mM) of steroid dissolved in dimethyl-sulfoxide (DMSO). Same concentrations of DMSO were used in all extracellular solutions. Control and experimental solutions were applied via microprocessor-controlled perfusion system with approx. rate of solution exchange in areas adjacent to cells reaching ~10 ms.

Current responses produced by 100 μM NMDA (for hippocampal neurons) or 1 mM glutamate (for recombinant NMDA receptors) were measured at membrane potential maintained at −60 mV. Similarly as described before, pregnanolon sulphate decreased the amplitude of responses elicited by NMDA. After application of 100 μM preganolone sulphate the mean inhibition effect reached 71.3±5.0% (n=5) of responses elicited by NMDA receptor activation on hippocampal neurons and 67.2±8.2% (n=5) on recombinant NR1/NR2B receptors (Petrovic et al., 2005). Our synthetic analogues of pregnanolone sulphate exhibited significant inhibitory effect (30-70% of maximum inhibition) at concentration range 50, 100 and 200 μM. Relative effect of steroid-induced inhibition was used for calculating $IC_{50}$. $IC_{50}$ was calculated using formula $RI=1-(1/1+([steroid]/IC_{50})^h)$, where RI denotes relative effect of steroid-induced inhibition and h is a parameter of Hill's coefficient (1.2). $IC_{50}$ values are stated in the following table.

Newly synthesized analogues from Examples 1-25 have the same mechanism of action on the NMDA receptors as pregnanolone sulphate, but they differ in their relative affinities (see Table 1).

TABLE 1

| Tested compound - Compound from example No. | Relative inhibition effect (%) | $IC_{50}$ (μmol) | Number of cells |
|---|---|---|---|
| Pregnanolone sulphate | 67.2 ± 8.2 | 55 | 5 |
| Compound from Example 26 | 43.4 ± 3.4 | 250 | 4 |
| Compound from Example 25 | 63.6 ± 21.1 | 126 | 5 |
| Compound from Example 3 | 83.6 ± 2.7 | 51 | 5 |
| Compound from Example 9 | 77.1 ± 5.2 | 73 | 5 |
| Compound from Example 20 | 36.3 ± 3.2 | 320 | 5 |
| Compound from Example 13 | 87.3 ± 8.9 | 40 | 4 |
| Compound from Example 17 | 81.6 ± 2.7 | 14 | 6 |
| Compound from Example 19 | 80.9 ± 3.6 | 30 | 4 |
| Compound from Example 15 | 54.0 ± 10.8% | 175 | 5 |
| Compound from Example 14 | 61.5 ± 10.6% | 135 | 5 |

The results show that synthetic analogues of pregnanolone sulphate have the same mechanism of action on NMDA receptors as pregnanolone sulphate; however, they differ in their affinity for these receptors. Due to ethically-justified requirements for minimization of numbers of laboratory animals used in experimental studies, we have chosen the compound from the Example 9 as a model molecule and we have subjected it to intimate investigation regarding its effect on animal behavior and its neuroprotective properties in animal models. All experiments complied with standard accepted rules for animal care (Animal Protection Code of the Czech Republic, EU directives, and National Institute of Health guidelines).

Example 29

Effect of the Compound from Example 9 on Spontaneous Locomotor Activity in the Open-field Test and Sensorimotor Gating Tested with Prepulse Inhibition of the Startle Response For assessment of the spontaneous locomotor activity, animals were observed for 30 min in a square open-field apparatus (1 m×1 m). Animals were tracked with Ethovision Pro system (Noldus, Netherlands) and total path traveled during this session was evaluated. The compound from Example 9 was applied subcutaneously (dissolved in cyclodextrin) 30 min prior to behavioral observations at doses 1 mg/kg a 10 mg/kg; control animals were injected with saline.

Figure 1:
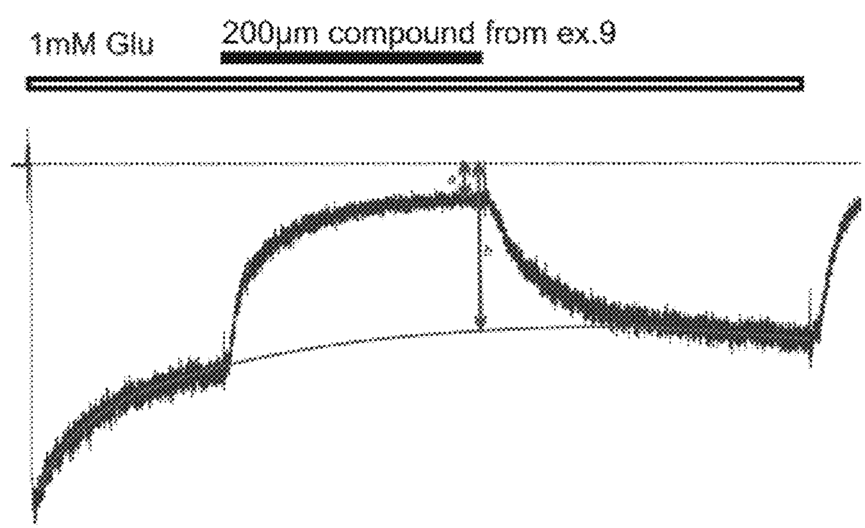
FIG. 1 shows current responses produced by application of 1 mM glutamate and the effect of neurosteroid from example 9, co-administered (200 μM) with glutamate. Records were made using patch-clamp apparatus from individual cultured HEK293 cells transfected with NR1/NR2B receptors. The inhibition index was calculated according to: (1-a/b).100(%).
Figure 2:
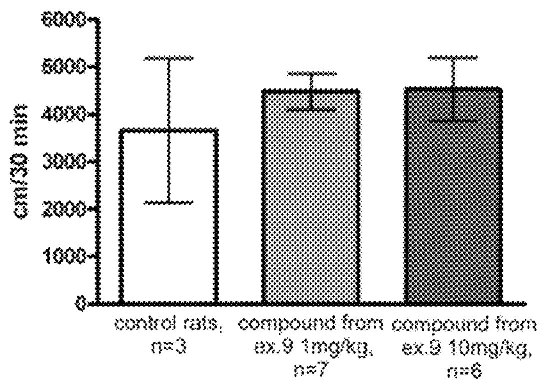
FIG. 2 Top panel: Total distance traveled in the open-field session as a measure of spontaneous locomotor activity (according to example 29) was not different between control animals and rats treated with compound from Example 9.
Figure 2:
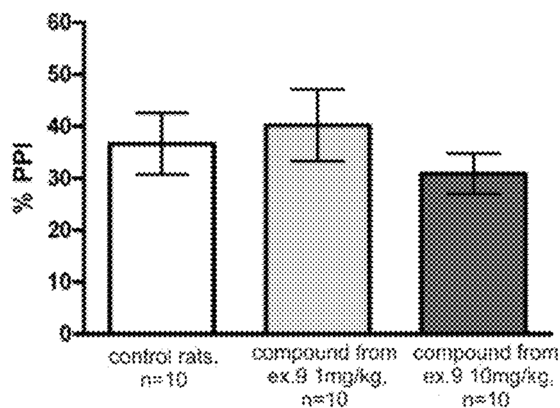

Results showed that compound from Example 9 did not significantly alter the spontaneous locomotor activity; all groups exhibited similar total distance (FIG. 2; top panel).

Testing prepulse inhibition of the startle response as a measure of possible deficit in sensorimotor gating has shown that none of the doses of the compound from Example 9 significantly altered this parameter (compared to control animals (FIG. 2; bottom panel).

Example 30

Effect of Compound from Example 9 and Action of Dizocilpine (a Non-competitive Antagonist of NMDA Receptors; Standardly Used as Positive Control and Referred Hereafter as Dizocilpine) on the Behavior of Rats in Active Allothetic Place Avoidance (AAPA), a Spatial Task Requiring Spatial Orientation and Cognitive Functions The effect of compound from Example 9 on cognitive behaviors and locomotion was assessed using active allothetic place avoidance (AAPA) task, which requires intact hippocampi and ability of animals to navigate in space using distinct reference frames (spatial navigation and "cognitive coordination") (Wesierska et al., 2005) and it also allows measuring changes in the accompanying locomotor activity. AAPA task training involves animals trained to move over a slowly rotating uniform circular arena, on which a prohibited sector is defined, entering which is punished by a mild foot-shock. A shock sector and its position can be determined solely by its relationship to distal orienting cues in the room (Stuchlik et al., 2008).

This task is highly dependent upon hippocampal formation, with unilateral reversible ablation of this structure with TTX leading to avoidance deficit (Cimadevilla et al., 2001). Animals solving this task should walk in a direction opposite to arena rotation; otherwise it would be repeatedly brought to a fixed sector by arena rotation. We conducted 4 acquisition session of AAPA task, during which the sector location was always reinforced and remained stable throughout the training. Each session lasted 20 min.

Control animals obtained saline intraperitoneally (i.p.) whilst experimental groups received subcutaneous (s.c.) injections of the compound from Example 9 at doses 1 mg/kg and 10 mg/kg (dissolved in cyclodextrin). Solution of compound from Example 9 (1 mg/2 ml or 10 mg/2 ml in cyclodextrin) was applied s.c. at a volume 2 ml/kg of body weight (b.w.). Intraperitonal application of dizocilpine (a non-competitive NMDA receptor antagonist; showing significant neuroprotective activity but exerting cognition-disturbing and psychotomimetic effects) was used as a positive control. Dizocilpine was applied at doses 0.1 mg/kg, 0.2 mg/kg and 0.3 mg/kg. It is worth noting that dizocilpine (albeit its experimental neuroprotective activity) is often used to model schizophrenia-like behaviors in humans and it has been repeatedly shown to exert a dose-dependent learning deficit and hyperlocomotion.

Figure 3:
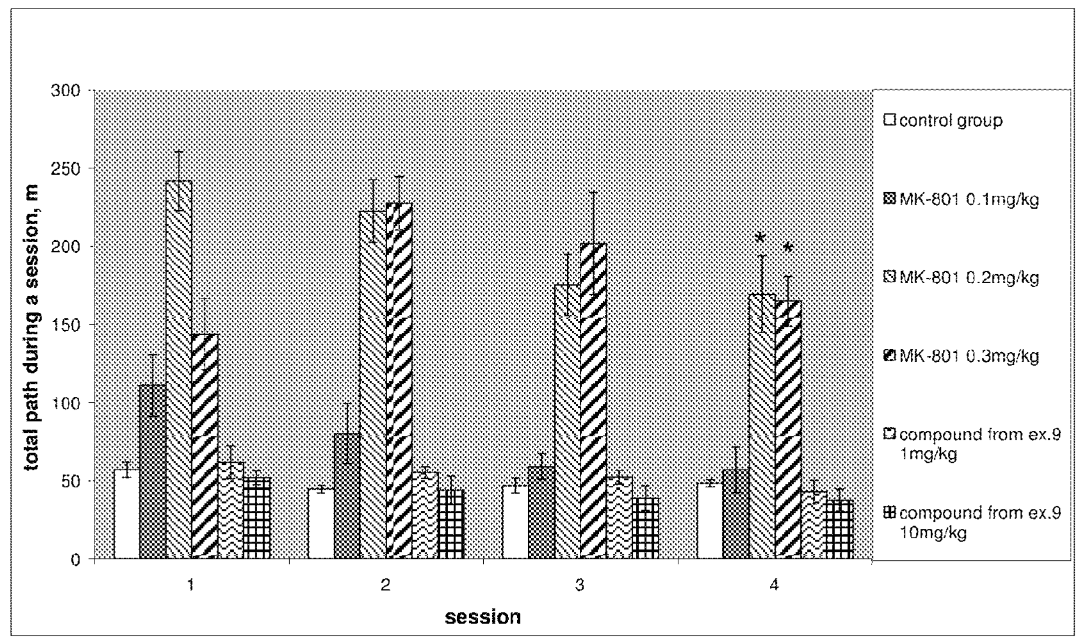
FIG. 3 shows total distance traveled by rats in the AAPA task after application of dizocilpine and compound from Example 9 (according to example 30). * denotes significant difference compared to controls ($p<0.05$).

The results in four daily sessions are shown in FIG. 3 (means±S.E.M.). For clarity, statistical evaluations were performed for the final sessions (representing asymptotic levels of control animals); this approach has repeatedly proved useful in evaluation on neuropharmacological data from AAPA task.

Locomotor activity of animals was assessed in the AAPA as total distance traveled in the coordinate frame of the arena (without passive rotation) in each 20-min session. Animals treated with substance from example 9 failed to exhibit either decrease or increase in total distance compared to controls, whilst dizocilpine dose-dependently and consistently stimulated the locomotor activity. The hyperlocomotion was not observed at the lowest dose of dizocilpine (0.1 mg/kg) but a marked locomotor hyperactivity was observed after 0.2 mg/kg, with an even more dramatic hyperlocomotion produced by 0.3 mg/kg dose.

It should be emphasized that hyperactivity (hyperlocomotion) induced by antagonists of NMDA receptors is sometimes considered to be into certain extent analogous to human positive symptoms of schizophrenia as both phenomena has been shown to relate to hyperfunction of mesolimbic dopaminergic circuits. Evaluation of locomotor activity in the AAPA task has shown that compound from Example 9 did not alter locomotor activity in this behavioral configuration. The results of activity analysis are depicted in FIG. 3.

FIG. 3 shows the total distance per session in the AAPA training, after application dizocilpine and compound from Example 9. Two highest doses of dizocilpine caused a pronounced hyperlocomotion, whilst our compound did not cause a significant alteration of locomotor activity. * denotes significant difference compared to controls ($p<0.05$); statistical evaluations were performed for the final session 4, which represented asymptotic level of controls.

Example 31

Number of Entrances into Shock Sector

Another parameter, which can be measured and which brings a spatial aspect to behavioral analysis, is number of entrances into prohibited sector (occasionally termed "number of errors"). This parameter actually shows the overall spatial performance of the task, indicating "efficiency, in which can rats learn this task", and it is related to cognitive functions of animals. Results have shown that neither of doses of compound from Example 9 caused worsening in this parameter, whilst dizocilpine dose-dependently disrupted this parameter. Results of this experiment are shown in FIG. 4.

Figure 4:
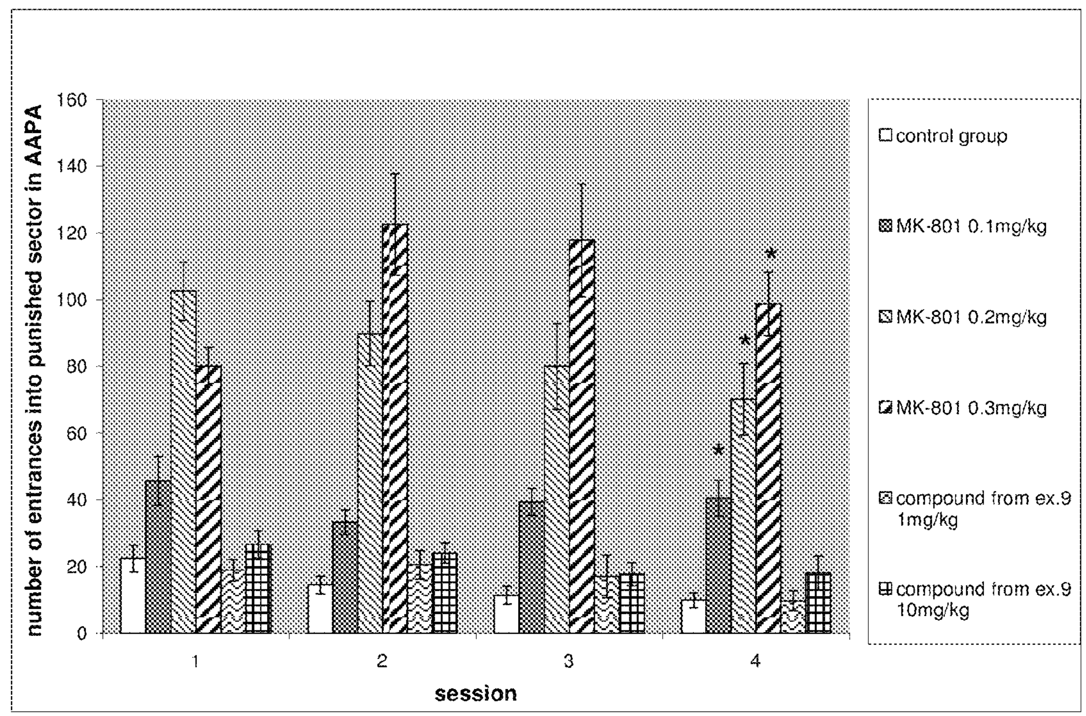
FIG. 4 shows number of entrances into the shock sector in the AAPA task in daily sessions as a measure of cognitive functions after administration of dizocilpine and compound from Example 9 (according to example 31). * denotes significant difference with respect to controls ($p<0.05$); statistical differences were estimated solely in the final session after the controls had reached the asymptotic level of performance.

FIG. 4 illustrates the number of entrances (as a measure of cognitive functions) in every AAPA session after application of dizocilpine and compound from Example 9. All doses of dizocilpine led to impairment in this parameter whilst compound from Example 9 did not cause a statistical change in this parameter in comparison with controls. * denotes $p<0.05$ compared to controls; statistical test performed for the final session (see above).

Example 32

Maximum Time Between Two Errors

Another spatially selective parameter indicating cognitive abilities is maximum time between two entrances, i.e. maximum time avoided. Dizocilpine at the three doses significantly decreased rats' performance; however, compound from Example 9 did not show this effect. Application of this compound did not significantly impaired cognitive performance compared to control animals. This part of experiment is graphically illustrated in FIG. 5.

Figure 5:
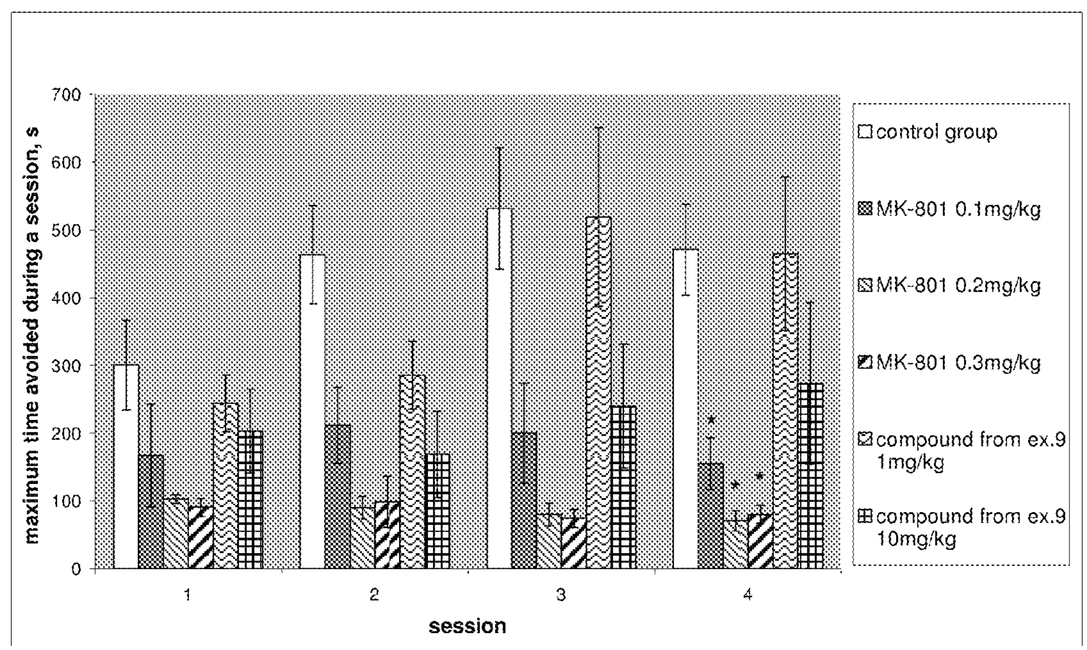
FIG. 5 shows the maximum time avoided per session in the AAPA task as a measure of cognitive functions after application of dizocilpine and compound from Example 9 (according to example 32). * denotes $p<0.05$ with respect to controls, statistical differences were evaluated in the last session at the asymptotic stage of control rats.

FIG. 5 shows the maximum time avoided in each session of AAPA training as a measure of cognitive functions after application of dizocilpine and compound from Example 9. All doses of dizocilpine significantly impaired this parameter, whilst compound from Example 9 did not produced any significant impairment. * denotes a significant difference compared to controls; statistical differences tested in the final session with asymptotic performance of control animals.

The following conclusion can be drawn from Examples 31-32: The results demonstrate that at given dose range (1-10 mg/kg) the compound from Example 9 does not significantly impair cognitive functions if applied alone. In this aspect it is very different from the effects of non-competitive NMDA receptor antagonist dizocilpine, which caused pronounced hyperlocomotion and cognitive deficit in the place avoidance task. These results show that compound from Example 9 at the mentioned dose range does not impair complex behavioral patterns, suggesting that it may not disturb basal synaptic activity necessary for these functions and could potentially be therapeutically usable if its neuroprotective properties were demonstrated (see below).

Example 33

Effect of Compound from Example 9 on Spatial Cognition after Bilateral Lesion of Hippocampus by N-methyl-D-aspartate (NMDA)

Neuroprotective action of 3α-substituted derivatives of pregnanolone was tested in the well-established model represented by excitotoxic bilateral lesion of the hippocampus with NMDA, an agonist of NMDA receptors. This model represents a widely-accepted paradigm of excitotoxicity induced experimental disruption of memory functions in laboratory rodents. The model also mimics into some extent the excessive action of glutamate on cells in the hippocampus, which contains abundance of NMDA receptors. The effect of lesions and possible neuroprotective action can be observed at various intervals after treatment both on the histological and behavioral level, provided that a suitable hippocampus-dependent memory task is available. In our studies, we have used a hippocampus-dependent spatial task AAPA (see above), which requires spatial and executive abilities and involves so-called "cognitive coordination" (Wesierska et al., 2005). Again, all manipulations with animals conformed to current legislation and Institutional recommendations on animal care and were approved by ethical-care committee.

In this phase of experiment, we have studied the effect of compound from Example 9 (and relation of this effect to dose) on NMDA excitotoxic hippocampal lesion after various intervals from lesioning. 150 adult male Long-Evans rats (250-350 g) were used in the study. Rats were housed in transparent plastic cages (25×25×40 cm) in air-conditioned animal room with 12/12 h dark/light rhythmicity. All rats had free access to food and water throughout the study.

During surgery, animals were deeply anesthetized by isoflurane inhalation anesthesia (3.5%, driven by air). Initial sedation was pursued in initiation chamber filled with diethyl ether vapor. During whole anesthesia, vital functions of animals were precisely monitored by the person pursuing surgery. After fixation in the stereotaxic apparatus (Kopf Instruments) the skull was exposed and small trephine openings were drilled with micro driller and subsequently, 1 ul of NMDA solution (0.09 mol NMDA in saline buffered with calcium dihydrogenphosphate to pH=7.2) was microinjected into both dorsal hippocampi. The stereotaxic coordinates (AP=4; L=±2.5; DV=4) were measured from a rigorous atlas (Paxinos and Watson, 2005) and later verified from histological examination. Rats were then placed into soft post-surgery boxes. Application of compound from Example 9 took place 1) 30 min prior to and 3 min after lesion, 2) 30 min after lesion, 3) 180 min after lesion, 4) 24 h after lesion. Doses of compound from Example 9 were: 0.01 mg/kg, 0.1 mg/kg and 10 mg/kg of b.w. In control groups and lesion-only groups, we applied only saline and NMDA, respectively. Solution of compound from Example 9 (0.01 mg/2 ml, 0.1 mg/2 ml or 10 mg/2 ml dissolved in cyclodextrin) was applied s.c. at a volume of 2 ml/kg.

Prior to behavioral observations, animals were left for 7 days to recover after surgery. After this recovery period, two days (each consisting of two sessions) of AAPA training were conducted. Each rat was initially placed onto rotating (1 rpm) circular arena containing a to-be-avoided sector (60°), fixed in the coordinate frame of the room (Stuchlik et al., 2008). Upon entrance into the prohibited sector, rat was punished by a mild electric footshock (~0.3 mA] delivered from low-impedance subcutaneous wire to contact between rats paws and grounded floor (with highest voltage drop in rats feet). Rats wore a latex harness on their backs, holding an infrared light-emitting diode (LED), which was sampled by TV camera mounted above the arena and connected to a computer digitizing system (iTrack, Biosignal Group, USA). The shock sector is not directly perceptible for animals and its location can be determined solely by its relationships with distal room landmarks. To efficiently manage the task, animals should possess spatial learning abilities, oriented attention, and cognitive coordination (Wesierska et al., 2005). The task is highly dependent upon hippocampus, with unilateral inactivation of this structure leading to avoidance deficit (Cimadevilla et al., 2001). This was the reason why we have selected this task for NMDA-induced impairment and detection of putative neuroprotective action of our compound (Example 9).

TrackAnalysis software (Biosignal Group, USA) was used to analyze the raw data. The program allows detailed analysis of animals' trajectories. Number of entrances into shock sector as well as maximum time avoided reflects the strength of memory trace and behavioral performance and can be used for assessment of cognitive functions.

Application of NMDA alone led to a marked hippocampal lesion and to disruption of behavioral performance in the subsequent AAPA testing compared to control animals. Potential alleviating (and thus neuroprotective) action of our compound at various doses and after various intervals from lesion are summarized in the following Examples. Graphs show means and standard errors of the mean (S.E.M.) in the final session, when control animals are at the asymptotic levels.

Example 34

Effect of Compound from Example 9 on the Number of Entrances into Shock Sector in Lesioned Animals The compound from Example 9 at a dose 0.01 mg/kg improved the subsequent performance in the AAPA task measured as number of entrances when applied at a delay of 30 min after lesion. It is interesting to point out that if the compound was administered 30 min prior to and after lesion, the alleviation was not significant. The compound exerted no effect after longer intervals from the lesion. Results of these experiments are summarized in FIG. 6.

Figure 6:
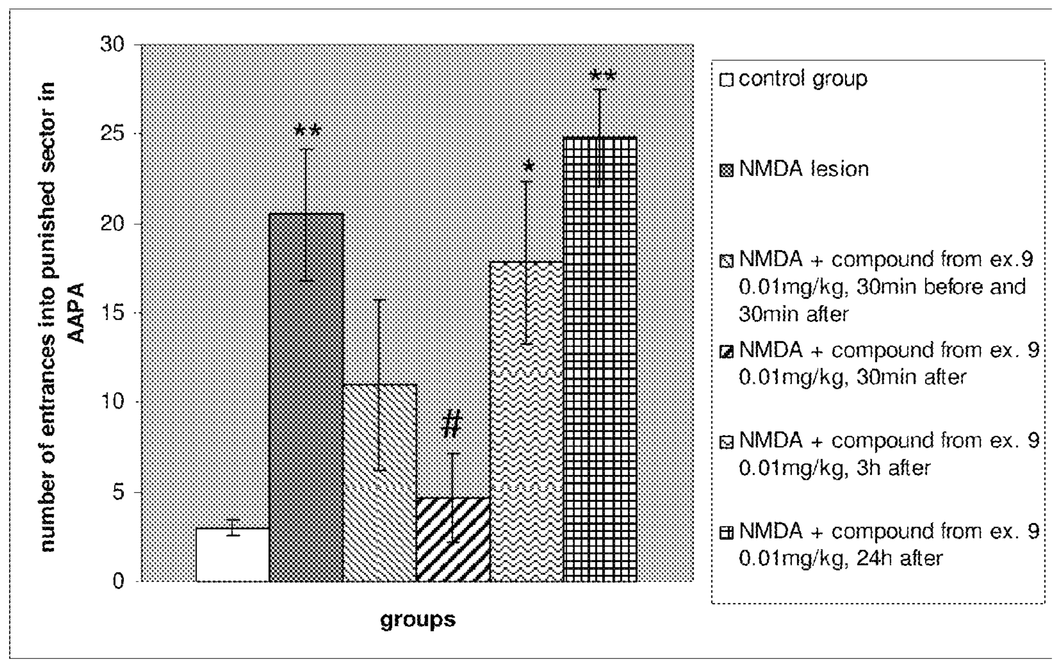
FIG. 6 shows the effect of compound from Example 9 at a dose of 0.01 mg/kg on the Number of entrances in subsequent AAPA testing (according to example 34). # $p<0.05$ with respect to NMDA alone, * p<0205 with respect to controls; ** $p<0.01$ compared to controls.

FIG. 6 shows the effect of compound from Example 9 at a dose 0.01 mg/kg on the number of entrances during subsequent testing in the AAPA task. A dose 0.01 mg/kg applied 30 min after lesioning ameliorated the rats' performance compared to animals with hippocampal lesion, but no treatment with our compound.

Example 35

Figure 7:
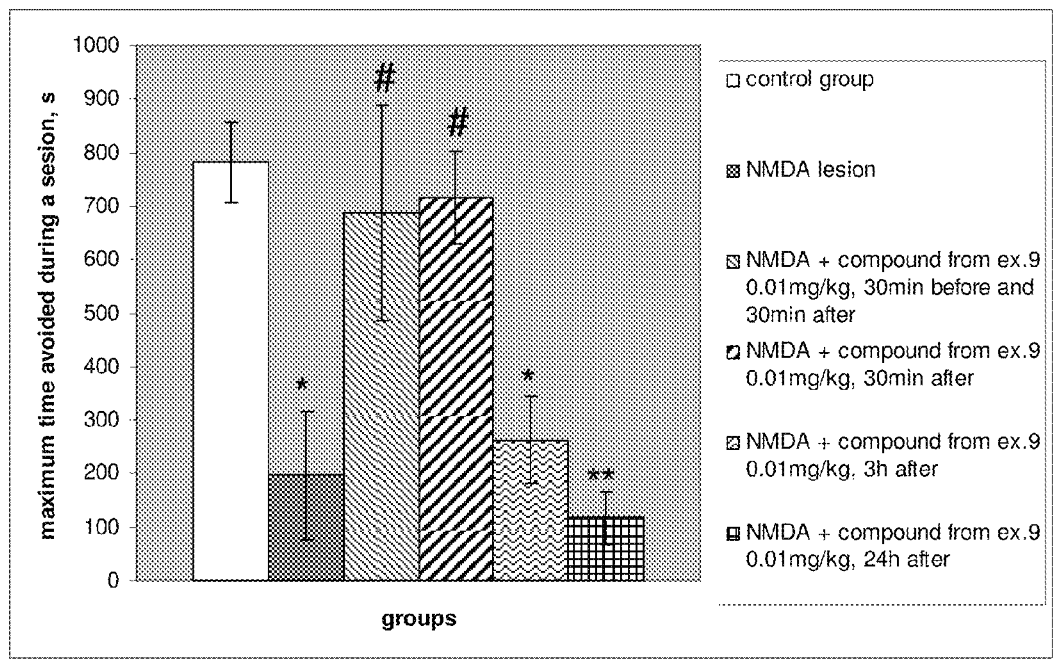
FIG. 7 shows the effect of compound from Example 9 at a dose 0.01 mg/kg on the maximum time avoided during AAPA testing (according to example 35). # $p<0.05$ with respect to NMDA alone; * $p<0.05$ with respect to controls, ** $p<0.01$ with respect to controls.

Effect of Compound from Example 9 at a Dose 0.01 mg/kg on the Maximum Time Avoided The compound from Example 9 had beneficial effect in lesioned animals when applied 30 min after lesion and also when administered at two doses 30 min both prior to and after lesion with NMDA. The results are shown in FIG. 7, which illustrates the effect of our compound at a dose 0.01 mg/kg on the maximum time avoided during subsequent AAPA testing.

A dose 0.01 mg/kg administered either 30 min prior to and 30 min after lesion or 30 min after lesion improved the performance in this parameter compared to animals with NMDA lesion only.

These results suggest that the above mentioned dose of our compound exert neuroprotective properties on the behavioral level.

Example 36

Effect of Compound from Example 9 on the Number of Entrances

Figure 8:
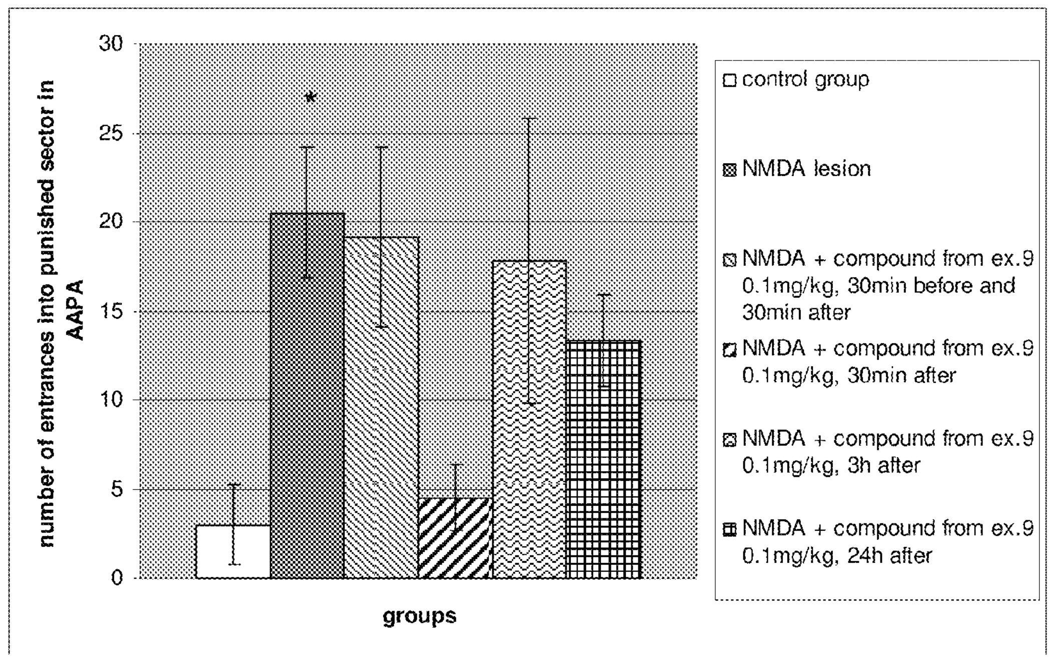
FIG. 8 shows the effect of the compound from Example 9 at a dose 0.1 mg/kg on the number of entrances into shock sector during AAPA testing (according to example 36); * $p<0.05$ with respect to controls.

A dose 0.01 mg/kg of our compound tended to exert a (non-significant) ameliorating effect on the number of errors only when applied 30 min after lesioning, as is shown in FIG. 8. Animals applied with a dose 0.1 mg/kg of our compound exhibited similar mean values as control animals; however, large variances in the measured groups likely prevented the result from being significant. The results of this experiment are illustrated in FIG. 8, which shows the effect of our compound on the number of entrances into punished area during subsequent AAPA testing. A dose 0.1 mg/kg administered 30 min after lesion non-significantly improved the behavioral performance compared to animals with NMDA lesion only.

Example 37

Figure 9:
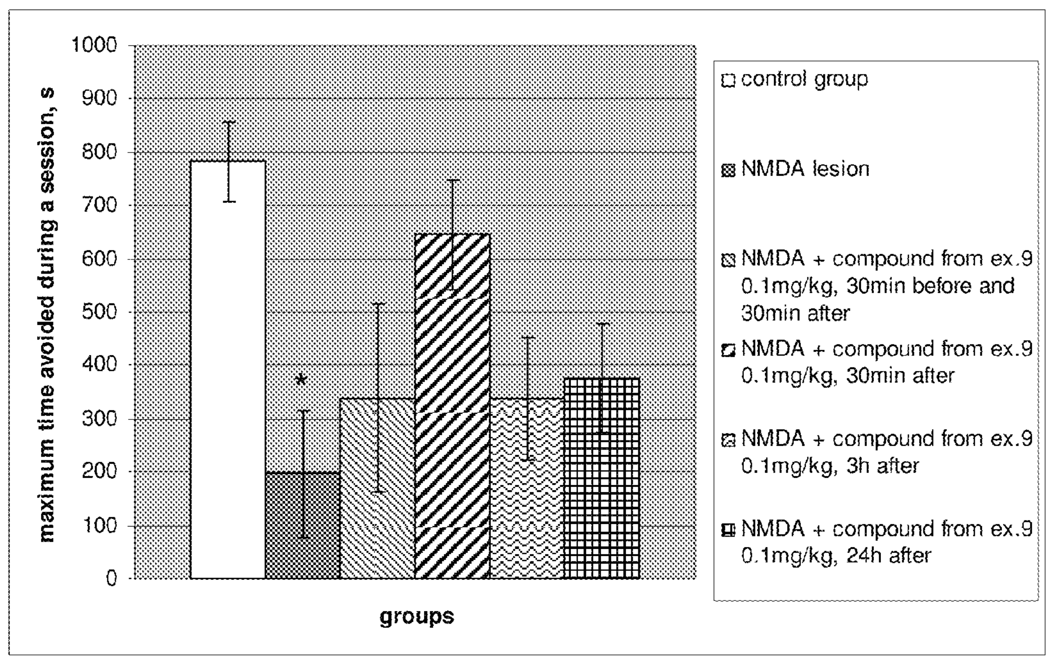
FIG. 9 shows the effect of the compound from Example 9 on the maximum time avoided during AAPA testing (according to example 37).

Effect of Compound from Example 9 at a Dose 0.1 mg/kg on the Maximum Time Avoided Similar results were obtained also for maximum time avoided, as is shown in FIG. 9, which illustrates the effect of compound from Example 9 at a dose 0.1 mg/kg on the maximum time avoided during subsequent training in the AAPA task. Dose 0.1 mg/kg of our compound tended to alleviate the performance of rats compared to lesioned animals without treatment, although this difference failed to reach statistical significance.

Example 38

Effect of Compound from Example 9 at a Dose 10 mg/kg on the Number of Entrances in the AAPA Task The compound from Example 9 at a dose 10 mg/kg had a significant protective effect against hippocampal lesion only in cases, when it was applied at two doses (30 prior to and after lesion) and single dose (120 min after lesion). No improvement was seen at other delays, as is shown in FIG. 10.

Figure 10:
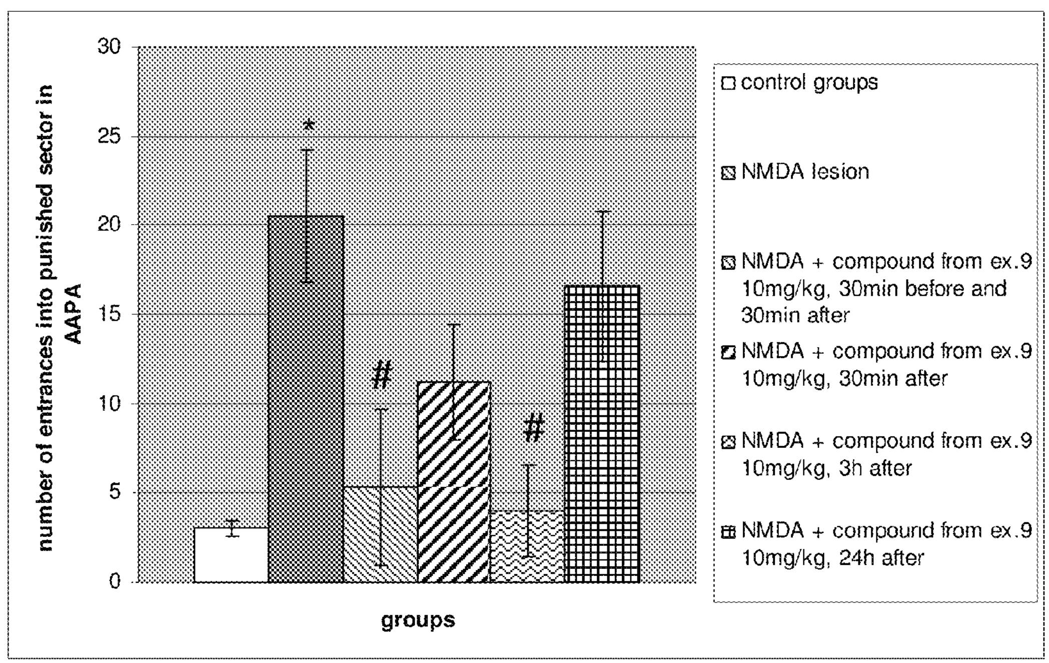
FIG. 10 shows the effect of the compound from Example 9 on the total number of entrances into shock sector in the AAPA testing (according to example 38); # $p<0.05$ compared to NMDA alone, * $p<0.05$ compared to controls.

FIG. 10 illustrates the effect of compound from Example 9 at 10 mg/kg on total number of entrances into shock sector during subsequent AAPA learning. A dose 10 mg/kg of our compound exerted an ameliorating effect when applied either 30 min prior to+after lesion or 120 min after NMDA lesion.

Example 39

Effect of Compound from Example 9 at a Dose 10 mg/kg on Maximum Time Avoided

Figure 11:
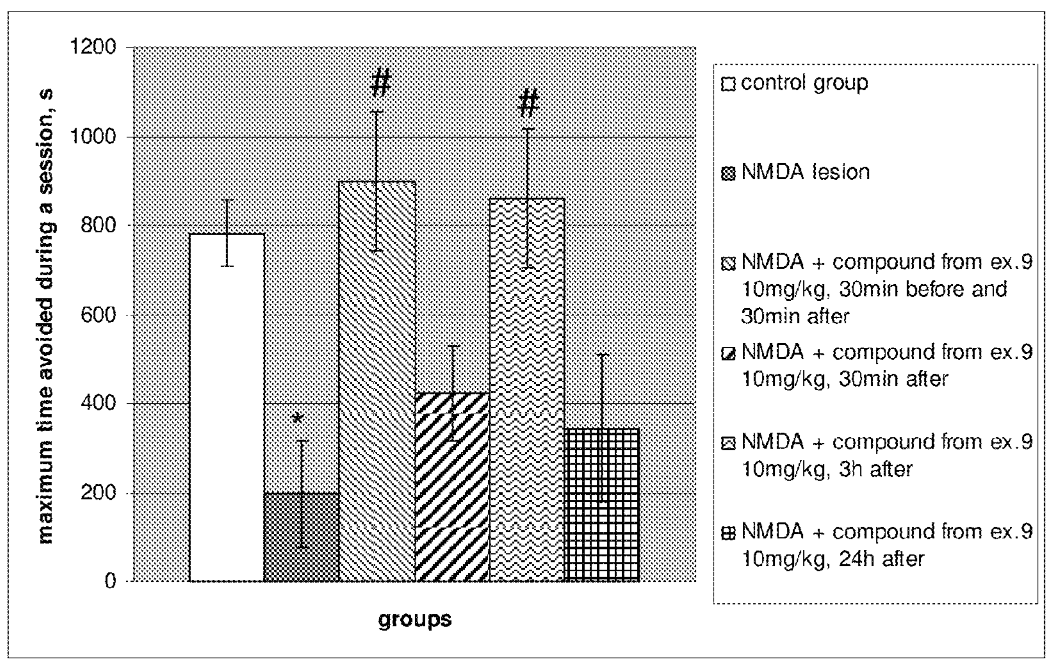
FIG. 11 shows the effect of the compound from Example 9 on the maximum time avoided in the AAPA daily sessions (according to example 39). # $p<0.05$ with respect to NMDA alone, * $p<0.05$ with respect to controls.

Analysis of the maximum time avoided (another very important spatial parameter in the AAPA task) has revealed that this dose of our compound exerted a protective effect at the same intervals as for the number of entrances (see previous paragraph) as is shown is FIG. 11, which illustrates the effect of compound from Example 9 at a dose 10 mg/kg on the maximum time avoided per session in subsequent AAPA testing. A dose 10 mg/kg applied 30 min prior to and after lesion and also 120 min after lesion caused a significant improvement of rat performance compared to NMDA-lessened animals without treatment.

From previous Examples (31-37) one can infer, that compound from Example 9 can, in combination with specific treatment schedules, improve the cognitive functioning of animals in comparison with animals, which were subjected to lesion, but not to the treatment with compound from Example 9. This bulk of behavioral experiments suggest a potential neuroprotective action of compound from Example 9 on this model of spatial learning after excitotoxic hippocampal lesion.

Example 40

Histochemical Analysis after Bilateral NMDA-induced Hippocampal Lesion

Animals were divided into four groups consisting of two series. First group of animals received an application of NMDA (intrahipocampally, i.h.) and compound from Example 9 (1 mg/kg, i.p.). Second group received NMDA i.h. and cyclodextrine i.p., third group obtained saline i.h. and cyclodextrin i.p. Forth group was applied with sterile saline i.h. and compound from Example 9 at a dose 1 mg/kg, i.p. Six animals from each group was sacrificed and perfused at intervals of 1-4 days after experimental manipulation.

Animals were deeply anesthetized by isoflurane (3.5%, driven by air) and fixed in the stereotaxic apparatus. Small drills were made in the skull and subsequently microinjection of NMDA (1 μl, 0.09 mol NMDA in saline; pH adjusted to 7.2 by calcium dihydrogenphosphate) into both hippocampi was pursued. Coordinates of application (AP=4, L=2.5, DV=4) were localized with stereotaxic atlas (Paxinos and Watson, 2005) and verified in histological controls. Rats were again placed in soft recovery boxes after surgery and carefully monitored after surgery.

Application of compound from Example 9 was done according to experimental scheme either 30 min prior to and after NMDA application (in first series of experiments) or 30 min after lesion in the second series. Animals were perfused on days 1-4 after lesion, their brains were fixed with paraformaldehyde and sacharose solution. The brains were subsequently frozen to −70° C., and thin brain slices were prepared on cryomicrotome, stained and analyzed under light microscope.

After administration of NMDA, FluoroJadeB staining showed bilateral damage of hippocampal formation within dentate gyrus, CA1-CA3, intense staining in CA2 a dentate regions and to lesser extent in subiculum, entorhinal cortex and in prepiriform and piriform cortices. In neocortex lying within frontal and parietal lobes the cortical layers 2-5 was cytoarchitectonically altered, layer 6 was stained into lesser extent. Most prominent staining was observed in pyramidal neurons and small interstitial neurons of layer 4. Minor damage of basal ganglia (caudatoputamen) and thalamus in the region of reticular nucleus was observed. Dorsal hippocampal regions showed significantly more intense staining than supracomissural and ventral parts of hippocampus.

After application of compound from Example 9 we have observed significant decrease of NMDA-induced damage to the hippocampus, mainly in dentate gyrus and all *Cornu ammonis* fields and subiculum. Associated cortical regions (entorhinal and piriform cortices) retained hardly-quantifiable damages in archicortical layers 2 and 3 in a large extent reaching the borders of olfactory structures. We observed a pronounced cessation of damage in the whole neocortex—visual, auditory and sensorimotor cortices. Alleviation, but not elimination of damage was observed in caudatoputamen and thalamic nuclei. In both cases, co-localization in the confocal microscope with DAPI showed specific damage to neurons; glial cells were spared. These results convincingly confirm the notion that compound from Example 9 posses a neuroprotective action on the hippocampal damage by means of intrahippocampal application of NMDA.

Example 41

Pharmacokinetic Properties of the Compound from Example 9

In the experiment 40 adult Long-Evans male rats from breeding colony of Institute of Physiology AS CR v.v.i., Prague were used. Rats were treated i.p. with a dose 1 mg/kg of compound from example 9 dissolved in 72 mM of hydroxypropyl-β-cyclodextrine saline solution. Brain and plasma was taken 5 min, 15 min, 30 min, 45 min, 60 min, 90 min, 120 min, 180 min, 24 hours and 48 hours after drug administration. Each brain and blood samples were taken from separate rat. Samples were collected in 4 rats for each time interval. Samples were immediately stored in a −80° C. freezer.

The concentrations of compound from example 9 in rat brain and plasma samples were measured by high performance liquid chromatography (HPLC) coupled with mass spectrometry (Agilent 6320 Ion Trap). Deuteried internal standard ($3_{-d}$ labeled compound from example 9) has been used for ensuring high accuracy of measurement.

Figure 12:
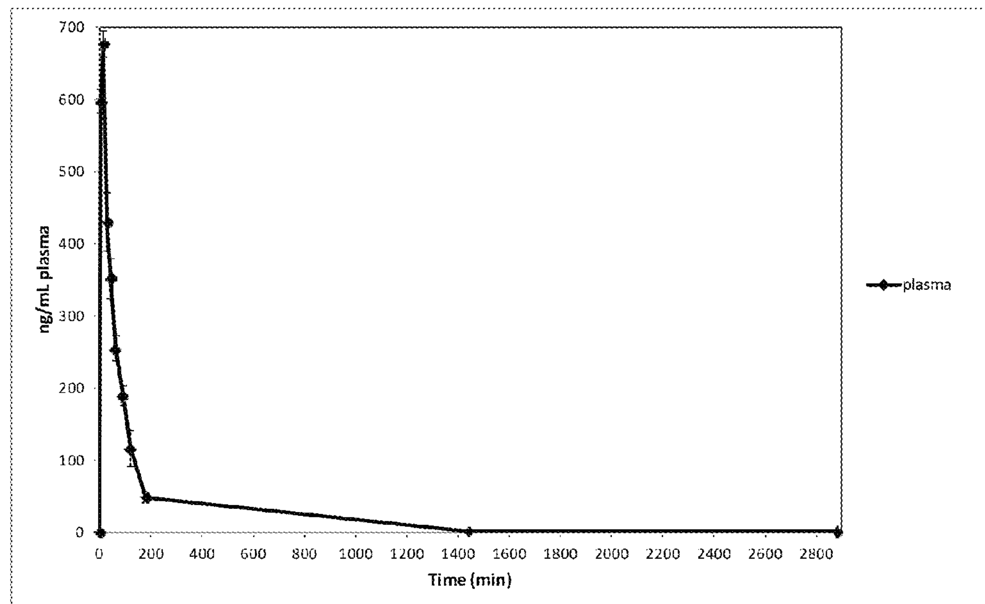
FIG. 12 shows the time course of compound from example 9 concentration in plasma of rats (ng/ml) after i.p injection thereof (1 mg/kg) according to Example 41. At the y-axis concentrations of above mentioned compound in plasma are outlined as ng of the compound contained in 1 ml of plasma. At the x-axis the time is outlined as minutes (hours).
Figure 13:
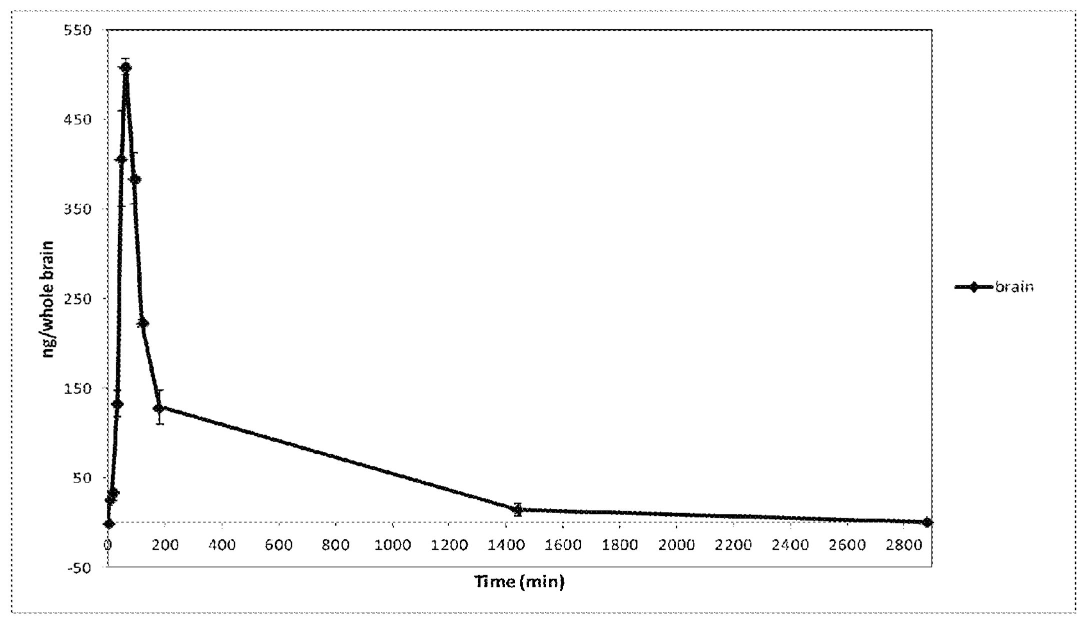
FIG. 13 shows the time course of compound from example 9 level in rat brain (ng/whole brain) after i.p injection thereof (1 mg/kg) according to Example 41. At the y-axis levels of above mentioned compound in brain are outlined as ng of the compound contained in whole brain. At the x-axis the time is outlined as minutes (hours).

Following the intraperitonal injection of compound from example 9 (1 mg/kg) its $c_{max}$=675 ng/ml in plasma at the time of $T_{max}$=15 min was detected. The compound from example 9 penetrates blood brain barrier and rapidly enter the brain ($T_{max}$=60 min, $c_{max}$=508 ng/whole brain) after i.p injection of compound from example 9 (1 mg/kg) and exponentially decreases to a mean (4 rats in the group) of 222 ng/whole brain after 2 hours, 128 ng/whole brain after 3 hours, 14 ng/whole brain after 24 hours and 0.6 ng/whole brain after 48 hours. It seems that the compound from example 9 is eliminated by a first-order process and it is not cumulated in brain tissue. FIGS. 12 and 13 show the plasma and brain levels of compound from example 9.

Example 42

Toxicology of the Compound from the Example 9 in Rat Model of Acute Toxicity Toxicity of compound from example 9 was tested on 2-month-old Long-Evans male rats. Animals were randomly assigned to 4 groups per 7 animals each. The first group was injected i.p. with saline, the second group received i.p. cyclodextrine, the third group obtained received the compound from example 9 at a dose 1 mg/kg (dissolved in β-cyclodextrine) and the last group compound from example 9 at a dose 100 mg/kg (dissolved in β-cyclodextrine). Animals were monitored for the period of 5 days. At the end of the experiment macroscopic dissection was carried out and organs were weighted (brain, heart, liver, spleen and kidneys). Animals' weight, food and water consumption was monitored daily. At the same time the behavior and locomotor activity was observed and animals were inspected for detection of effusions, constipation, etc.

Figure 14:
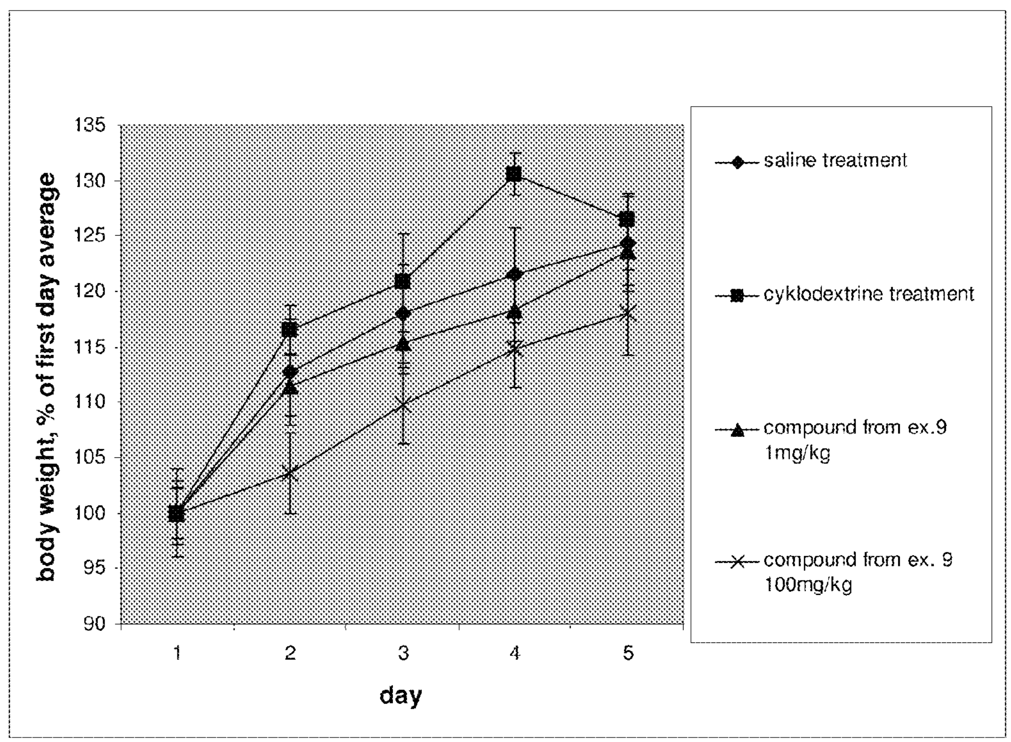
FIG. 14 shows the effect of compound from example 9 on the body weight of rats in time according to Example 42. The compound was applied on day 1 at a single dose of either 1 mg/kg or 100 mg/kg. At the y-axis levels body weight in % of first day average are (symbol -♦- for saline treatment, symbol -■- for cyclodextrine treatment, symbol -▲- for compound from exp. 9 (1 mg/kg) treatment, symbol -x- for the same compound (100 mg/kg). At the x-axis the time is outlined as days.

There were no differences among the groups regarding in weight gain; overt behavior, locomotor activity, food and water consumption and no effusions and constipation were detected during 5-day period. During the macroscopic dissection no differences between groups were observed and no differences were found between groups in organ weights. On the day of application (15 minutes after injection) decreased locomotor activity was registered in the fourth group (receiving i.p. 100 mg/kg of compound from example 9 dissolved in cyclodextrine). Decreased locomotor activity gradually changed into anesthesia of animals (45 minutes after injection). Animals spontaneously awoke after 4 hours and they showed no problems for the rest of the experiment. Anesthetic effect may be related to the mechanism of action of this compound. FIG. 14 shows the effect of compound from the example 9 on the body weight curve measured over short interval. The compound was applied on day 1 at a single dose of either 1 mg/kg or 100 mg/kg.

Body weights were monitored daily and on day 5, animals were sacrificed and examined. The slight increase in β-cyclodextrine-treated animals probably represents between-group inhomogeneity; note that the compound from example 9 at lower dose failed to affect short-term body weight gain, the higher dose tended to decrease it slightly.

Figure 15:
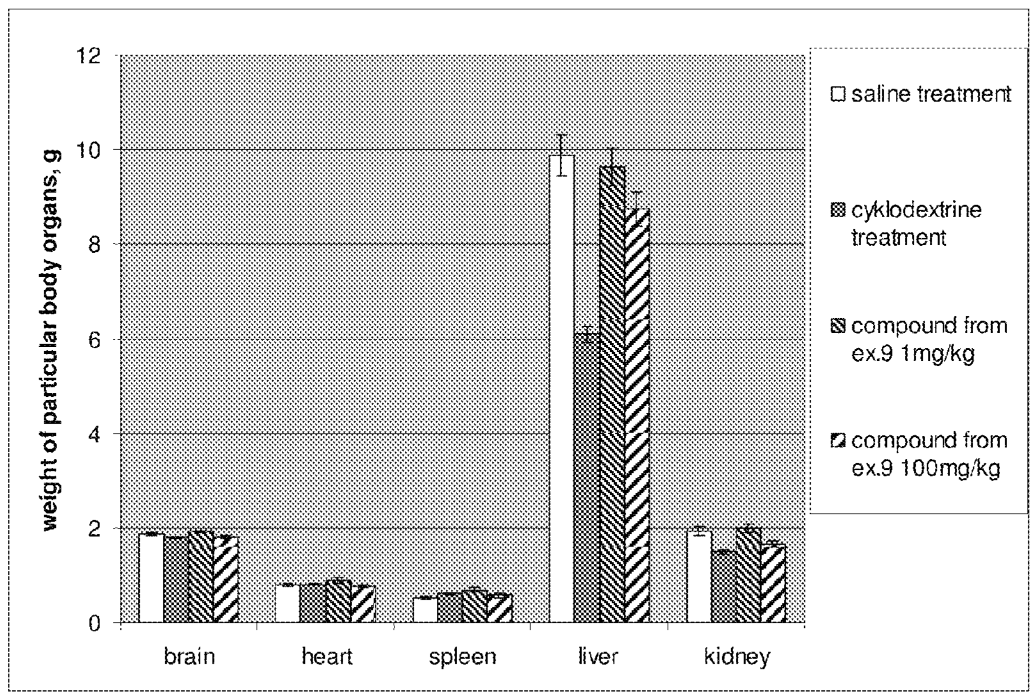
FIG. 15 shows the effect of compound from example 9 on the weight of particular body organs in rats according to Example 42. At the y-axis weight of particular body organs in grams are outlined. At the x-axis the particular organs are mentioned and type of treatment used (first column for saline treatment, second column for cyclodextrine treatment, third and fourth column for compound from example 9 treatment in the doses of 1 mg/kg of b.w. and 100 mg/kg of b.w. respectively).

FIG. 15 shows the effect of compound from example 9 on the weight of particular body organs. The compound was injected on day 1 and organs were weighted on autopsy on day 5. Note that there were no differences between controls and animals treated with the compound from example 9. The slight decrease of liver weight in β-cyclodextrine-treated animals probably represents between-group inhomogeneity.

In conclusion compound from example 9 after i.p. administration in doses up to 100 mg/kg does not exhibit any signs of acute toxicity in laboratory rat.

Example 43

Effect of Compound from Example 9 on the Cells in Glioma-cell Culture

The effect of compound from the example 9 (the model molecule) on growth of glioma cells was studied on C6 glioma cell line (ATTC, Rockville). The model molecule was tested at doses of 0.1 and 1 μg dissolved in 50 ml of β-cyclodextrine solution. Parallel control groups were administered by cholesterol at doses of 0.1 and 1 μg dissolved in 50 ml of β-cyclodextrine solution. The last group included in the experiment was left intact without any application.

Figure 16:
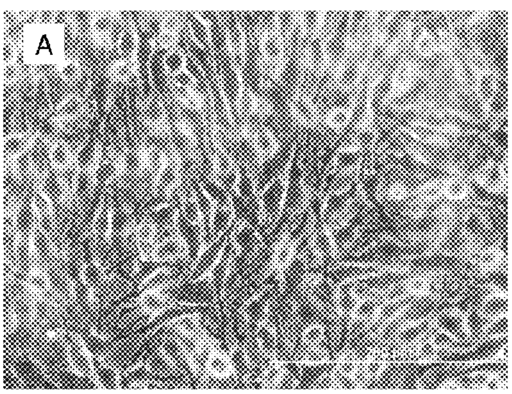
FIGS. 16 C and 16D represent groups of C6 glioma cell lines administered by the compound of Example 9 at doses of 0.1 and 1 μg respectively dissolved in 50 ml of β-cyclodextrine solution.
Figure 16:
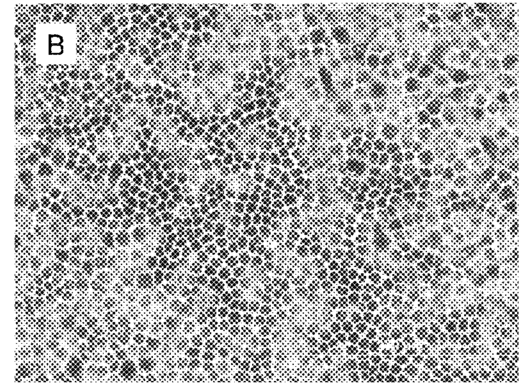
Figure 16:
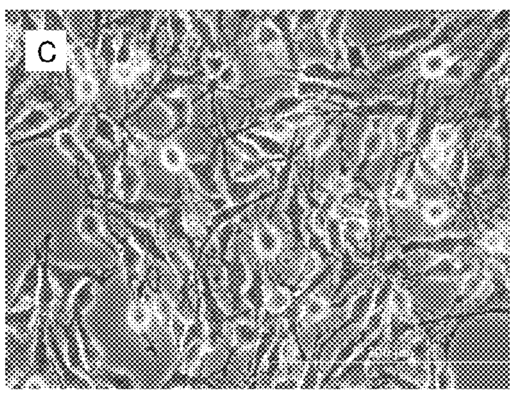
Figure 16:
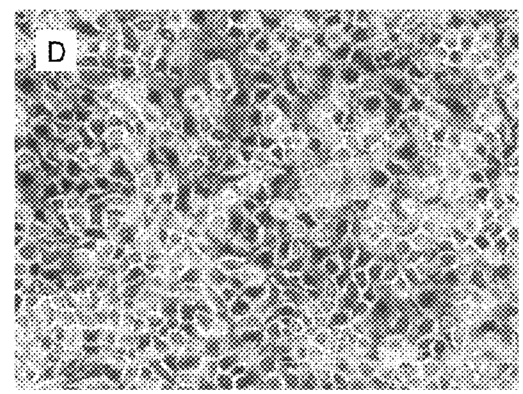

The cells were cultivated in vitro for 3 days (div). Afterwards tested molecule was applied and the cell culture was studied for additional 6 days. Olympus microscope with phase contrast and 200× magnification was used for the cell monitoring. Results are shown in FIG. 16.

24 Hours after application the cells produce thinner radial projections. Later (3-6 div) the cell growth was lower compared to controls. At the same time cells hypertrophy was observed. Faster acidification of cultured medium implies the possibility of metabolic acceleration in the cell population. The compound from example 9 (dissolved in solution of β-cyclodextrine) has overall slight cytostatic and pro-differentiation effect on glioma cells studied in vitro compared to controls. The effect was slightly apparent in control groups injected with cholesterol (dissolved in solution of β-cyclodextrine); but it was significantly smaller. Similar effects of compound from example 9 and cholesterol on glioma cells was due to sterane component they share, however the effects of the compound from example 9 (dissolved in solution of β-cyclodextrine) are significantly amplified. These results support the potential effect of the compound from example 1 on glioma cells in an in vitro model.

Example 44

Effect of Compound from Example 9 on Anxiety Bahavior in Elevated Plus Maze

The effect of i.p. administration of compound from example 9 in doses of 0.001, 0.01, and 10 mg/kg on behaviour in elevated plus maze was evaluated. The number of entrances into open arms and the total time spent in open arms were assessed.

The apparatus consisted of two opposite open arms (45 cm×10 cm) crossed at right angles with two opposite arms of the same size enclosed by walls 40 cm high, except for the central part where the arms crossed. The whole apparatus was elevated 50 cm above the floor.

Figure 17:
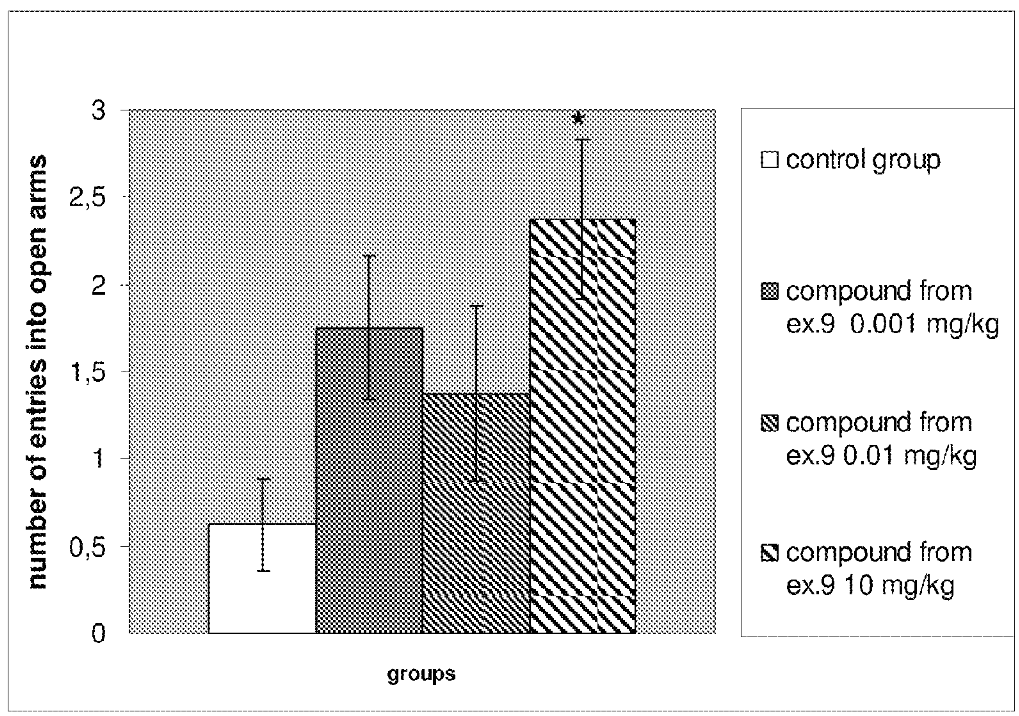
FIG. 17 demonstrates effect of compound from example 9 application in doses of 0.001 mg/kg, 0.01 mg/kg, and 10 mg/kg to rats in elevated plus maze according to Example 44. At the y-axis the number of entries into open arms of maze is mentioned. At the x-axis the group of tested animals are mentioned; first column represents controls, 2.-4. column represents groups of animals administered by above mentioned compound at the dose of 0.001, 0.01 and 10 mg/kg of b.w. respectively.

Results showed that administration of the compound from example 9 exerted pronounced dose-dependent anxiolytic effect, as can be seen in FIG. 17. While tested on elevated plus maze, rats from control group only rarely entered open arms, thereby demonstrating some degree of anxiety. Application of compound from example 9 had apparent anxiolytic effect; however, only application of compound from example 9 at dose 10 mg/kg led to significant increase of number of entries into open arms (* $p<0.05$, compared to control group).

Example 45

Effect of the Compound from Example 9 on Footshock-induced Ultrasonic Vocalization as a Model of Anxiety Effect of compound from example 9 application at doses of 0.001 mg/kg, 0.01 mg/kg and 10 mg/kg on ultrasonic vocalization after exposure to stressful situation (foot-shock) as a measure of anxiety. Under conditions of stress and pain, rats are known to emit ultrasonic distress calls at a frequency of about 22 kHz. Under conditions of stress and pain, rats are known to emit ultrasonic distress calls at a frequency of about 22 kHz. On the first day, rats were placed into the shock chamber individually and after 30 s of habituation, they received 6 inescapable electric foot-shocks (1 shock/1 minute, 1 mA) of 10 seconds duration. The procedure was repeated 24 hours later, but this time, the animals received only one 10-second shock. Afterwards, the rats were injected i.p. with vehicle (b-cyclodextrine) or the compound from example 9 at doses of 0.001, 0.01, and 10 mg/kg) 30 min prior to testing. During the test session, animals were placed into the shock chamber for 10 minutes and their ultrasonic vocalization was recorded. No foot-shocks were delivered during the test session. Each animal was recorded separately with a Mini-3 Bat Detector (Ultra Sound Advice, London, UK). Ultrasonic vocalizations at 22-kHz consisting of calls with a minimal duration of 300 ms were recorded and analyzed by UltraVox 2.0 program (Noldus, Wageningen, The Netherlands). The total number of vocalization events and their total duration were recorded.

Figure 18:
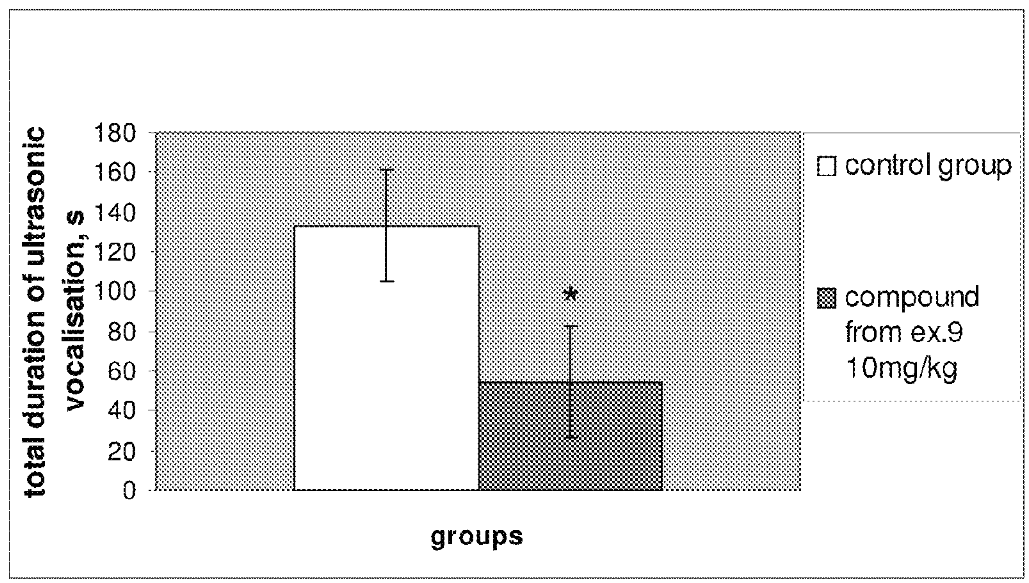
FIG. 18 shows total duration of ultrasonic vocalizations as a model of anxiety according to Example 45. At the y-axis total time of ultrasonic vocalizations in seconds is outlined.

The results confirm slight dose-dependent anxiolytic effect the compound from example 9. Significant difference is manifested only in the highest dose of 10 mg/kg, as can be seen in FIG. 18.

Example 46

Effect of the Compound from Example 9 on Prepulse Inhibition of the Startle Response in Combination with Dizocilpine in an Animal Model of Schizophrenia Since the ethiopathology of schizophrenia is not fully understood, it is difficult to establish its animal model with full construct validity. Recently proposed models are based on the central blockade of glutamate receptors, namely their NMDA subtype. Administration of compounds which block NMDA receptor (MK-801, phencyclidine, ketamine) elicits a psychotic state when applied to healthy humans and worsens psychotic symptoms when administered to schizophrenic patients. Administration of high-affinity non-competitive NMDA receptor antagonist MK-801 (dizocilpine) was proposed as an animal model of schizophrenia, which proved to have relatively high predictive and phenomenological validity. Animals treated with MK-801 exhibit typical changes in behaviour including hyperactivity, defective habituation, impaired attention, simpler behavioural repertoire and general behavioural primitivization. Some of these symptoms can be compensated by classical and atypical antipsychotic treatment.

Behavioural effects of antipsychotic agents have been intensively studied in pre-clinical models of schizophrenia-like behaviour. Major tests used are open field (locomotor activity), prepulse inhibition of startle response (sensorimotor gating), and learning and memory paradigms.

The effect of i.p. administration of the compound from example 9 at doses of 0.1 and 1 mg/kg on sensorimotor gating in prepulse inhibition (PPI) test was evaluated. All testing occurred within the startle chamber (SR-LAB, San Diego Instruments, USA), which consisted of a clear Plexiglas cylinder (8.2 cm diameter, 10×20 cm) that rested on a piezoelectric accelerometer inside a ventilated and illuminated chamber. The piezoelectric accelerometer detected and transduced motion within the cylinder. A high frequency loudspeaker inside the chamber (24 cm above the animal) produced both a background noise of 62 dB and the acoustic stimuli. All rats were initially tested in a short session (5 min acclimatization period plus 5 single stimuli; 120 dB strong) 2 days before the experiment.

The background noise (62 dB) was presented alone for 5 min (acclimatization period) and then continued throughout the session. After the acclimatization period, the test began with five initial startle stimuli followed by four different trial types presented in a pseudorandom order: (1) single pulse: 120 dB broadband burst, 20 ms duration; (2) prepulse: 13 dB above the background noise, 20 ms duration were presented 100 ms before the onset of the pulse alone; (3) prepulse alone: 13 dB above the background noise, 20 ms duration; (4) no stimulus. A total of five presentations of each trial type were given with an interstimulus interval of approximately 30 s. The PPI was measured as a difference between the average responses to the single pulse and prepulse-pulse trials, and was expressed as a percent of the PPI [100−(mean response for prepulse-pulse trials/startle response for single pulse trials)×100]. In addition, four single pulse trials at the beginning of the test session were not included in the calculation of the PPI values. We have studied the effect of MK-801 and compound from example 9 after combined and separate administration.

The results have shown that MK-801 disrupts PPI. Application of the compound from example 9 to animal with induced schizophrenia-like state significantly dose dependently improves deficit in PPI. Application of compound from example 9 alone has shown no effect on sensorimotor gating measured in this paradigm (see FIG. 19). Prepulse inhibition was considerably disrupted after MK-801 0.1 mg/kg treatment (** $p<0.01$, compared to control group). However, co-administration with either compound from example 9 at dose 0.1 mg/kg or 1 mg/kg blocked the exacerbating effect of MK-801. Application of compound from example 9 alone had no influence on prepulse inhibition.

Example 47

Effect of the Compound from Example 9 Alone or in Combination with Mk-801 on the Locomotion in the Open-field Behavior in an Animal Model of Schizophrenia The effect of the compound from example 9 in doses of 0.1 mg/kg and 1 mg/kg on locomotor activity in open field test was evaluated. Locomotor activity expressed as a total distance travelled during 30 min exploration of a box (68×68×30 cm) located in a sound proof room was measured using a video tracking system for automation of the behavioural experiments (Noldus, EthoVision, Version 2.1.).

The results have shown that contrarily to application of MK-801, administration of the compound from Example 9 did not produce locomotor alterations in the open-field test. However application of the compound from example 9 to animal with induced schizophrenia-like state has not effect on hyperlocomotion state induced by MK-801. To sum up the compound from example 9 has pro-cognitive effect without affecting of locomotor alterations (FIG. 20).

Example 48

Effect of the Compound from Example 9 on Behavior of Rats in the Active Allothetic Place Avoidance Task After Administration of MK-801 as an Animal Model of Schizophrenia (Locomotion)

The effect of compound from example 9 application on changes in behavior and locomotor activity in animal model of schizophrenia was monitored. Schizophrenia-like behavior in rats was induced by dizocilpine (MK-801) administration. Dizocilpine was administered in doses of 0.001 mg/kg, 0.01 mg/kg, 0.1 mg/kg and 10 mg/kg. Spatial orientation and cognitive function of rats were assessed in active allothetic place avoidance task (AAPA).

Schizophrenia-like behaviour in rats was induced by administration of dizocilpine (MK-801). Spatial navigation and cognitive functions of rats were assessed in active alothetic place avoidance task (AAPA). In addition, this task allows simultaneous assessment of potential differences in locomotory activity. The AAPA task requires rats moving on a continuously rotating (1 rpm) smooth metallic circular arena to avoid an unmarked place defined in the coordinates of the experimental room. The avoidance is reinforced by a mild electric foot-shock administered automatically upon entering the to-be avoided place.

The AAPA task is highly dependent on hippocampal function, since even a unilateral inactivation of thstructure hippocampus impairs this behaviour. Animals have to actively and repeatedly move away from the to-be-avoided place otherwise they are brought there by the arena rotation. Each AAPA session lasts 20 min and 4 sessions were conducted over 4 consecutive days.

Rats received 0.1 mg/kg MK-801 alone or co-administered with the compound from example 9 (dissolved in β-cyclodextrine) in doses of 0.001 mg/kg, 0.01 mg/kg, 0.1 mg/kg, and 10 mg/kg. Control animals received saline. While MK-801 shows neuroprotective effect in some experiments, it also produces cognitive deficits and hyperlocomotion in a state analogous to psychosis. It is for a common animal model of schizophrenia-like behaviour.

The results are shown in FIGS. 21-23, where means and standard errors of the mean (S.E.M.) are represented for individual sessions. Statistic analysis was for better clarity stated always for the last session, when an asymptotic level of performance in control animals was reached.

Locomotion activity in AAPA task was evaluated as a total distance travelled in the arena during 20-minute session. Animals that were given compound from example 9 at does of 0.001 mg/kg, 0.01 mg/kg and 0.1 mg/kg showed neither increase nor decrease of locomotion activity in any of the doses used in comparison to control rats. The only exception was the dose of 10 mg/kg that increased locomotor activity compared to controls. Whereas the dose of 0.1 mg/kg MK-801 did not lead to enhanced locomotion, it is well known that higher doses (from 0.2 mg/kg) considerably increase locomotion.

In literature hyperlocomotion is often considered to be an experimental analogy of positive symptoms of psychosis because it is related to excessive functioning of dopamine system in mesolimbic brain regions. Evaluation of locomotion activity in AAPA task showed that compound from example 9 does not change this activity in all doses except that of 10 mg/kg. Results of locomotion activity measurements are pictured at the FIG. 21. Only the highest dose of the compound from Example 9 increased locomotor activity in combination with 0.1 mg/kg dizocilpine. This suggests that compound affect behavior only at highest dose in combination with psychotomimetic NMDA blocker.

Example 49

Effect of the Compound from Example 9 on the Number of Errors in the Aapa Task in Combination with MK-801 in an Animal Model of Schizophrenia The main measure of the avoidance behaviour is the number of errors (entrances into the to-be-avoided place. Administration of MK-801 (0.1 mg/kg) resulted in marked impairment of this parameter. Co-administration of the compound from example 9 reversed this deficits at all doses. The results are summarized in FIG. 22.

Graph shows the number of errors (entrances into restricted sector) as a measure of cognitive functions for every session in AAPA task after application of saline, dizocilpine 0.1 mg/kg alone or in co-application with compound from example 9. All of compound from example 9 doses resulted in improvement of cognitive deficits induced by dizocilpine administration.

Example 50

Effect of the Compound from Example 9 on Maximum Time of Avoidance in the AAPA Task in Combination with MK-801

The maximum latency between two errors is another measure of the avoidance. MK-801 (0.1 mg/kg) produced a significant deficit in this parameter. Co-administration of the compound from example 9 reversed this deficit in doses of 0.001, 0.01, and 10 mg/kg. The results are summarized in FIG. 23.

Graphs show the maximum time of avoidance as a measure of cognitive functions for every session in AAPA task after application of saline, MK-801 alone or in co-application with compound from example 9. MK-801 application resulted in worsening of this parameter; on the other hand application of compound from example 9 at doses of 0.001 mg/kg, 0.01 mg/kg, 0.1 mg/kg and 10 mg/kg led to statistically significant change of cognitive functions.

In conclusion, the results from examples 21-23 indicate that the compound from example 9 reverses the cognitive deficit induced by MK-801. Hence, the compound from example 9 can be used to alleviate the cognitive deficit in an animal model of schizophrenia.

Example 51

Effect of the Compound from Example 9 on the Learned Helplessness in a Model of Affective Disorders Learned helplessness (LH) has been associated with several different psychological disorders. Depression, anxiety, phobias, shyness and loneliness can all be exacerbated by learned helplessness. Learned helplessness occurs when a subject is repeatedly subjected to an inescapable aversive stimulus. Eventually, animals will stop trying to avoid the stimulus and behave as utterly unable to change the situation. Even if opportunities to escape open, the learned helplessness prevents any action.

Male Long-Evans rats weighing 350-450 g were used. Animals were housed in groups in an air-conditioned room with 12 h/12 h light/dark cycle with the lights on at 7 a.m. Water and food were available ad libitum. Animals were randomly assigned to 3 groups—control group (received no shocks), learned helplessness group (received shocks) and experimental group (received shocks and injection of compound from example 9). An experimental set-up was composed of two chambers separated by a sliding door. The transparent shock chamber (48×20×20 cm) with one entrance led to the dark chamber (25×15×15 cm) made of black plexiglass. The floor of the shock chamber consisted of metal rods. Shocks were delivered through the grid floor. A shock generator (Data acquisition MF624 multifunction I/O board for PCI, Humusoft Ltd., Czech Republic) was connected to and controlled by a computer. On the pre-treatment day rats were individually placed into the apparatus for 10-minute habituation period. The sliding door separating two chambers was removed allowing free movements between the compartments. Immediately after the habituation rats were confined to the shock chamber for 1 hour. Inescapable shocks (72 V) of 10 s duration were delivered at 50 s intervals. Afterwards animals were injected i.p. with compound from example 9 in dose of 1 mg/kg. Control animals received no shocks during 1 hour shock session and animals from learned helplessness group received no drug. The next day, 24 hours later, each animal underwent escapable shock trials. The number of escapes was recorded. An escape failure referred to failed crossing response to the adjacent dark chamber during the shock delivery.

The application of the compound from example 9 significantly increased number of escapes. These results strongly support the potential antidepressant action of compound from example 9 (see FIG. 24). Experienced learned helplessness (LH) had a great impact on escapes performed in the LH apparatus. It considerably reduced number of attempts to escape (*** $p<0.001$, compared to control group). On the contrary, application of compound from example 9 fully blocked the debilitating effect of previous learned helplessness experience (## $p<0.01$, compared to LH group).

Example 52

Effect of the Compound from Example 9 on Forced Swim Test Used as the Experimental Model of Depression and Influence of Excessive Stress Forced swim test is an experimental model of depression and excessive stress used in laboratory rodents. Rats were randomly assigned to two groups of seven animals each. Control group received an injection of cyclodextrine (i.p.) 60 min. prior to experiment, while experimental group was injected i.p. with the compound from example 9 in a dose of 1 mg/kg 60 minutes prior to the experiment. Rats were forced to swim by being individually placed into a bucket (30 cm diameter, 28 cm height) containing water (25° C.). Immobility (floating) in the water is interpreted as a state of despair when the animals realize that an escape is impossible. Immobility was defined as floating (as opposed to active swimming) with minimal effort required for keeping the head above water. All animals received a single 30-minute trial and their behaviour was monitored by an experimenter. The trial was divided into six 5-minute intervals and floating of at least 30 second duration within each interval was recorded by the experimenter.

In conclusion, treatment of the compound from example 9 resulted in extended time of swimming. Rats from group treated by compound from example 9 (1 mg/kg) spent significantly less time by floating, in comparison to controls ($p<0.001$), as is apparent from longer average time to reach immobility (FIG. 25). Moreover in experimental group trials (all but one) needed not to be forcibly terminated due to animals sinking. The compound from example 9 exhibits antidepressant properties in forced swim test used as an animal model of depression.

Example 53

Effect of the Compound from Example 9 on Depression-like Behavior Induced by Social Defeat Glutamatergic neurotransmission plays an important role in stress response and development of mood disorders, depression, and other stress-related disorders. The aim of this experiment is to verify the hypothesis that treatment with the compound from example 9 affects behavioural response to chronic stress. A mouse model of repeated social defeat (non-aggressive male mice repeatedly defeated by aggressive counterparts) was used.

Naive adult male mice (albino out-bred strain ICR, VELAZ s.r.o., Prague, Czech Republic, 30-37 g) were used in this study. Food and water were available ad libitum. Mice were housed either individually without any handling in self-cleaning cages with a grid floor (8×6×13 cm) or in groups of 17-20 in standard plastic cages (38×22×14 cm) with the floors covered with wooden shavings. After 3 weeks, each individually housed mouse was allowed 30 min adaptation in a Plexiglas neutral observation cage (20×20×30 cm) with clean wooden shavings before it was coupled with a group-housed male partner for 4 min/day. As experimental subjects in Experiments 1 and 2 served the group-housed mice with or without defeat in four conflict dyadic interactions, the singly housed mice exhibiting aggressive behavioural activities were received 1 week apart. Numbers of attacks, tail rattling and threats exhibited by singly housed mice were recorded and evaluated by the hardware/software Observer 3.1, Noldus Technology, Holland. Animals were housed, and behavioural testing was performed in a different room during the light phase of the constant light-dark cycle with lights on at 6:00 and off at 18:00 h. Temperature was maintained at 21° C., and relative humidity was 50%. The mice were not handled except on the experimental days.

Group-housed males were used for the experiment. In the first part of the experiment, mice were given β-cyclodextrine or compound from example 9 at doses 1 and 10 mg/kg orally via a syringe, in a randomized order, 30 min prior to the open field observations performed in the identical animal house but a different room from that used for the social defeat interactions. Each animal was placed singly into the centre of a novel environment (arena 30×30 cm) of the PC controlled tracking apparatus Acti-track (Panlab, S. L., Spain) with infrared beam sensors. Over a 3-min testing period, the distance traveled, as a marker of locomotor/exploratory behaviour, in the open field was measured. Two days later, each mouse was defeated with a singly housed mouse exhibiting aggressive behaviour in a 4-min agonistic interaction. The procedure was repeated four times, 7 days apart. Immediately after the last (fourth)

agonistic interaction, each mouse was administered the same treatment as in the first part of the experiment. Thirty minutes following the drug administration, the animal was placed into the open field arena and distance traveled was measured, as described before. Data of two group-housed mice, which were seriously wounded during the aggressive dyadic encounters, were excluded from the statistical analysis.

Acute treatment of mice with compound from example 9 at doses 1 and 10 mg/kg reduced a hypolocomotion in an open field induced by agonistic interactions in mice. The results demonstrate that compound from example 9 can disinhibit suppressed locomotor activity in repeatedly defeated group-housed mice. This strongly supports the beneficiality of the compound from Example 9 on diseases involving stress-related behavior alterations.

In conclusion, presented effects of compound from example 9 observed in the social stress model used, which is close to real life events and emulates human psychiatric disorders, suggest possible antidepressant-like properties of the compound. See illustrative FIG. 26. In control mice group, repeated social interaction with aggressive conspecific yielded low locomotion in open-field test. Application of the compound from example 9, however, unblocked the suppressive effect of defeat experience and significantly increased locomotion in open-field.

Example 54

Effect of the Compound from Example 9 on the Pain Phenomena

The effect of the compound from example 9 was assessed on acute nociception in rat. Pain was evaluated by measurement of paw/tail withdrawal latencies. Male Wistar rats (Velaz, Czech Republic) were used. Animals were kept at 22° C. (relative humidity was 40-70%) under a 12-hour light/12-hour dark cycle. All experiments were approved by the Committee for Animal Care and conducted in accordance with the ethical guidelines of the International Association for the Study of Pain. The animals were randomly divided into experimental and testing groups groups. The compound from example 9 was dissolved in β-cyclodextrine (the concentration 1.0 mg/ml and 10 mg/kg injected intraperitoneally or β-cyclodextrine injected intraperitoneally in same volume).

Thermal nociception was determined using plantar test equipment (Ugo Basile, Italy). The latency (in seconds) of forelimb, hindlimb or tail withdrawals to the noxious thermal stimulation was measured. Each animal was placed individually in a clear plastic box with a clear glass floor, and was allowed to acclimatize for 10 min; the temperature and humidity in the testing room were kept in the same range as those in the housing rooms. The latencies were measured 3 times per session, separated by a minimum interval of 5 min, and the mean value was used for further analysis. Infrared intensity was set to 40% and the maximum cutoff value was set at 22 seconds to avoid thermal injury. The testing box was cleaned after each session.

The compound from Example 9 in dose 10 mg/kg applied to tail suppressed reactivity to painful stimuli and significantly prolonged interval of resistance to a painful stimulus, while the lower dose of this compound did not yield such an effect. These results strongly support the concept that the compound from example 9 exerts moderate anti-nociceptive and analgesic effects in animal model. Results of this experiment are summarized in the FIGS. 27 and 28.

After application of the compound from example 9 at 10 mg/kg dose, rats expressed significantly prolonged interval of resistance to a painful stimulus aimed at all their four limbs (* $p<0.001$, compared to control group “after”; ### $p<0.001$ compared to compound from example 9 in dose 10 mg/kg “before”). Such an effect was not however observed after application of compound from example 9 at 1 mg/kg dose (FIG. 27**). In another experiment higher dose of compound from example 9 also exerted an antinociceptive effect in pain-induced tail withdrawal (data not shown).

Likewise, the compound from example 9 at 10 mg/kg dose applied to tail suppressed reactivity to painful stimuli; while the lower dose of the compound from example 9 did not yield such an effect, see FIG. 28. Beneficial action of the compound from example 9 on the neuropathic pain model has also been documented by our experiments. These results strongly support the concept of anti-nociceptive action of compound from example 9 in an animal model.

Example 55

Effect of the Compound from Example 9 on the Ischemic Damage of the Neural Tissue The effect of compound from example 9 on cognitive coordination and motor activity was examined in stroke model of ischemic brain injury. Ischemic-hypoxic damage was induced by bilateral occlusion of common carotid arteries and subsequent confinement in box with 10% $O_2$ (for 30 min). The animals were injected i.p. by compound from example 9 dissolved in β-cyclodextrine (1 mg/kg) immediately after their removal from box. Ischemic group was injected only by β-cyclodextrine in the same time and volume. Surgery was conducted under anesthesia (xylazine 6 mg/kg, thiopental 50 mg/kg).

It is known that ischemia-hypoxia causes neuronal necrosis in specifically vulnerable areas of brain. The two-vessel occlusion/hypoxic model gives rise to stroke changes, for example in cells of the hippocampus, caudatoputamen and neocortex. As such structures are intimately involved in memory, cognitive and motor processes, ischemia/hypoxia leads to impairment in these functions. Used animal model of stroke damage dealing with ischemia/hypoxia has enabled the identification of deleterious phenomena that may be corrected or neutralized by drugs.

The effect of ischemic was evaluated a week after surgical procedures in AAPA task, beam walking and rotarod. Ischemia led to deterioration of motor activity (rotarod and beam walking) and deficit in cognitive coordination. Interestingly, total path in AAPA was not decreased.

Application of the compound from example 9 has no effect on disturbance of motor changes in rotarod and beam walking test (data not shown). But it improves cognitive deficit induced by ischemic/hypoxic procedures in AAPA task. (See FIG. 29). As a conclusion the compound from example 9 significantly counteracted cognitive deficit induced by ischemic hypoxic damage but without any effect on motor changes in dose of 1 mg/kg.

Ischemic rats treated with the compound from example 9 however performed equally well as controls (## $p<0.01$ compared to ischemic rats) demonstrating strong protective effect of the compound. None of the experimental condition affected locomotion in AAPA. All groups reached similar level of elapsed path during a session.

Example 56

Effect of the Compound from Example 9 on the Animal Model of Alzheimer Disease and Age-related Cognitive Decline The effect of the compound from example 9 on an animal model of age-related cognitive decline and neurodegenerative disorders (including Alzheimer disease) is documented. In the present experiment the effect of central muscarinic blockade by systemic administration of scopolamine at dose 2.0 mg/kg on both reinforced retention of the AAPA and re-acquisition of the AAPA in a new environment was investigated (by the standard method described previously; see Vales and Stuchlik, 2005).

The compound from example 9 was dissolved in β-cyclodextrine (at a concentration of 1.0 mg/ml). Animals were injected intraperitoneally with 1 ml/kg b.w. of this solution or with 1 ml/kg b.w. of β-cyclodextrine. All animals thus received the same volume of liquid per body weight in each injection. Injections were delivered 40 min prior to behavioural testing). Scopolamine hydrobromide (scopolamine; Sigma Aldrich) was dissolved in saline (0.9% NaCl, 2.0 mg/ml). Animals were injected intraperitoneally with 1 ml/kg b.w. of this solution or with 1 ml/kg b.w. of saline. All animals thus received the same volume of liquid per body weight in each injection. Injections were delivered 20 min prior to behavioural testing. Adult male hooded rats of the Long-Evans strain (3 months old; weighing 300-400g) was used.

The active allothetic place avoidance apparatus is described in example 28. Initially, non-injected rats were trained to avoid a sector located in the north of the Room 1 for four consecutive daily sessions (sessions 1-4). Subsequently, in session 5 they were injected with ether saline or scopolamine at the above-mentioned doses and the effect of the drug on well-pretrained place avoidance was examined (reinforced retention). During the following weekend, rats were left in the animal room without any manipulation. The next week, rats were trained under saline or scopolamine in the AAPA in the novel Room 2 for 5 days (sessions 6-10) in order to test re-acquisition of AAPA in a new environment, when they were already familiar with the procedural component of the AAPA task. The shock sector was defined in the south of the room in the Room 2 arena.

The rats were randomly divided into experimental groups. Group CONTROLS (n=8) received intraperitoneal injections of saline, second group (termed "scopolamine" in the FIG. 30) (n=8) received intraperitoneal injections of scopolamine at the dose of 2.0 mg/kg, and third group (n=8) received intraperitoneal injections of scopolamine at the dose of 2.0 mg/kg and compound from example 9 at the dose of 1.0 mg/ml i.p. respectively. Scopolamine and compound from example 9 were administered on days 5-9. Initial training without treatment was performed in arena 1 (sessions 1-5; with session 5 as reinforced retrieval under the effect of compounds) and reacquisition on a new arena was tested on days 6-9.) Note that the compound from example 9 tended to partly alleviating scopolamine induced deficit on days 5-9.

Effects of the compound from example 9 are documented here on the number of entrances, a spatially-selective parameter, which used frequently in the place avoidance studies, see FIG. 30. Visual inspection (during and after the injection) did not reveal any vocalizations, increased defecation, ataxia, or any other signs of behavioral discomfort. Rats were able to maintain the correct postural positions and their main neurological reflexes were preserved (grasping reflex, tilted platform test, contact placing reactions).

The results suggest that animals treated with the 2.0 mg/kg dose of scopolamine exhibited a significant impairment of place avoidance performance, both in the reinforced retention session, and re-acquisition training. This deficit tends to be decreased by i.p. administration of the compound from example 9. These results support the concept of protective effect of the compound from example 9 on age-related cognitive decline, Alzheimer dementia and possible other neurodegenerative disorders.

Example 57

Effect of Compound from Example 9 on the Spontaneous Electroencephalogram (EEG) and Evoked Potentials in Awaken Rats To assess the influence of the compound from example 9 on spontaneous EEG, evoked potentials and epileptic afterdischarges, recording electrodes were implanted into the epidural spaces of the adult Wistar rats. Rats were anaesthetized with isoflurane (1.5-2%) and 4 silver wire bare electrodes were inserted epidurally over sensorimotor cortex. Reference and ground electrodes were placed above cerebellum. The whole montage was fixed to the skull with dental acrylic.

After recovery period (1 week), animals were placed into the plastic boxes and connected to the Video EEG monitoring (VisionBrain/). After 1 hour of background recording the compound from example 9 was administered at the dose of 0.01 mg/kg and EEG was recorded for next 24 hours. Analysis of EEG was performed in a custom-based MATLAB script. Power of the EEG signal was calculated from FFT in frequency band 1.5-45 Hz. Length and duration of spike and wave afterdischarges (SPW) was measured from EEG to assess effect of compound from example 9 (0.01 mg/kg and 10 mg/kg) on epileptiform activity.

FIG. 31 shows the effect of compound from example 9 on the epileptic afterdischarges elicited by stimulation of the rat somatosensory areas. Note that the compound from example 9 tended to slightly decrease both duration and number of spike-wave episodes, although higher dose tended to increase these parameter (although the study requires further extension using more experimental subjects). This suggests a biphasic action of the compound from example 9 of the animal model of experimentally-induced epileptiform activity (SPW spike and wave).

Effect of the compound from example 9 on the spontaneous EEG power was measured at intervals 60 min and 180 min after application; see FIG. 32. Note that the compound from sample 9 changes the EEG power at the shorter interval.

The results strongly support the effect of compound from example 9 on the spontaneous EEG activity. Changes in power accompany various physiological (sleep) and pathophysiological conditions. Effect of the compound from example 9 on epileptic afterdischarges appears to be biphasic, with low doses tending to decrease this type of seizures, whilst higher doses may exacerbate it.

Industrial Applicability

The compounds mentioned in the presented patent are industrially producible and applicable for treatment of numerous diseases of central nervous system, e.g. the following:

1) hypoxic and ischaemic damage of the central nervous system, stroke, and other excitotoxicity-induced pathological alterations.
2) neurodegenerative changes and disorders
3) affective disorders, depression, PTSD and other stress-related diseases
4) schizophrenia and other psychotic disorders
5) pain, hyperalgesia and disorders of nociception
6) addictive disorders
7) multiple sclerosis and other autoimmune diseases
8) epilepsy and other seizure disorders
9) hyperplasic changes in CNS, CNS tumours including gliomas Literature Cited Cimadevilla J M, Wesierska M, Fenton A A, Bures J; Inactivating one hippocampus impairs avoidance of a stable room-defined place during dissociation of arena cues from room cues by rotation of the arena. Proc. Natl. Acad. Sci. USA 98 (2001), 3531-3536.

Morrow A L; Recent developments in the significance and therapeutic relevance of neuroactive steroids-Introduction to the special issue. Pharmacol Ther. 2007, 116(1), 1-6.

Paxinos G, Watson C R; The Rat Brain in Stereotaxic Coordinates (5th ed.), Elsevier Academic Press, San Diego (2005).

Petrovic M, Sedlacek M, Horak M, Chodounska H, Vyklický, L Jr.; 20-oxo-5beta-pregnan-3alpha-yl sulfate is a use-dependent NMDA receptor inhibitor. J. Neurosci. 2005, 25(37), 8439-50.

Stuchlik A, Petrasek T, Vales K; Dopamine D2 receptors and alpha 1-adrenoceptors synergistically modulate locomotion and behavior of rats in a place avoidance task. Behay. Brain Res. 189 (2008), 139-144.

Vales K, Stuchlik A; Central muscarinic blockade interferes with retrieval and reacquisition of active allothetic place avoidance despite spatial pretraining. Behav Brain Res. 161 (2005), 238-44.

Villmann C, Becker C M; On the hypes and falls in neuroprotection: targeting the NMDA receptor. Neuroscientist. 2007, 13(6), 594-615.

Weaver C E, Land M B, Purdy R H, Ruchards K G, Gibbs T T, Farb D H; J. Pharm. Exp. Ther. 293 (2000), 747.

Wesierska M, Dockery C, Fenton A A; Beyond memory, navigation, and inhibition: behavioral evidence for hippocampus-dependent cognitive coordination in the rat. J. Neurosci. 25 (2005), 2413-2419.

The invention claimed is:

1. Compounds of general formula (I)

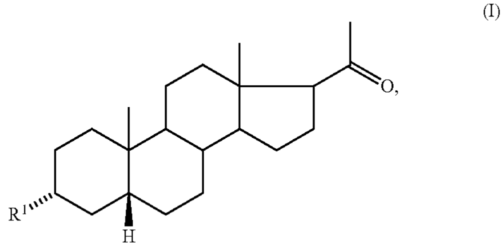

where $R^1$ stands for a group with formula $R^3OOC—R^2—C(R^4)—R^5—$, where $R^2$ stands for alkyl or alkenyl group with 1 to 18 carbon in a straight or a branching carbon chain, which may be substituted by one or more halogen atoms, amino group, which may be either free or protected by a removable protecting group, alkoxycarbonyl group, aromatic group, and/or heterocyclic group, in which the heteroatom means oxygen atom, sulfur, or nitrogen atom;

$R^3$ represents either a hydrogen atom or a protecting group of carboxyl groups;

$R^4$ is selected from a group consisting of oxygen, nitrogen, sulfur and two single bonded hydrogens; and $R^5$ ; is a bivalent atom selected from a group consisting of oxygen, nitrogen, and carbon;

with the proviso that $R^1$ is not; when $R^2$ is $(CH_{2)\ 0\text{-}3}$, $R^3$ is a hydrogen and both $R^4$ and $R^5$ are oxygen.

* * * * *